US009861597B2

(12) United States Patent
Chen et al.

(10) Patent No.: US 9,861,597 B2
(45) Date of Patent: Jan. 9, 2018

(54) GLUCONATE-BASED COMPOSITIONS AS A NEONATE ANTICONVULSANT

(71) Applicant: Penn State Research Foundation, University Park, PA (US)

(72) Inventors: Gong Chen, State College, PA (US); Zheng Wu, State College, PA (US)

(73) Assignee: Penn State Research Foundation, University Park, PA (US)

( * ) Notice: Subject to any disclaimer, the term of this patent is extended or adjusted under 35 U.S.C. 154(b) by 0 days.

(21) Appl. No.: 15/155,355

(22) Filed: May 16, 2016

(65) Prior Publication Data
US 2016/0338980 A1 Nov. 24, 2016

Related U.S. Application Data

(60) Provisional application No. 62/163,542, filed on May 19, 2015.

(51) Int. Cl.
*A61K 31/191* (2006.01)
*A61K 31/045* (2006.01)

(52) U.S. Cl.
CPC .......... *A61K 31/191* (2013.01); *A61K 31/045* (2013.01)

(58) Field of Classification Search
CPC .............................. A61K 31/191; A61K 31/045
See application file for complete search history.

(56) References Cited

U.S. PATENT DOCUMENTS

| 5,364,634 A | 11/1994 | Lew ............................... 424/451 |
| 5,705,188 A | 1/1998 | Junichi et al. ................. 424/450 |
| 6,113,948 A | 9/2000 | Heath et al. ................... 424/499 |
| 8,962,042 B2 | 2/2015 | Geng ............................ 424/725 |

FOREIGN PATENT DOCUMENTS

| WO | WO/1997/030731 | 8/1997 |
| WO | WO 2006/062683 | * 6/2006 |

OTHER PUBLICATIONS

Panayiotopoulos (The Epilepsies Seizures, Syndromes and Management Oxfordshire (UK): Bladon Medical Publishing (2005) Chapter 5).*
Borkenhagen et al. Pediatric Neurology 48 (2013) 469e471.*
Anastassiadis, S. et al. (2007) "Gluconic acid production," *Recent Patents on Biotechnology*, 167-180. (Abstract Only).
Arora, A. et al. (2005) "Iatrogenic calcinosis cutis—a rare differential diagnosis of soft-tissue infection in a neonate: A case report," *Journal of Orthopaedic Surgery* 13(2), 195-198.
Ben-Ari, Y. (2002) "Excitatory actions of gaba during development: the nature of the nurture," *Nature Reviews Neuroscience* 3(9), 728-739.
Ben-Ari, Y. et al. (2007) "GABA: A Pioneer Transmitter That Excites Immature Neurons and Generates Primitive Oscillations," *Physiological Reviews* 87(4), 1215-1284.

(Continued)

*Primary Examiner* — Savitha Rao
*Assistant Examiner* — Angela Brown-Pettigrew
(74) *Attorney, Agent, or Firm* — Medlen & Carroll, LLP

(57) ABSTRACT

The present invention is drawn to the treatment of neonatal patients exhibiting convulsion comprising administering a composition comprising a gluconate complex, wherein said gluconate complex lacks a divalent cation such as sodium gluconate.

15 Claims, 39 Drawing Sheets

(56) References Cited

OTHER PUBLICATIONS

Bialer, M. et al. (2010) "Key factors in the discovery and development of new antiepileptic drugs," *Nature Reviews Drug Discovery* 9(1), 68-82.
Blaesse, P. et al. (2009) "Cation-chloride cotransporters and neuronal function," *Neuron* 61(6), 820-838.
Boulenguez, P. et al. (2010) "Down-regulation of the potassium-chloride cotransporter KCC2 contributes to spasticity after spinal cord injury," *Natural Medicines* 16(3), 302-307.
Buckingham, S. C. et al. (2011) "Glutamate Release by Primary Brain Tumors Induces Epileptic Activity," *Nature Medicine* 17(10), 1269-1274.
Chen, G. et al. (1996) "Excitatory actions of GABA in developing rat hypothalamic neurones," *Journal of Physiology* 494(Pt 2), 451-464.
Chen, Q. et al. (2007) "Differential Roles of NR2A- and NR2B-Containing NMDA Receptors in Activity-Dependent Brain-Derived Neurotrophic Factor Gene Regulation and Limbic Epileptogenesis," *Journal of Neuroscience* 27(3), 542-552.
Connell, J. et al. (1989) "Clinical and EEG response to anticonvulsants in neonatal seizures," *Archives of Disease in Childhood* 64(4 Spec No), 459-464.
Cuddapah, V. A. et al. (2013) "Bradykinin-Induced Chemotaxis of Human Gliomas Requires the Activation of KCa3.1 and ClC-3," *Journal of Neuroscience* 33(4), 1427-1440.
Deidda, G. et al. (2015) "Early depolarizing GABA controls critical period plasticity in the rat visual cortex," *Nature Neuroscience* 18(1), 87-96.
Deriy, L. V. et al. (2009) "The Granular Chloride Channel ClC-3 Is Permissive for Insulin Secretion," *Cell Metabolism* 10(4), 316-323.
Dickerson, L. W. et al. (2002) "Altered GABAergic function accompanies hippocampal degeneration in mice lacking ClC-3 voltage-gated chloride channels," *Brain Research* 958(2), 227-250.
Duan, D. et al. (2001) "Functional inhibition of native volume-sensitive outwardly rectifying anion channels in muscle cells and Xenopus oocytes by anti-ClC-3 antibody," *Journal of Physiology* 531(Pt 2), 437-444.
Duran, C. et al. (2010) "Chloride Channels: Often enigmatic, rarely predictable," *Annual Review of Physiology* 72, 95-121.
Dzhala, V. I. et al. (2005) "NKCC1 transporter facilitates seizures in the developing brain," *Natural Medicines* 11(11), 1205-1213.
Farwell, J. R. et al. (1990) "Phenobarbital for Febrile Seizures—Effects on Intelligence and on Seizure Recurrence," *New England Journal of Medicine* 322(6), 364-369.
Földy, C. et al. (2010) "Regulation of Fast-Spiking Basket Cell Synapses by the Chloride Channel ClC-2," *Nature Neuroscience* 13(9), 1047-1049.
Glykys, J. et al. (2014) "Local Impermeant Anions Establish the Neuronal Chloride Concentration," *Science* 343(6171), 670-675.
Glykys, J. et al. (2009) "Differences in cortical vs. subcortical GABAergic signaling: a candidate mechanism of electroclinical dissociation of neonatal seizures," *Neuron* 63(5), 657-672.
González, W. et al. (2009) "Seizures and EEG findings in an adult patient with DiGeorge syndrome: A case report and review of the literature," *Seizure—European Journal of Epilepsy* 18(9), 648-651.
Graves, A. R. et al. (2008) "The Cl-/H+ antiporter ClC-7 is the primary chloride permeation pathway in lysosomes," *Nature* 453(7196), 788-792.
Habela, C. W. et al. (2008) "ClC3 Is a Critical Regulator of the Cell Cycle in Normal and Malignant Glial Cells," *Journal of Neuroscience* 28(37), 9205-9217.
Hara-Chikuma, M. et al. (2005) "ClC-3 chloride channels facilitate endosomal acidification and chloride accumulation," *Journal of Biological Chemistry* 280(2), 1241-1247.
Haug, K. et al. (2003) "Mutations in CLCN2 encoding a voltage-gated chloride channel are associated with idiopathic generalized epilepsies," *Nature Genetics* 33(4), 527-532.
Huang, W. C. et al. (2012) "Calcium-Activated Chloride Channels (CaCCs) Regulate Action Potential and Synaptic Response in Hippocampal Neurons," *Neuron* 74(1), 179-192.
Huang, Y.-Y. et al. (2014) "ClC-3 deficiency protects preadipocytes against apoptosis induced by palmitate in vitro and in type 2 diabetes mice," *Apoptosis* 19(11), 1559-1570.
Jensen, F. E. (2009) "Neonatal Seizures: An Update on Mechanisms and Management," *Clinics in Perinatology* 36(4), 881.
Jentsch, T. J. (2007) "Chloride and the endosomal—lysosomal pathway: emerging roles of CLC chloride transporters," *Journal of Physiology* 578(Pt 3), 633-640.
Kahle, K. T. et al. (2008) "Roles of the cation-chloride cotransporters in neurological disease," *Nature Clinical Practice. Neurology* 4(9), 490-503.
Kaila, K. et al. (2014) "Cation-chloride cotransporters in neuronal development, plasticity and disease," *Nature Reviews. Neuroscience* 15(10), 637-654.
Karademir, S. et al. (1993) "Left Ventricular Dysfunction Due to Hypocalcemia in a Neonate," *Japanese Heart Journal* 34(3), 355-359.
Kawasaki, M. et al. (1994) "Cloning and expression of a protein kinase C-regulated chloride channel abundantly expressed in rat brain neuronal cells," *Neuron* 12(3), 597-604.
Kleefusz-Lie, A. et al. (2009) "CLCN2 variants in idiopathic generalized epilepsy," *Nature Genetics* 41(9), 954-955.
Li, D.-Q. et al. (2009) "Suppression of Sulfonylurea- and Glucose-Induced Insulin Secretion In Vitro and In Vivo in Mice Lacking the Chloride Transport Protein ClC-3," *Cell Metabolism* 10(4), 309-315.
Li, X. et al. (2002) "The ClC-3 chloride channel promotes acidification of lysosomes in CHO-K1 and Huh-7 cells," *American Journal of Physiology—Cell Physiology* 282(6), C1483-C1491.
Liu, J. et al. (2013) "ClC-3 deficiency prevents apoptosis induced by angiotensin II in endothelial progenitor cells via inhibition of NADPH oxidase," *Apoptosis* 18(10), 1262-1273.
Löscher, W. et al. (2013) "Cation-chloride cotransporters NKCC1 and KCC2 as potential targets for novel antiepileptic and antiepileptogenic treatments," *Neuropharmacology* 69, 62-74.
Manzar, S. (2001) "Transient Pseudohypoparathyroidism and Neonatal Seizure," *Journal of Tropical Pediatrics* 47(2), 113-114.
Matsuda, J. J. et al. (2008) "Overexpression of ClC-3 in HEK293T cells yields novel currents that are pH dependent," *American Journal of Physiology—Cell Physiology* 294(1), C251-C262.
Miller, R. A. et al. (1977) "Degradation rates of oral resorbable implants (polylactates and polyglycolates): Rate modification with changes in PLA/PGA copolymer ratios," *Journal of Biomedical Materials Research* 11(5), 711-719.
Narang, M. et al. (2006) "Neonatal pseudohypoparathyroidism," *Indian Journal of Pediatrics* 73(1), 97-98.
Naseer, M. I. et al. (2009) "Maternal epileptic seizure induced by pentylenetetrazol: apoptotic neurodegeneration and decreased GABAB1 receptor expression in prenatal rat brain," *Molecular Brain* 2, 20.
Niemeyer, M. I. et al. (2010) "No evidence for a role of CLCN2 variants in idiopathic generalized epilepsy," *Nature Genetics* 42(1), 3-3.
Olsen, M. L. et al. (2003) "Expression of Voltage-Gated Chloride Channels in Human Glioma Cells," *Journal of Neuroscience* 23(13), 5572-5582.
Painter, M. J. et al. (1999) "Phenobarbital Compared with Phenytoin for the Treatment of Neonatal Seizures," *New England Journal of Medicine* 341(7), 485-489.
Pallud, J. et al. (2014) "Cortical GABAergic excitation contributes to epileptic activities around human glioma," *Science Translational Medicine* 6(244), 244ra289-244ra289.
Picollo, A. et al. (2005) "Chloride/proton antiporter activity of mammalian CLC proteins ClC-4 and ClC-5," *Nature* 436(7049), 420-423.
Pressler, R. M. et al. (2015) "Bumetanide for the treatment of seizures in newborn babies with hypoxic ischaemic encephalopathy (NEMO): an open-label, dose finding, and feasibility phase 1/2 trial," *Lancet Neurology* 14(5), 469-477.
Puskarjov, M. et al. (2014) "Pharmacotherapeutic targeting of cation-chloride cotransporters in neonatal seizures," *Epilepsia* 55(6), 806-818.

(56) References Cited

OTHER PUBLICATIONS

Putney, S. D. et al. (1998) "Improving protein therapeutics with sustained-release formulations," *Nature Biotechnology* 16(2), 153-157.

Qi, J. et al. (2006) "Cyclothiazide induces robust epileptiform activity in rat hippocampal neurons both in vitro and in vivo," *Journal of Physiology* 571(3), 605-618.

Qian, B. et al. (2011) "Epileptiform response of CA1 neurones to convulsant stimulation by cyclothiazide, kainic acid and pentylenetetrazol in anaesthetized rats," *Seizure—European Journal of Epilepsy* 20(4), 312-319.

Racine, R. et al. (1972) "Modification of seizure activity by electrical stimulation. 3. Mechanisms," *Electroencephalography and Clinical Neurophysiology* 32(3), 295-299.

Riazanski, V. et al. (2011) "Presynaptic CLC-3 determines quantal size of inhibitory transmission in the hippocampus," *Nature Neuroscience* 14(4), 487-494.

Rinke, I. et al. (2010) "ClC-2 Voltage-Gated Channels Constitute Part of the Background Conductance and Assist Chloride Extrusion," *Journal of Neuroscience* 30(13), 4776-4786.

Sagar, H. J. et al. (1987) "Hippocampal neuron loss in temporal lobe epilepsy: correlation with early childhood convulsions," *Annals of Neurology* 22(3), 334-340.

Sass, K. J. et al. (1995) "Verbal memory impairment resulting from hippocampal neuron loss among epileptic patients with structural lesions," *Neurology* 45, 2154-2158.

Scheel, O. et al. (2005) "Voltage-dependent electrogenic chloride/proton exchange by endosomal CLC proteins," *Nature* 436(7049), 424-427.

Silverstein, F. S. et al. (2007) "Neonatal seizures," *Annals of Neurology* 62(2), 112-120.

Slaughter, L. A. et al. (2013) "Pharmacological Treatment of Neonatal Seizures: A Systematic Review," *Journal of Child Neurology* 28(3), 351-364.

Turner, T. et al. (1974) "Proceedings: Comparisons of phenobarbitone, magnesium sulphate, and calcium gluconate in treatment of neonatal hypocalcaemic convulsions," *Archives of Disease in Childhood* 49(3), 244-244.

Tyzio, R. et al. (2006) "Maternal Oxytocin Triggers a Transient Inhibitory Switch in GABA Signaling in the Fetal Brain During Delivery," *Science* 314(5806), 1788-1792.

Van Rooij, L. G. M. et al. (2013) "Treatment of neonatal seizures," *Seminars in Fetal and Neonatal Medicine* 18(4), 209-215.

Verkman, A. S. et al. (2009) "Chloride channels as drug targets," *Nature Reviews Drug Discovery* 8(2), 153-171.

Wang, D. D. et al. (2011) "Blocking Early GABA Depolarization with Bumetanide Results in Permanent Alterations in Cortical Circuits and Sensorimotor Gating Deficits," *Cerebral Cortex* 21(3), 574-587.

Wang, G.-X. et al. (2003) "Functional effects of novel anti-ClC-3 antibodies on native volume-sensitive osmolyte and anion channels in cardiac and smooth muscle cells," *American Journal of Physiology—Heart and Circulatory Physiology* 285(4), H1453-H1463.

Wang, X. Q. et al. (2006) "CLC-3 Channels Modulate Excitatory Synaptic Transmission in Hippocampal Neurons," *Neuron* 52(2), 321-333.

Wu, Z. et al. (2009) "Protective Effect of Resveratrol against Kainate-induced Temporal Lobe Epilepsy in Rats," *Neurochemical Research* 34(8), 1393-1400.

Zheng, L.-Y. et al. (2013) "Deficiency of volume-regulated ClC-3 chloride channel attenuates cerebrovascular remodelling in DOCA-salt hypertension," *Cardiovascular Research* 100(1), 134-142.

Zhou, J.-G. et al. (2005) "Regulation of Intracellular Cl—Concentration through Volume-regulated ClC-3 Chloride Channels in A10 Vascular Smooth Muscle Cells," *Journal of Biological Chemistry* 280(8), 7301-7308.

\* cited by examiner

Figure 1A
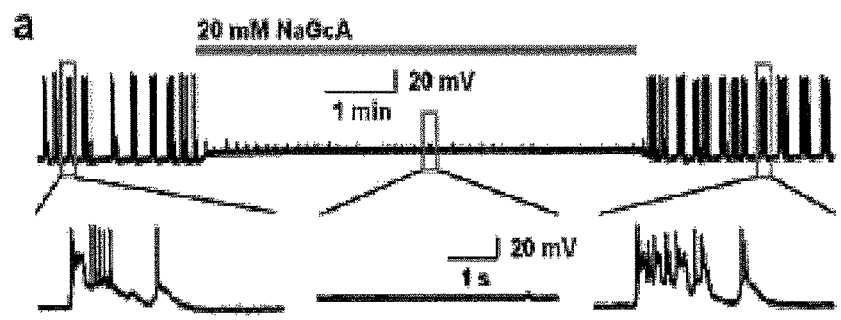
Figure 1B
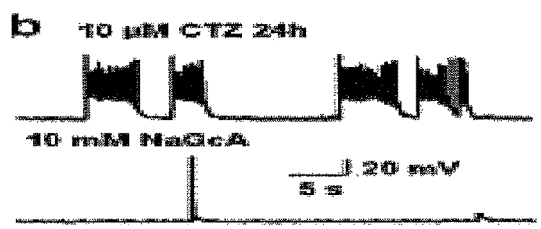
Figure 1C
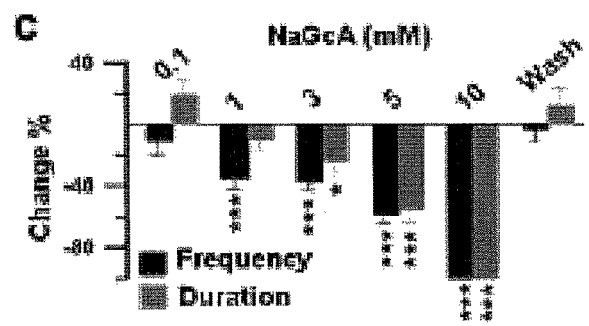
Figure 1

Figure 1D
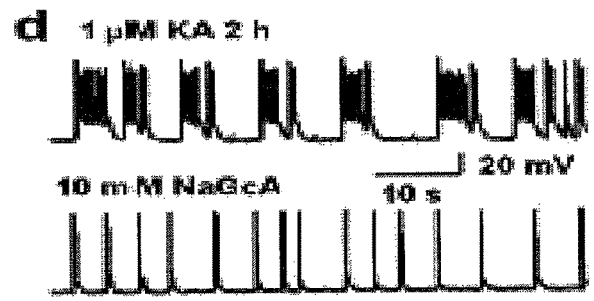
Figure 1E
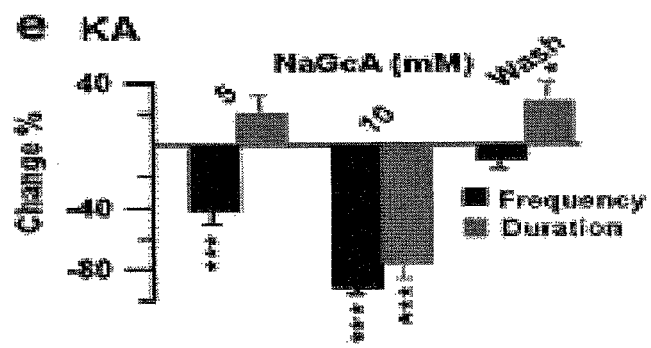
Figure 1F
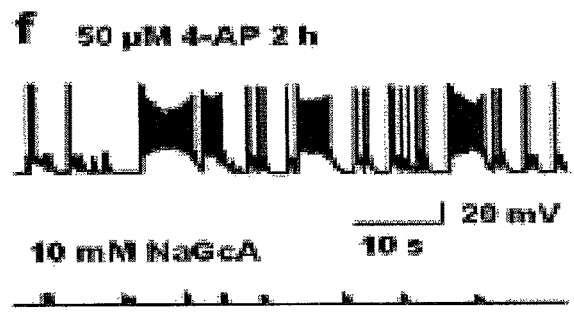
Figure 1 (Cont'd)

Figure 1G
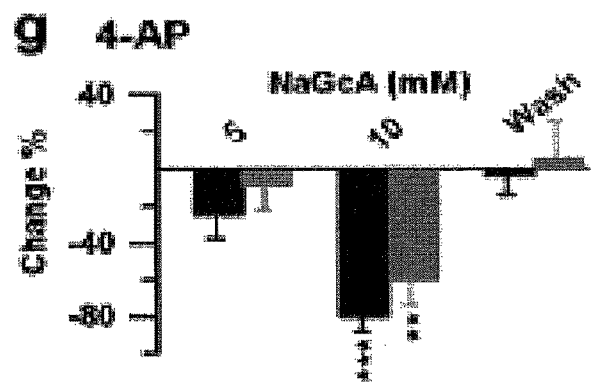
Figure 1H
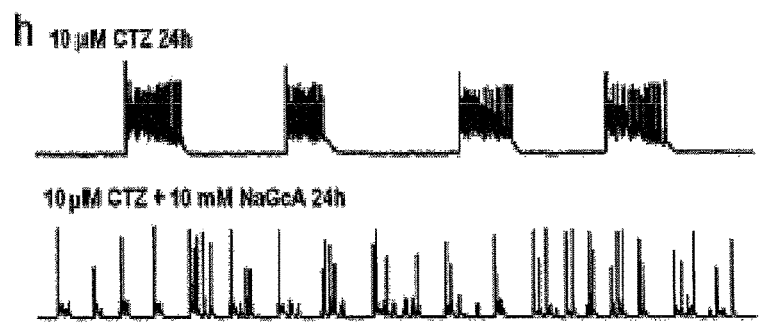
Figure 1 (Cont'd)

Figure 1J
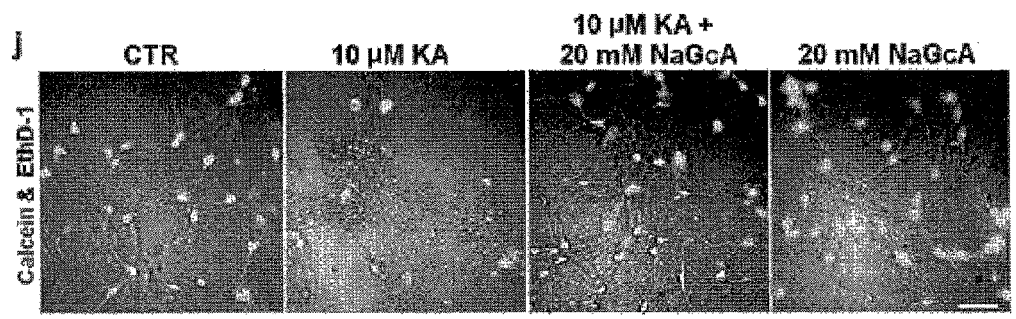
Figure 1K
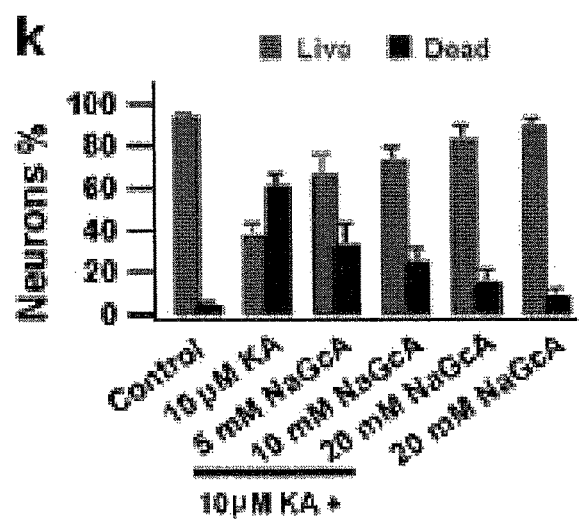
Figure 1 (Cont'd)

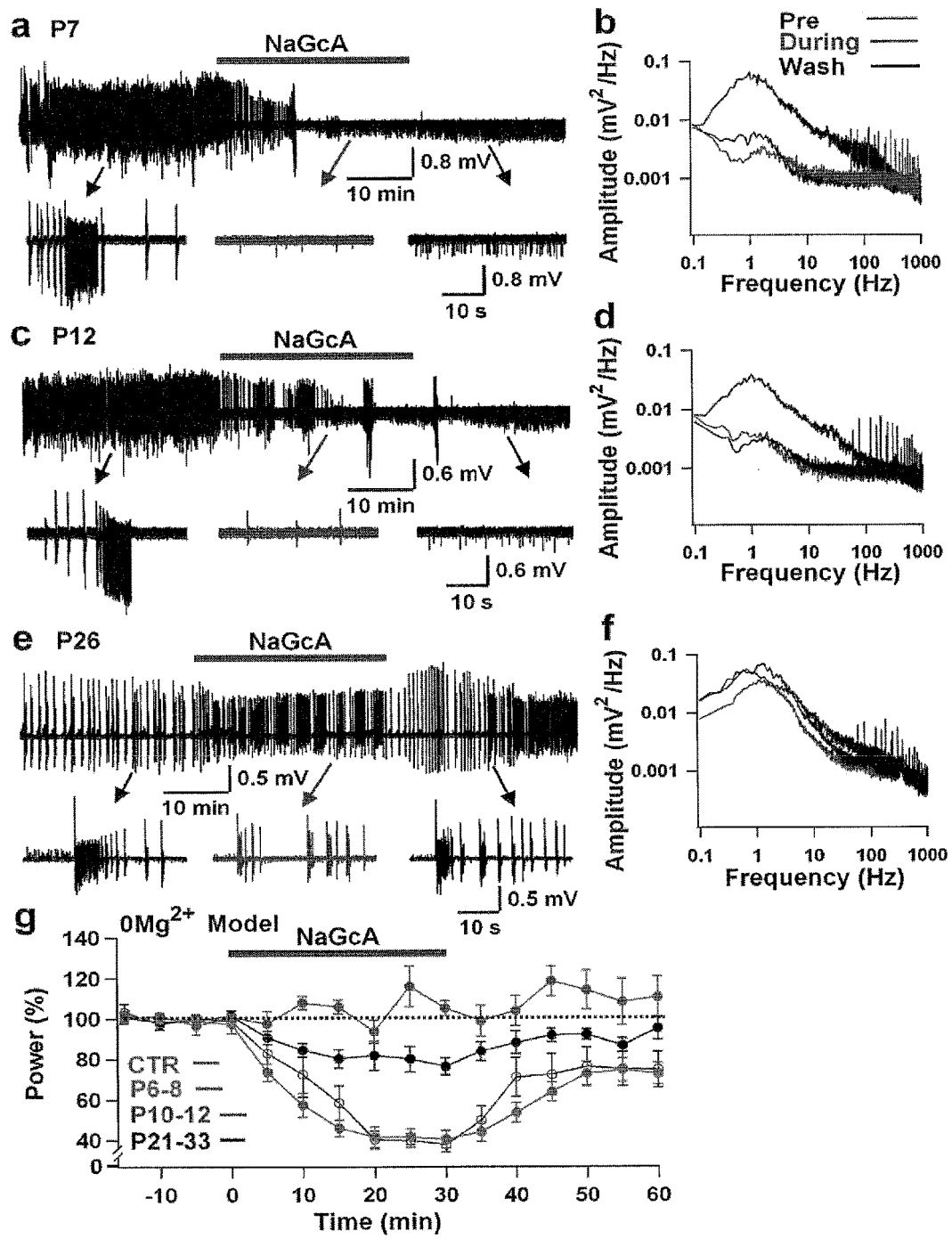
Figures 3A-G

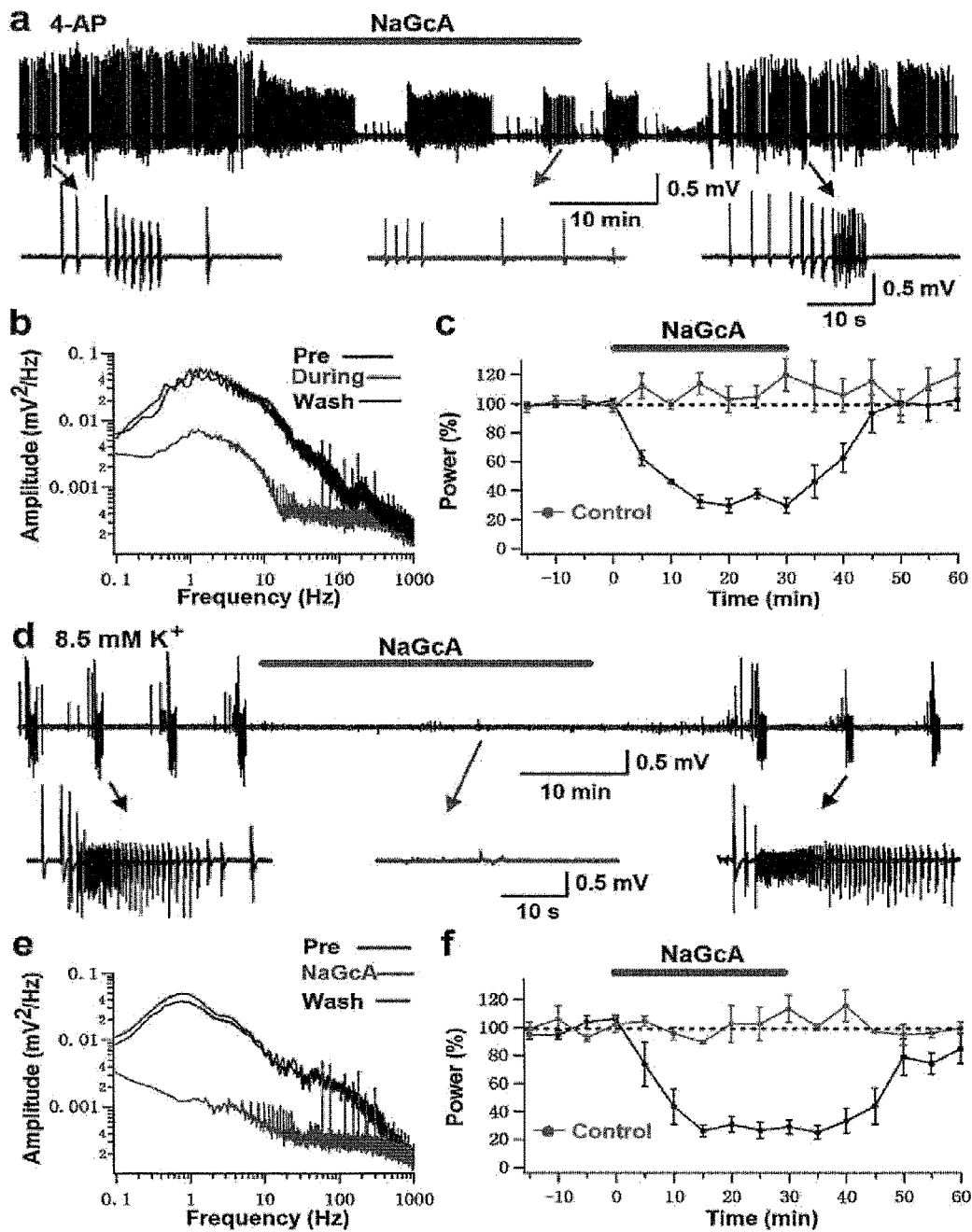
Figure 4A-F

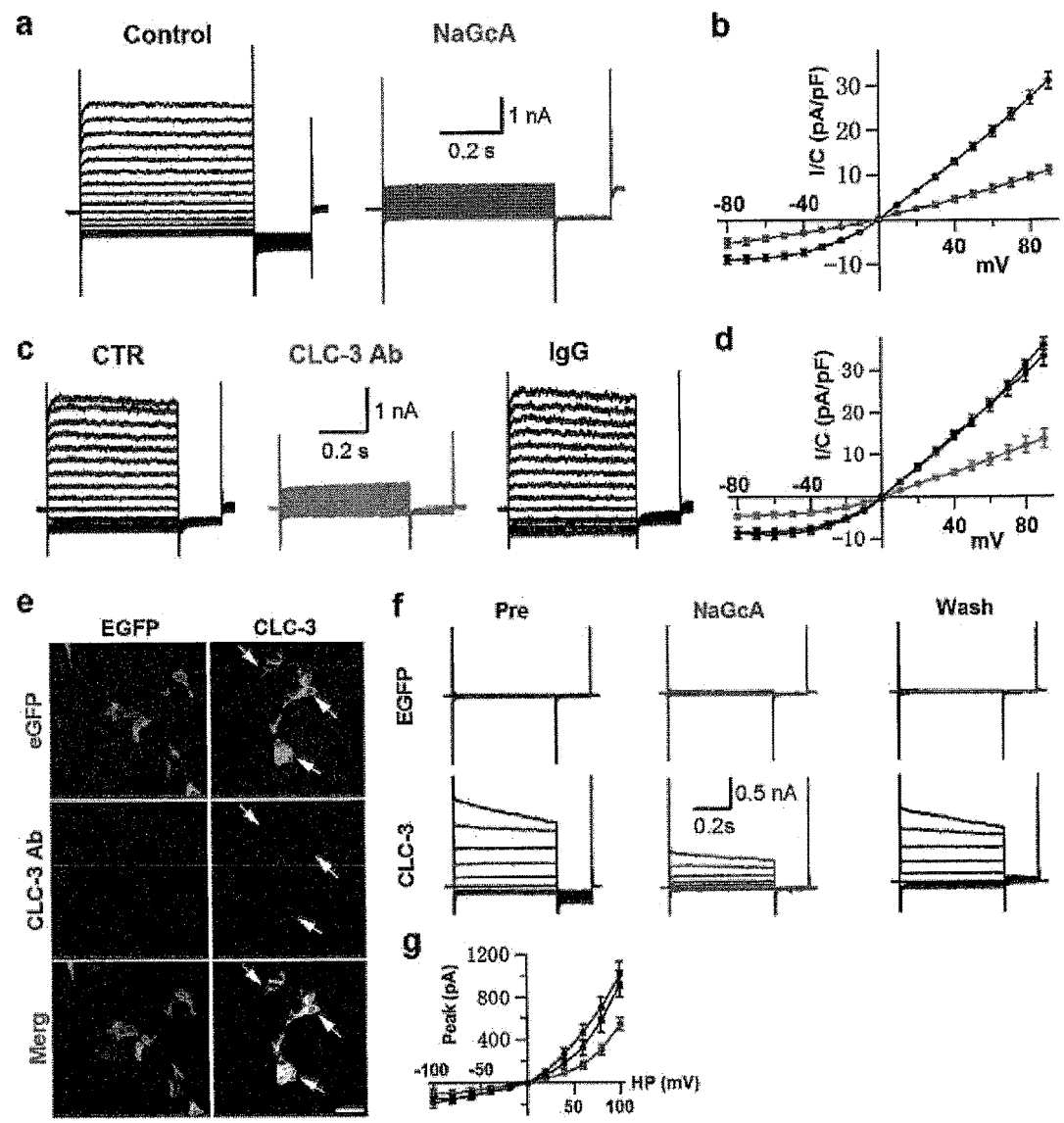
Figure 5A-G

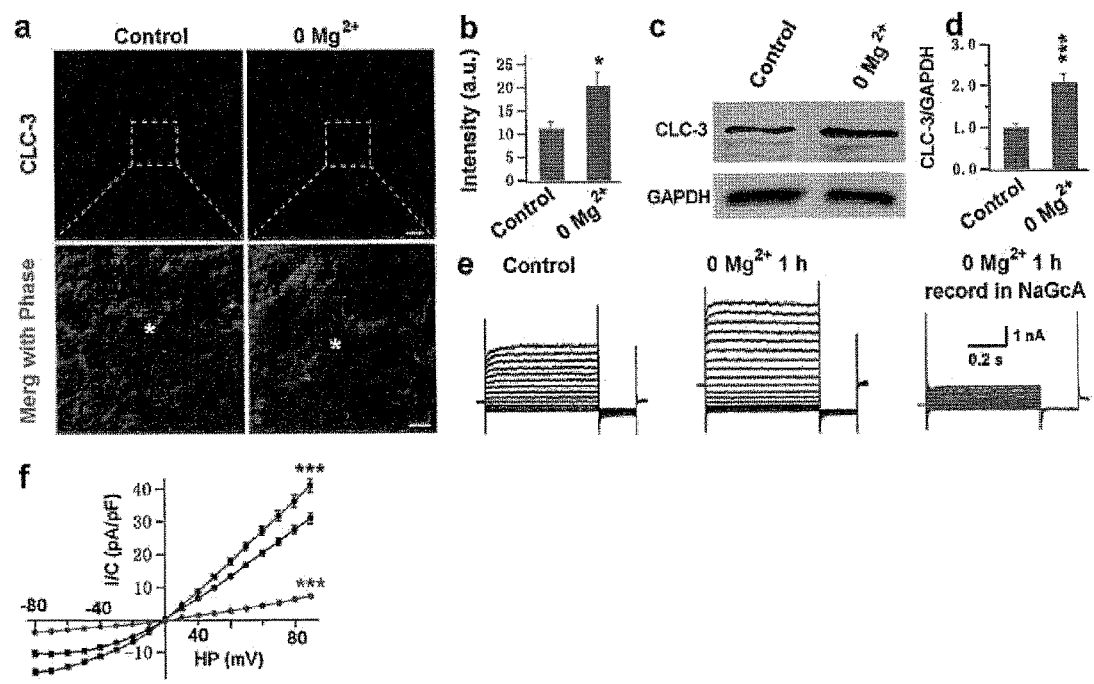
Figures 6A-F

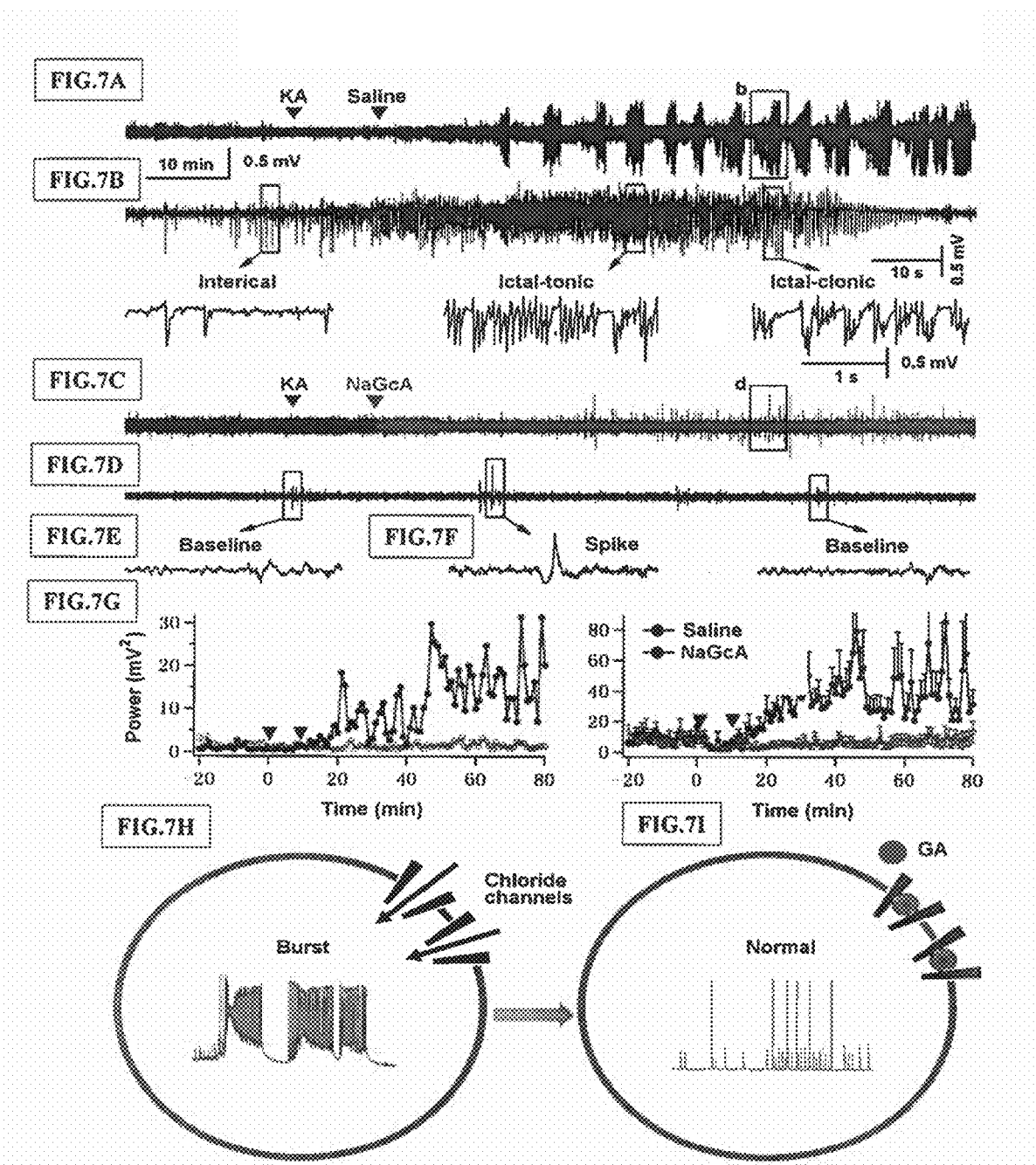
FIGURE 7A - I

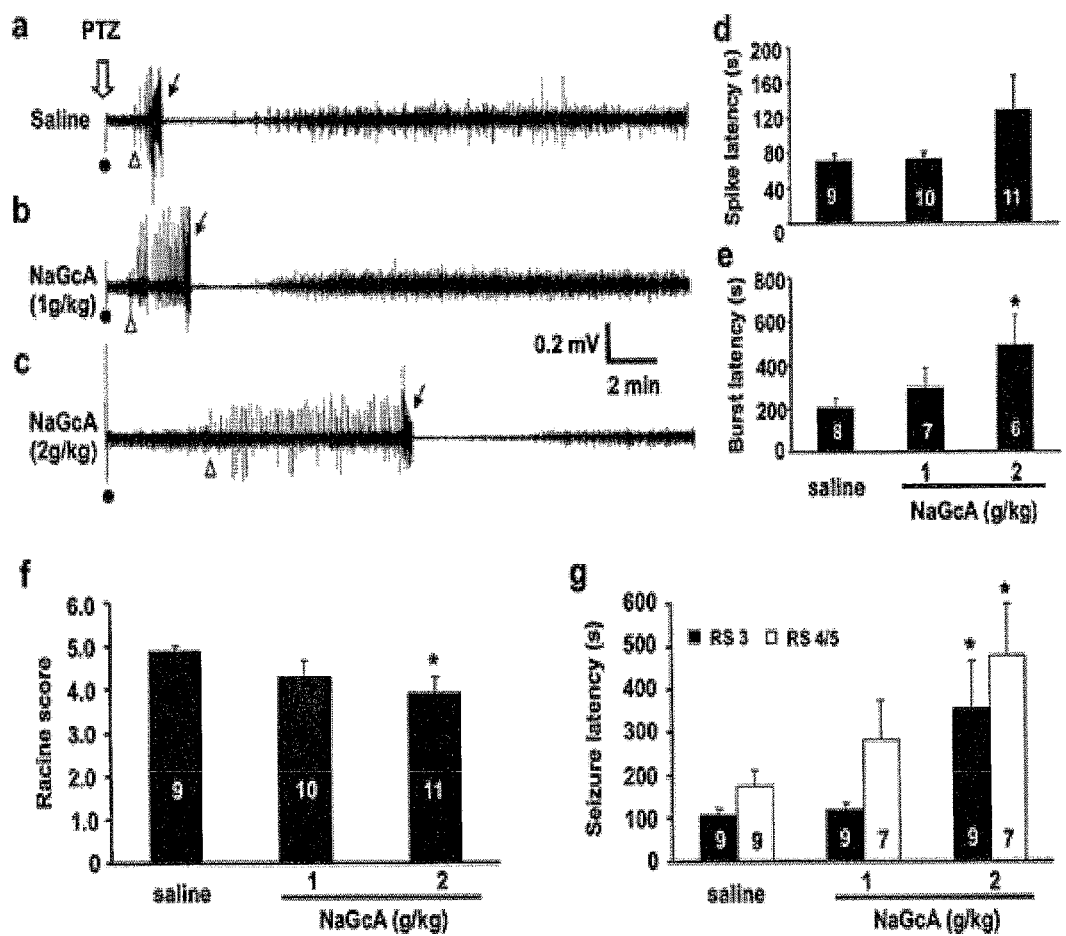
Figures 8A-G

A
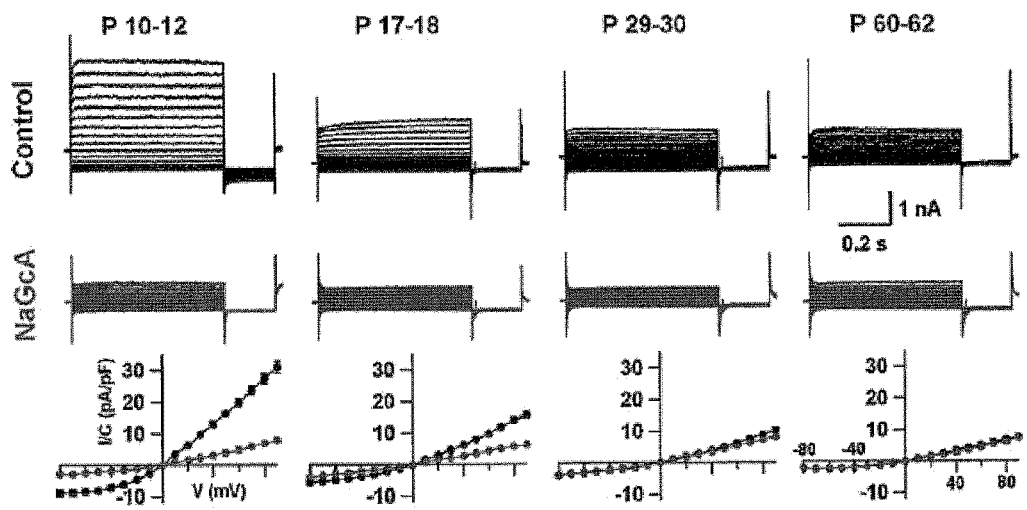
B.
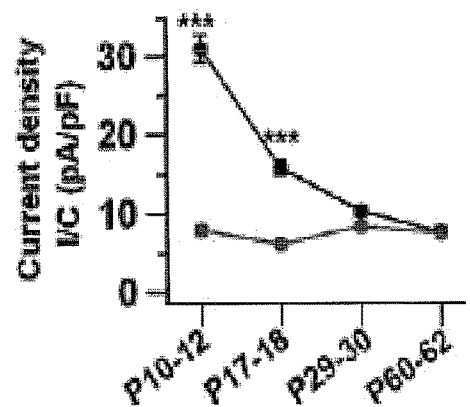
Figure 11

C
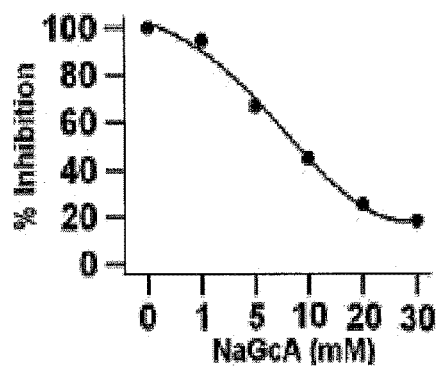
D
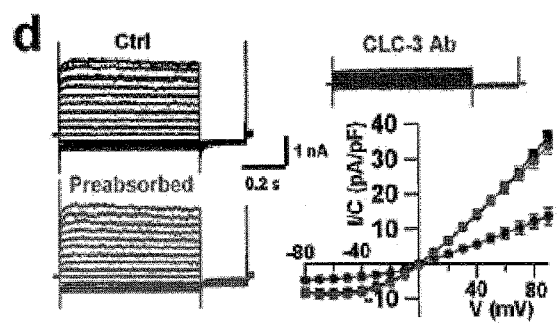
Figure 11 (cont'd)

E
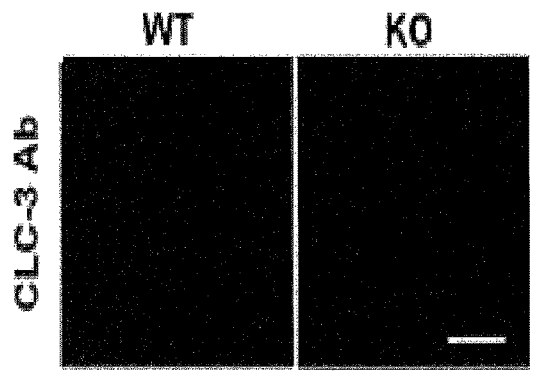
F
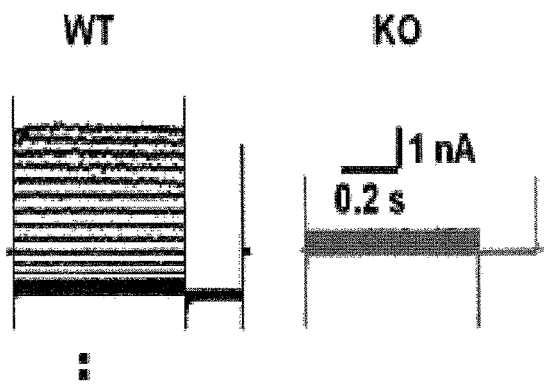
Figure 11 (cont'd)

G
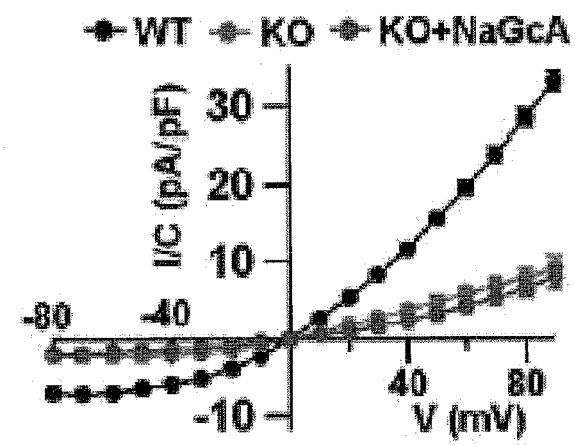
H
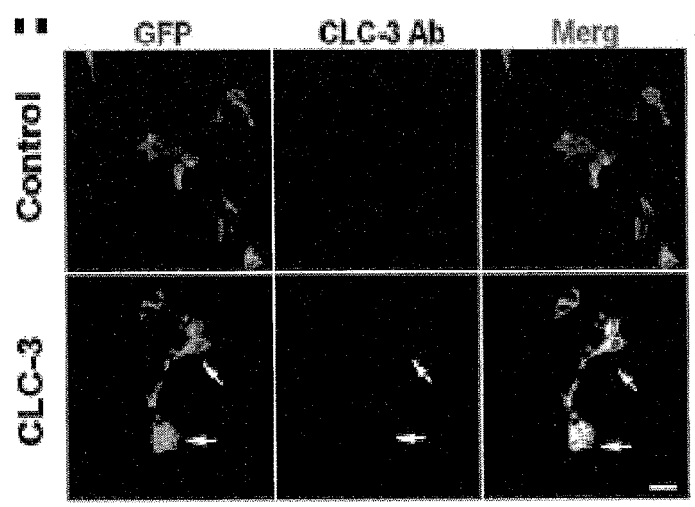
Figure 11 (cont'd)

I
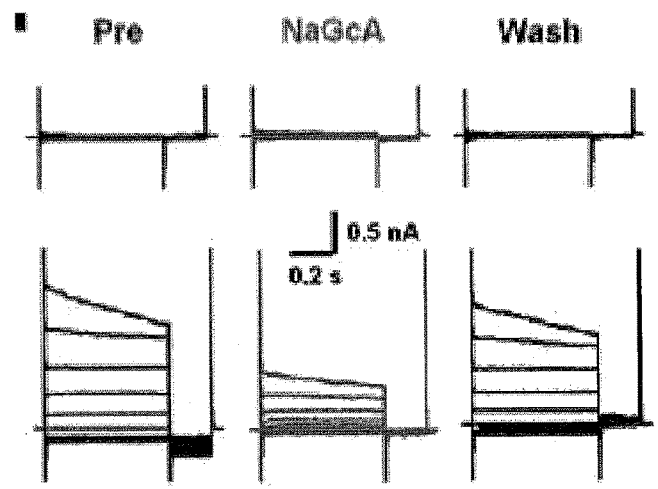
J
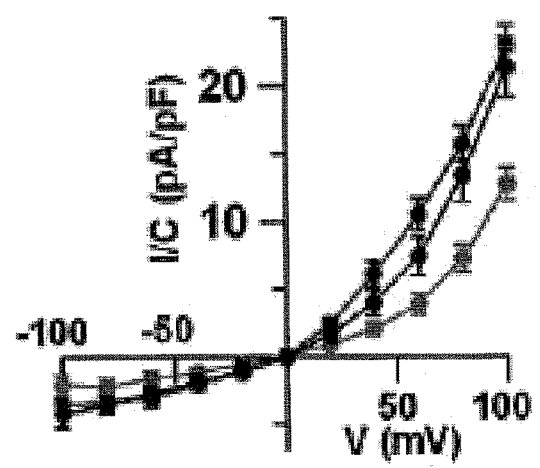
Figure 11 (cont'd)

A
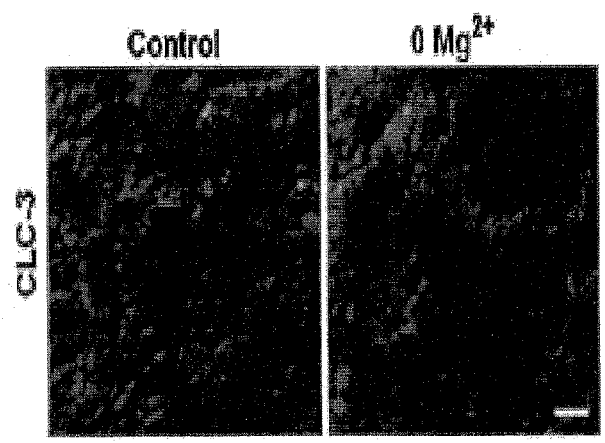
B
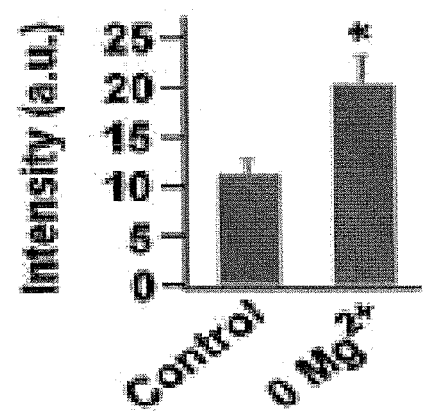
Figure 12

C
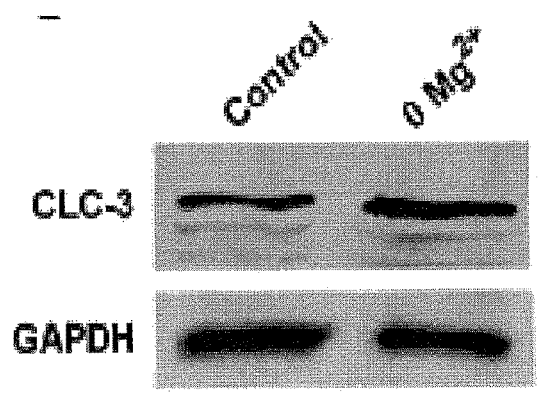
D
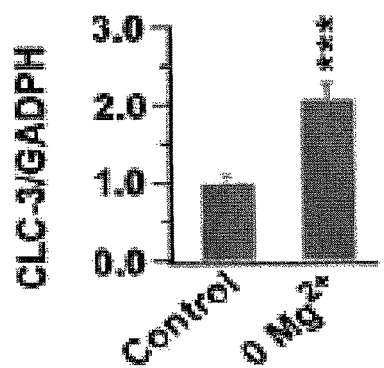
Figure 12 (cont'd)

E
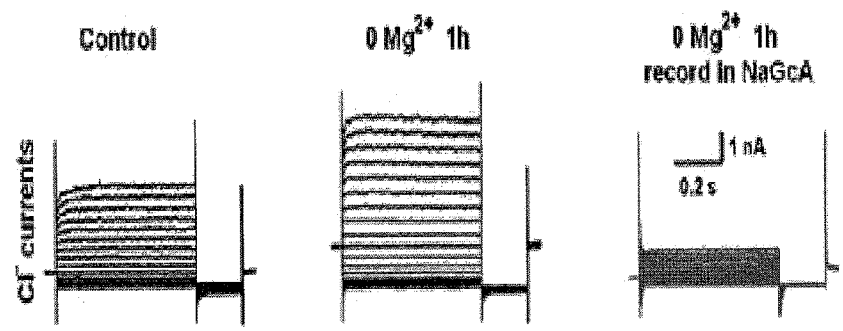
F
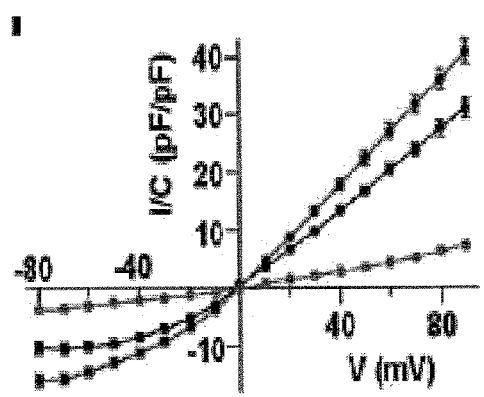
Figure 12 (cont'd)

G
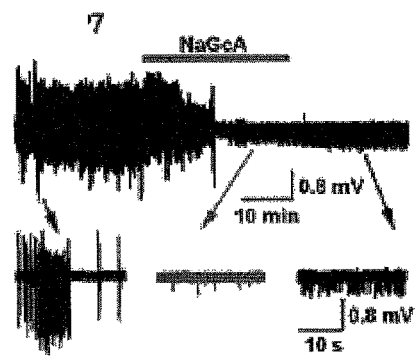
H
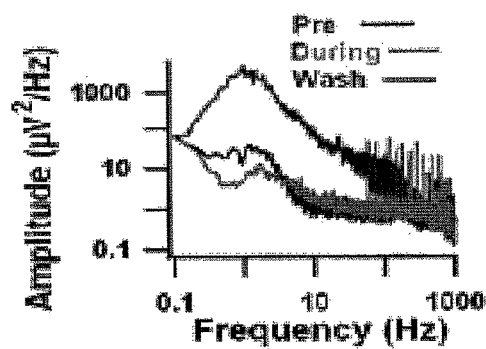
Figure 12 (cont'd)

I
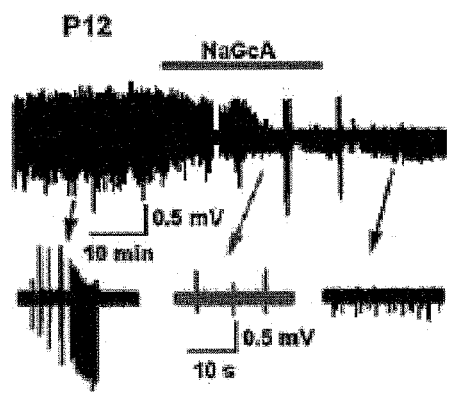
J
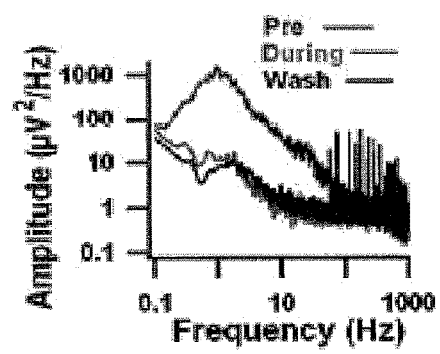
Figure 12 (cont'd)

K
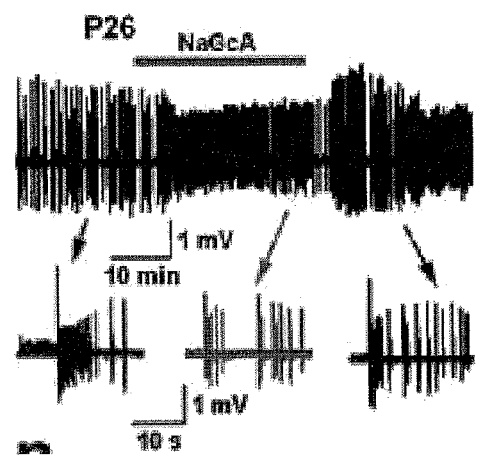
L
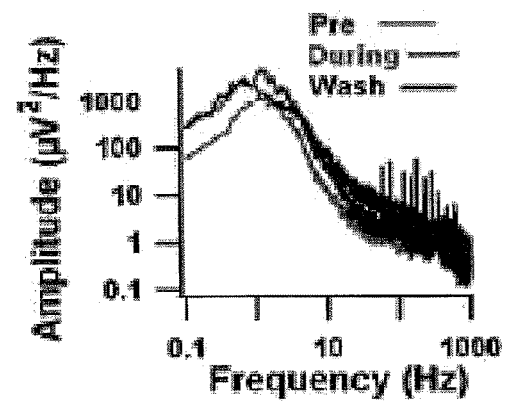
Figure 12 (cont'd)

M
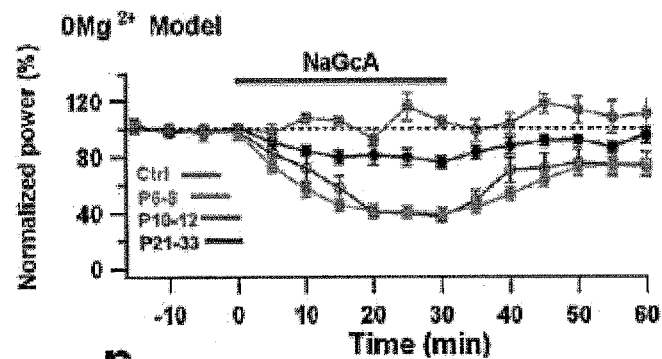
N
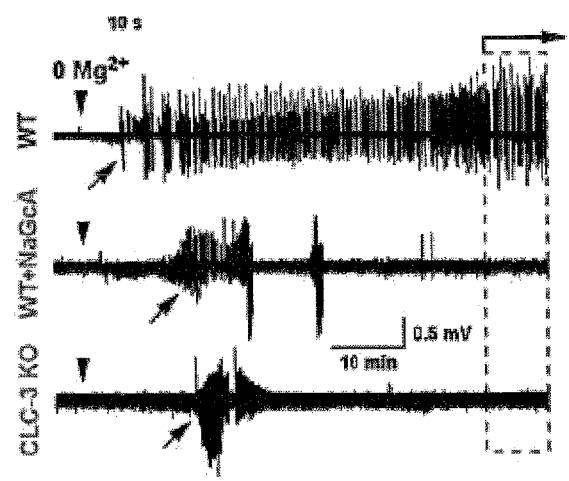
Figure 12 (cont'd)

O
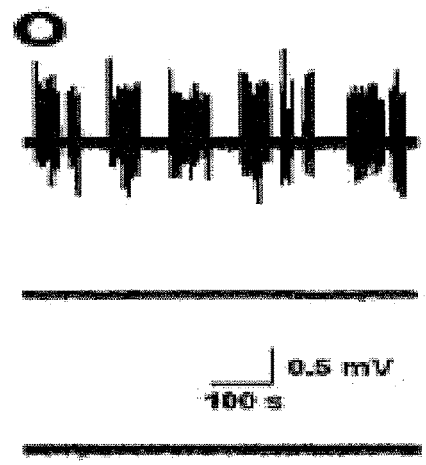
P
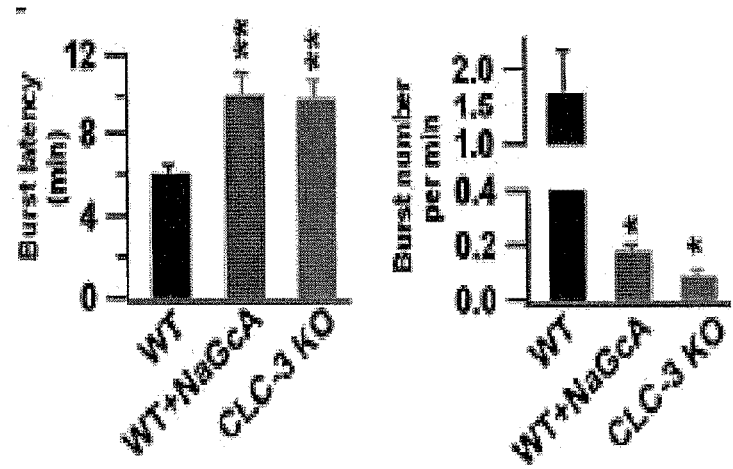
Figure 12 (cont'd)

A
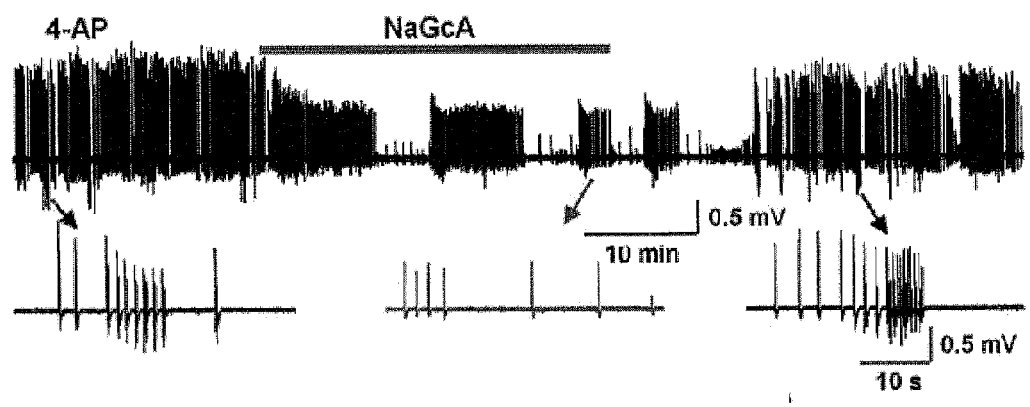
B
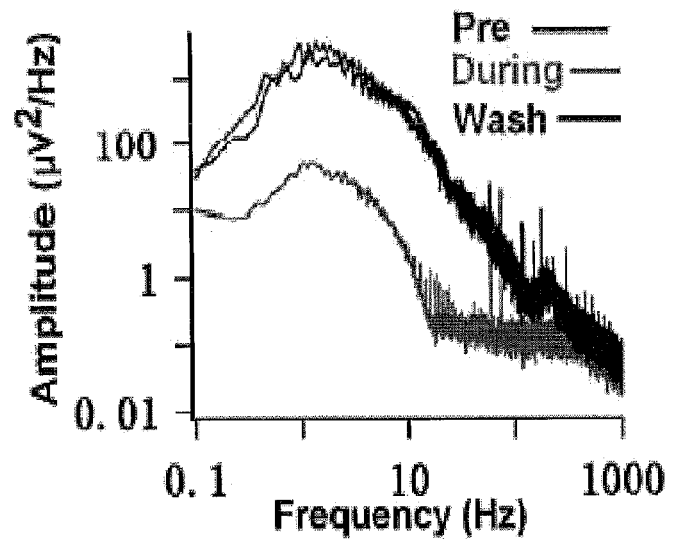
Figure 13

C
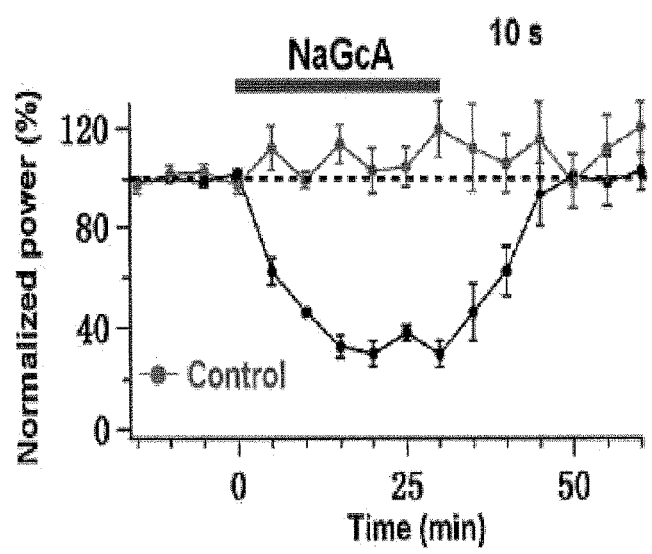
D
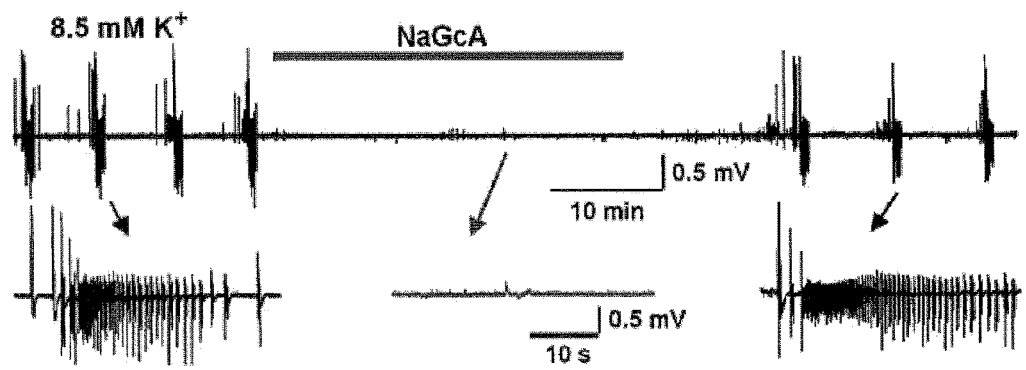
Figure 13 (cont'd)

E
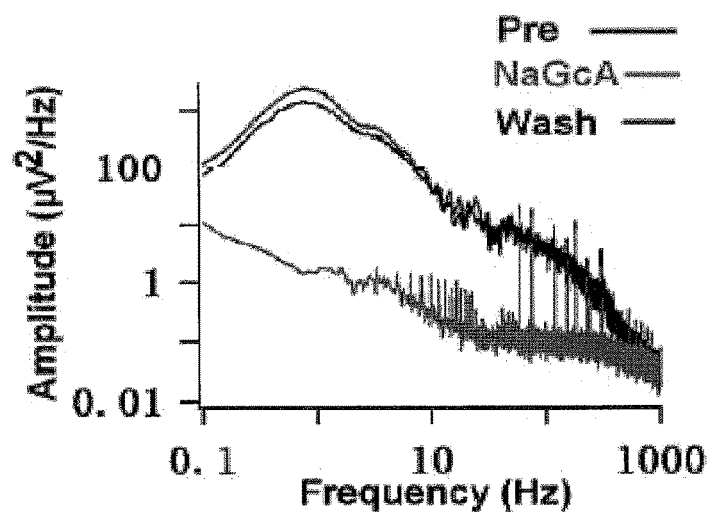
F
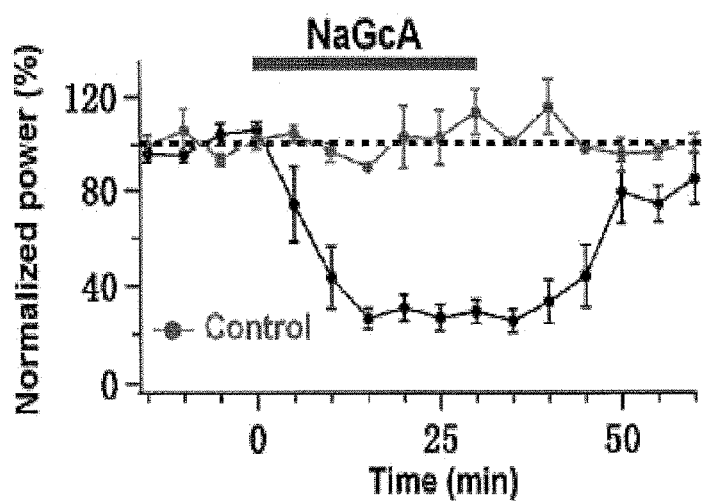
Figure 13 (cont'd)

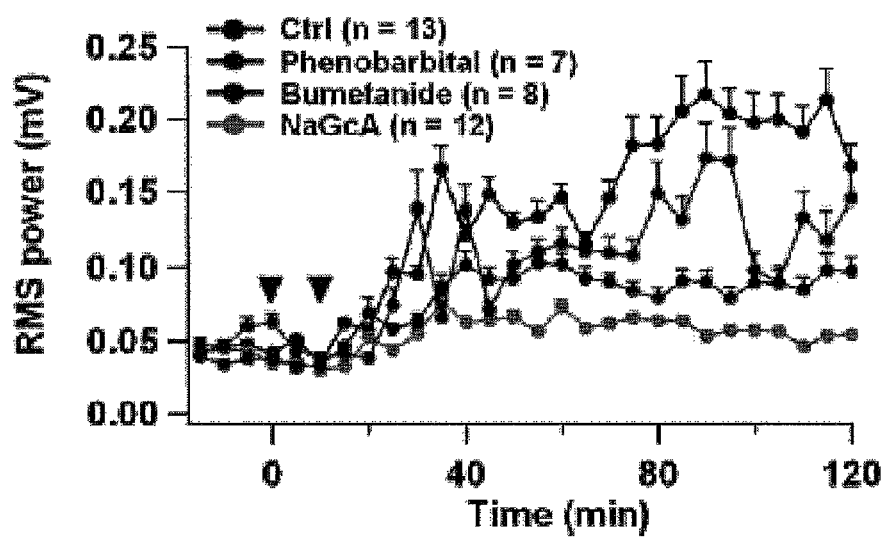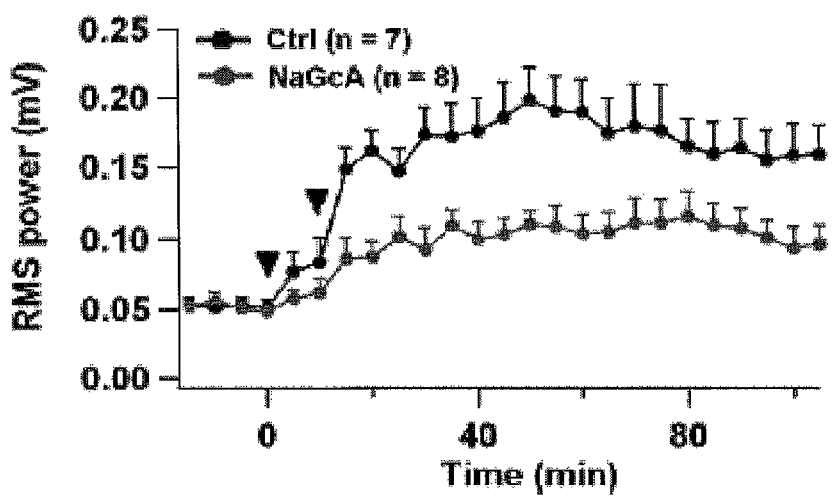
Figure 14 (cont'd)

A
B
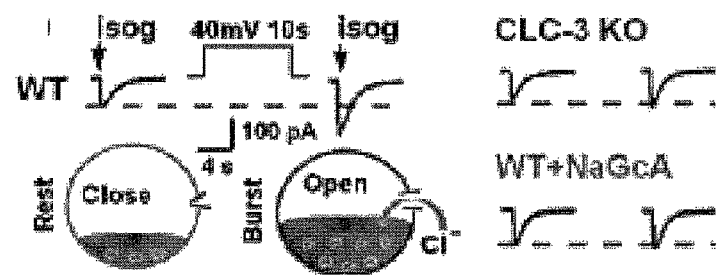
C
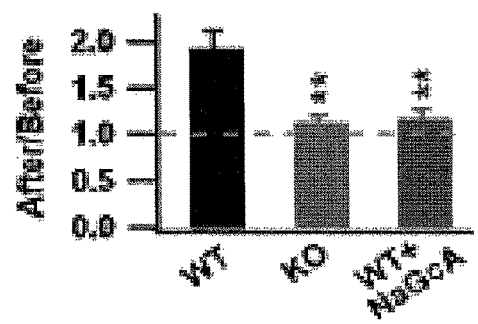
Figure 16

D
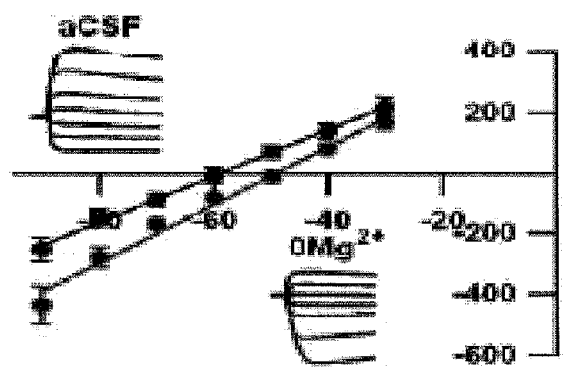
E
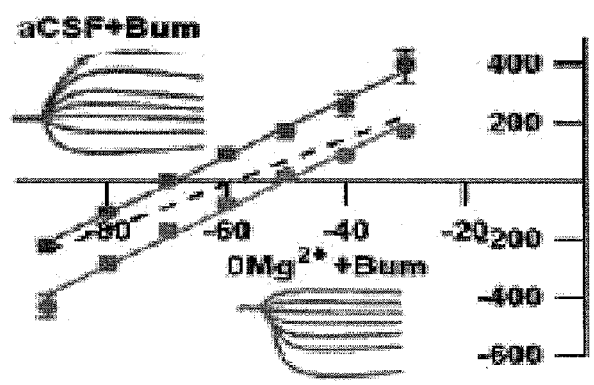
Figure 16 (cont'd)

F
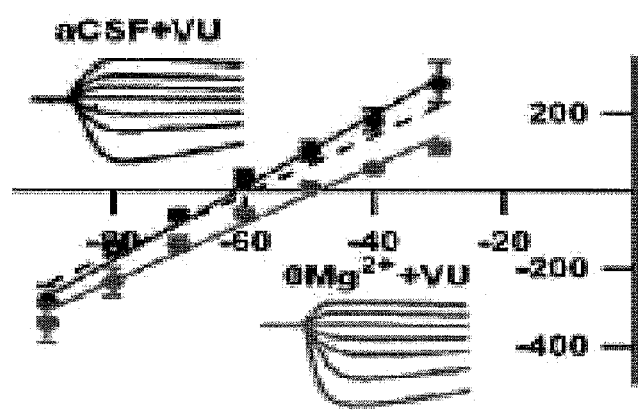
G
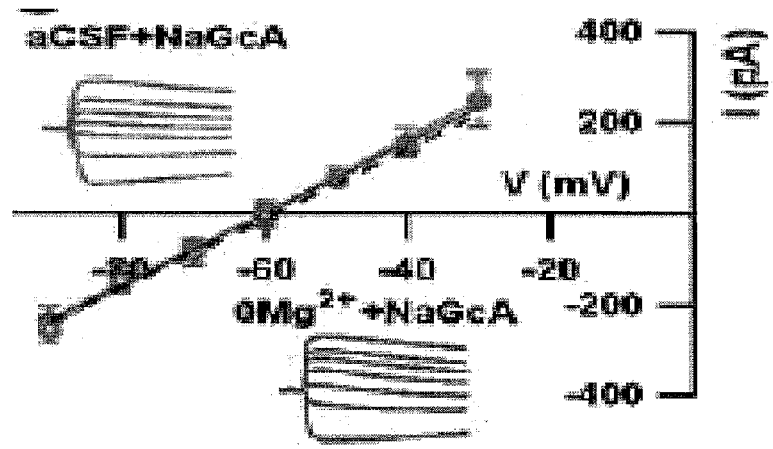
Figure 16 (cont'd)

H
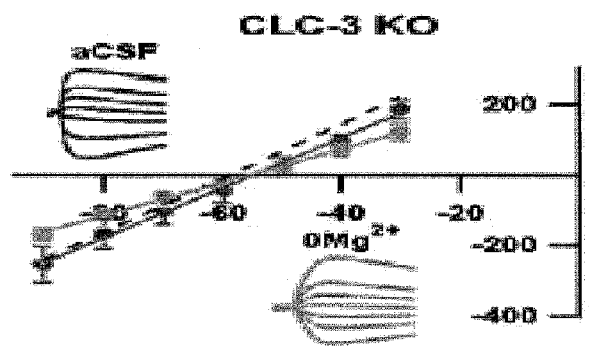
I
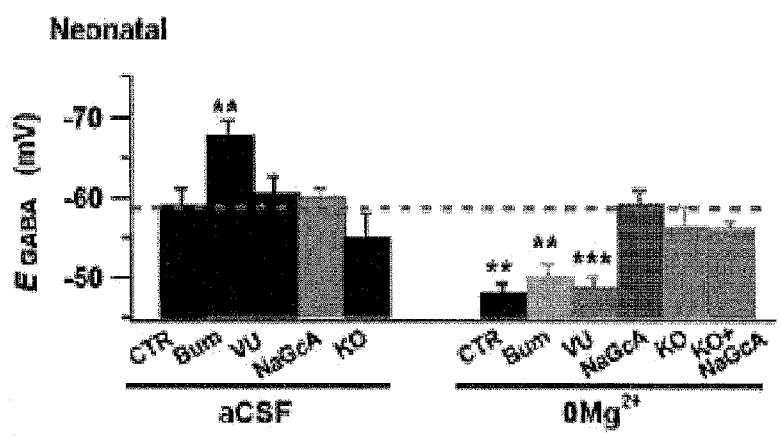
Figure 16 (cont'd)

J
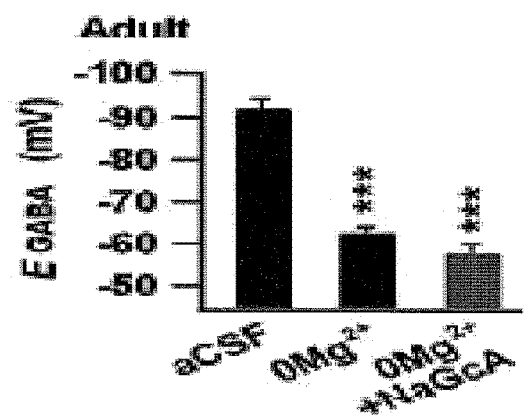
K
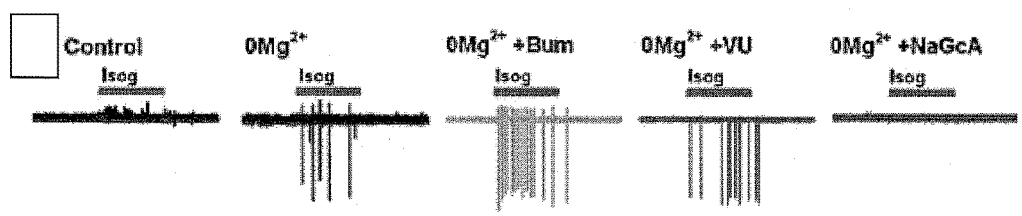
L
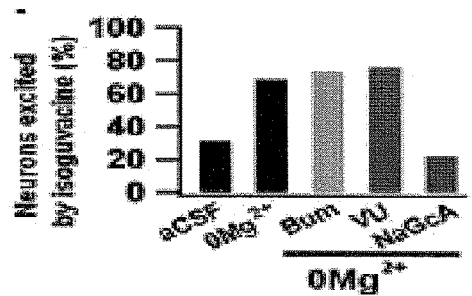
Figure 16 (cont'd)

GLUCONATE-BASED COMPOSITIONS AS A NEONATE ANTICONVULSANT

STATEMENT OF GOVERNMENT SUPPORT

This invention was made with government support under Grant Nos. MH083911 and AG045656, awarded by The National Institutes of Health. The Government has certain rights in the invention.

FIELD OF THE INVENTION

The present invention is related to the field of neurological disorders. In particular, the prevention and treatment of convulsive disorders including, but not limited to, muscular tonic/clonic convulsions, epilepsy, Jacksonian disorders and/or involuntary tremors. For example, some embodiments are directed to treating and preventing convulsive disorders in neonates and/or infants. Gluconate-based compositions have been found to be selectively effective in treating and/or preventing convulsive disorders in neonates and/or infants.

BACKGROUND

The incidence of epilepsy is highest in the first year of life with a reported incidence around 1.8-3.5/1,000 live births in the United States. Silverstein et al., "Neonatal seizures" *Annals Of Neurology* 62:112-120 (2007); and Jensen F., "Neonatal seizures: An update on mechanisms and management" *Clinics In Perinatology* 36:881-900 (2009). Although many antiepileptic drugs (AEDs) have been developed over the past several decades, neonatal seizures are often refractory to current AEDs, which are more effective in older children or adults. Painter et al., "Phenobarbital compared with phenytoin for the treatment of neonatal seizures" *The New England Journal Of Medicine* 341:485-489 (1999); van Rooij et al., "Treatment of neonatal seizures" *Seminars In Fetal & Neonatal Medicine* 18:209-215 (2013); and Dzhala et al., "NKCC1 transporter facilitates seizures in the developing brain" *Nature Medicine* 11:1205-1213 (2005).

In some cases, even after AED application, electroencephalographic (EEG) recordings show ongoing cortical epileptic activity in neonates, which may impair cognitive development and later result in epilepsy. Connell et al., "Clinical and EEG response to anticonvulsants in neonatal seizures" *Archives Of Disease In Childhood* 64:459-464 (1989); Glykys et al., "Differences in cortical versus subcortical GABAergic signaling: a candidate mechanism of electroclinical uncoupling of neonatal seizures" *Neuron* 63:657-672 (2009); and Puskarjov et al., "Pharmacotherapeutic targeting of cation-chloride cotransporters in neonatal seizures" *Epilepsia* 55:806-818 (2014).

Epileptic seizures are often caused by overexcitation of the brain circuits, which can be inhibited by boosting $GABA_A$ receptors ($GABA_A$-Rs), the major inhibitory receptors in the adult brain. Accordingly, AEDs are often developed to increase $GABA_A$-R function, such as benzodiazepine and barbiturate drugs. Bialer, M. & White, H. S. Key factors in the discovery and development of new antiepileptic drugs. *Nature reviews. Drug discovery* 9, 68-82 (2010). However, while $GABA_A$-Rs are mostly inhibitory in the adult brain, they are excitatory in the developing brain. Chen, G., Trombley, P. Q. & van den Pol, A. N. Excitatory actions of GABA in developing rat hypothalamic neurones. *The Journal of physiology* 494 (Pt 2), 451-464 (1996); and Ben-Ari, Y. Excitatory actions of gaba during development: the nature of the nurture. *Nature reviews. Neuroscience* 3, 728-739 (2002).

The excitatory GABAergic transmission in the developing brain also explains why GABA agonists are often ineffective in controlling neonatal seizures, and sometimes can even exacerbate neonatal seizure activity. Farwell, J. R., et al. Phenobarbital for febrile seizures—effects on intelligence and on seizure recurrence. *The New England journal of medicine* 322, 364-369 (1990).

Classically, GABA excitatory versus inhibitory function has been attributed to the regulation by Cl⁻ co-transporters NKCC1 and KCC2. 10. Kaila, K., Price, T. J., Payne, J. A., Puskarjov, M. & Voipio, J. Cation-chloride cotransporters in neuronal development, plasticity and disease. *Nature reviews. Neuroscience* 15, 637-654 (2014). Blaesse, P., Airaksinen, M. S., Rivera, C. & Kaila, K. Cation-chloride cotransporters and neuronal function. *Neuron* 61, 820-838 (2009). Previous study found that NKCC1 might facilitate neonatal seizures in rodent animals[12], but recent clinical trial in infant babies found severe side effect of NKCC1 blocker bumetanide and very limited effect in treating neonatal seizure[13]. Dzhala, V. I., et al. NKCC1 transporter facilitates seizures in the developing brain. *Nature medicine* 11, 1205-1213 (2005); and Pressler, R. M., et al. Bumetanide for the treatment of seizures in newborn babies with hypoxic ischaemic encephalopathy (NEMO): an open-label, dose finding, and feasibility phase ½ trial. *Lancet Neurol* 14, 469-477 (2015).

Unfortunately, to date there have been no effective drugs that can treat neonatal seizures successfully, prompting an urgent search of new drugs for neonatal epilepsy. What is needed in the art is a simple, effective and safe anti-epileptic drug to treat the unique characteristics of neonatal seizure.

SUMMARY OF THE INVENTION

The present invention is related to the field of neurological disorders. In particular, the prevention and treatment of convulsive disorders including, but not limited to, muscular tonic/clonic convulsions, epilepsy, Jacksonian disorders and/or involuntary tremors. For example, some embodiments are directed to treating and preventing convulsive disorders in neonates and/or infants. Gluconate-based compositions have been found to be selectively effective in treating and/or preventing convulsive disorders in neonates and/or infants.

In one embodiment, the present invention contemplates a method, comprising: a) providing: i) a neonatal patient exhibiting convulsions, wherein said patient is not in need of a divalent cation-based therapy; ii) a composition comprising a gluconate complex; and b) administering said composition to said patient under conditions such that said convulsions are reduced. In one embodiment, the gluconate complex lacks a divalent cation. In one embodiment, the gluconate complex is sodium gluconate. In one embodiment, the divalent cation-based therapy is a calcium-based therapy. In one embodiment, the divalent cation-based therapy is a magnesium-based therapy. In one embodiment, the divalent cation-based therapy is a zinc-based therapy. In one embodiment, the gluconate complex comprises a gluconic acid derivative.

In one embodiment, the present invention contemplates a method, comprising: a) providing: i) a neonatal patient exhibiting convulsions, wherein said patient is not in need of a divalent cation-based therapy; ii) a composition consisting of a gluconate complex, wherein said complex lacks a divalent cation; and b) administering said composition to said patient under conditions such that said convulsions are reduced. In one embodiment, the gluconate complex is sodium gluconate. In one embodiment, the divalent cation-based therapy is a calcium-based therapy. In one embodiment, the divalent cation-based therapy is a magnesium-based therapy. In one embodiment, the divalent cation-based therapy is a zinc-based therapy. In one embodiment, the gluconate complex comprises a gluconic acid derivative.

In one embodiment, the present invention contemplates a composition comprising a gluconate derivative wherein at least one hydroxyl moiety or carboxylic acid moiety is substituted with a group including, but not limited to, a substituted or unsubstituted aryl or heteroaryls, an unsubstituted or substituted C1-C6-alkyl group, a substituted or unsubstituted 5-6-membered saturated or unsaturated fused ring, a substituted or unsubstituted 5-6-membered saturated or non-saturated ring, natural amino acid residues or synthetic amino acid residues, trihalomethyl, substituted or unsubstituted C1-C6-alkoxy, $NH_2$, SH, thioalkyl, aminoacyl, aminocarbonyl, substituted or unsubstituted C1-C6-alkoxycarbonyl, aryl, heteroaryl, substituted or unsubstituted 4-8-membered cyclic alkyl, optionally containing 1-3 heteroatoms, carboxyl, cyano, halogen, hydroxy, nitro, acetoxy, aminoacyl, sulfoxy, sulfonyl, C1-C6-thioalkoxy, C1-C6-aliphatic alkyl, substituted or unsubstituted saturated cyclic C4-C8-alkyl optionally containing 1-3 heteroatoms and optionally fused with an aryl or an heteroaryl; a substituted or unsubstituted aryl, substituted or unsubstituted heteroaryl, whereby said aryl or heteroaryl groups are optionally substituted with substituted or unsubstituted C1-C6-alkyl, like trihalomethyl, substituted or unsubstituted C1-C6-alkoxy, substituted or unsubstituted C2-C6-alkenyl, substituted or unsubstituted C2-C6-alkynyl, amino, aminoacyl, aminocarbonyl, substituted or unsubstituted C1-C6-alkoxycarbonyl, aryl, carboxyl, cyano, halogen, hydroxy, nitro, acetoxy, aminoacyl, sulfoxy, sulfonyl, C1-C6-thioalkoxy; or R5 and R6 taken together could form a substituted or unsubstituted 4-8-membered saturated cyclic alkyl or heteroalkyl group.

In one embodiment, the present invention contemplates a method comprising: a) providing; i) a neonatal patient exhibiting convulsions, wherein said patient comprises at least one chloride ion channel; ii) a composition comprising a chloride ion channel blocker; and b) administering said composition to said patient under conditions such that said convulsions are reduced. In one embodiment, the chloride ion channel blocker is a gluconate complex that lacks a divalent cation. In one embodiment, the chloride ion channel blocker includes, but is not limited to, niflumic acid (NFA), flufenamic acid, 4,4'-Diisothiocyanato-2,2'-stilbenedisulfonic acid disodium salt (DIDS), and 5-Nitro-2-(3-phenylpropylamino) benzoic acid (NPPB). In one embodiment, the gluconate complex is sodium gluconate. In one embodiment, the patient is not in need of a divalent-cation based therapy. In one embodiment, the divalent cation-based therapy is a calcium-based therapy. In one embodiment, the divalent cation-based therapy is a magnesium-based therapy. In one embodiment, the divalent cation-based therapy is a zinc-based therapy. In one embodiment, the gluconate complex comprises a gluconic acid derivative.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "gluconic acid" or "gluconate" as used herein, refers to a six α-carbon chain comprising five hydroxyl moieties and on carboxylic acid moiety. Each of the hydroxyl and carboxylic acid moieties may be substituted and/or derivatized as disclosed herein to provide anti-convulsant gluconate derivatives that have improved clinical effectiveness as compared to traditional divalent cation therapies.

The term "convulsion" or "seizure" as used herein, refers to any abnormal violent and involuntary contraction or series of contractions of the muscles and/or physical manifestations including, but not limited to, convulsions, sensory disturbances, and/or loss of consciousness, resulting from abnormal electrical discharges in the brain.

The term "neonate" or "neonatal" as used herein, refers to any new born infant, generally less than one month old. Generally, reference to neonate age is characterized by "P#", where "P" refers to postnatal, and "#" indicates days-old, where PO is the day of birth.

The term "divalent cation" refers to any ion carrying a valence charge of positive two (e.g., 2+). For example, the ions $Ca^{2+}$, $Mg^{2+}$ and/or $Zn^{2+}$ are considered to be divalent cations.

The term "about" as used herein, in the context of any of any assay measurements refers to +/−5% of a given measurement.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "medium" as used herein, refers to any material, or combination of materials, which serve as a carrier or vehicle for delivering of a drug to a treatment point (e.g., wound, surgical site etc.). For all practical purposes, therefore, the term "medium" is considered synonymous with the term "carrier". It should be recognized by those having skill in the art that a medium comprises a carrier, wherein said carrier is attached to a drug or drug and said medium facilitates delivery of said carrier to a treatment point. Further, a carrier may comprise an attached drug wherein said carrier facilitates delivery of said drug to a treatment point. Preferably, a medium is selected from the group including, but not limited to, foams, gels (including, but not limited to, hydrogels), xerogels, microparticles (i.e., microspheres, liposomes, microcapsules etc.), bioadhesives, or liquids. Specifically contemplated by the present invention is a medium comprising combinations of microparticles with hydrogels, bioadhesives, foams or liquids. Preferably, hydrogels, bioadhesives and foams comprise any one, or a combination of, polymers contemplated herein. Any medium contemplated by this invention may comprise a controlled release formulation. For example, in some cases a medium constitutes a drug delivery system that provides a controlled and sustained release of drugs over a period of time lasting approximately from 1 day to 6 months.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, intravenous injection, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., neonates, infants and/or children). It is not intended that the term "patient" connote a need for medical treatment, therefore, a patient may voluntarily or involuntarily be part of experimentation whether clinical or in support of basic science studies.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frame-shift mutation). Complementation is achieved by transfecting cells which lack protein activity with an expression vector which expresses the protein, a derivative thereof, or a portion thereof.

The term "transfection" or "transfected" refers to the introduction of foreign DNA into a cell.

The term "bind" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That is typical when the binding component is an enzyme and the analyte is a substrate for the enzyme. Reactions resulting from contact between the binding agent and the analyte are also within the definition of binding for the purposes of the present invention.

BRIEF DESCRIPTION OF THE FIGURES

FIG. 1 presents exemplary data showing anti-burst activity of gluconate on cultured neurons. Data are presented as mean±s.e.m., *$P<0.05$, $P<0.01$, *$P<0.001$.

FIG. 1A: Spontaneous burst action potentials in cultured neurons was stopped immediately by application of 20 mM NaGcA (n=10, from 3 batches), the extended graphs of before, during and after NaGcA application was shown in the bottom.

FIG. 1B: CTZ induced robust burst activity in cultured neurons (up) and it was completely blocked by 10 mM NaGcA (bottom).

FIG. 1C: Dose-dependent inhibition of NaGcA on CTZ induced burst activity. Black bar indicates burst frequency and gray bar indicates burst duration (n=11 form 4 batches, paired student t-test).

FIG. 1D: Representative trace of kainic acid (1 μM for 2 hrs) induced robust burst activity (up) and it was also dramatically suppressed by 10 mM NaGcA (bottom).

FIG. 1E: Dose-dependent response of KA induced burst activity to NaGcA (n=12 from 3 bathes, paired student t-test).

FIG. 1F: Typical trace of 4-AP (50 μM for 2 hrs) induced robust activity (up) also was obviously suppressed by 10 mM NaGcA (bottom).

FIG. 1G: Dose response of 4-AP induced burst activity to NaGcA (n=9 from 3 bathes, paired student t-test).

FIG. 1H: Representative traces shown the typical recurrent epileptiform burst induced by 10 μM CTZ (Top), and lack of burst activity in co-application of CTZ and NaGcA (10 mM).

FIG. 1J: Live/dead assay images showed calcein-AM (green for live) and ethidium homodimer-1 (red for dead) in different groups. Scale bar, 100 μm.

FIG. 1K: Quantification of cell live/dead assay. Results revealed that NaGcA has neuron protection function of against kainic acid induced neuronal excitotoxicity, and itself without any side effect on neuron survival.

Figure 1I:
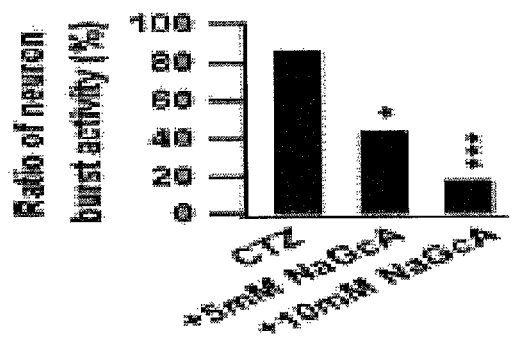
FIG. 1I(a-c): Quantified data of panel h showed that both 5 and 10 mM NaGcA chronic co-treatment, it significantly reduced the ratio of neurons showing burst activity (FIG. 1I(a), $\chi^2$ test), burst frequency (FIG. 1I(b), oneway ANOVA) and burst duration (FIG. 1I(c) and FIG. 1I(b), one-way ANOVA). n=22 for CTZ, n=16 for CTZ+5 mM NaGcA and n=17 for CTZ+10 mM NaGcA, all data were got from 5 batches, paired student t-test.
Figure 1I:
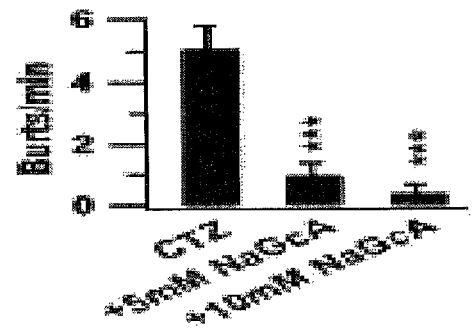
Figure 1I:
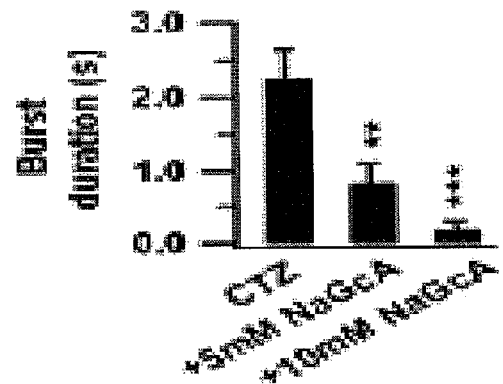
Figures 2A, 2N:
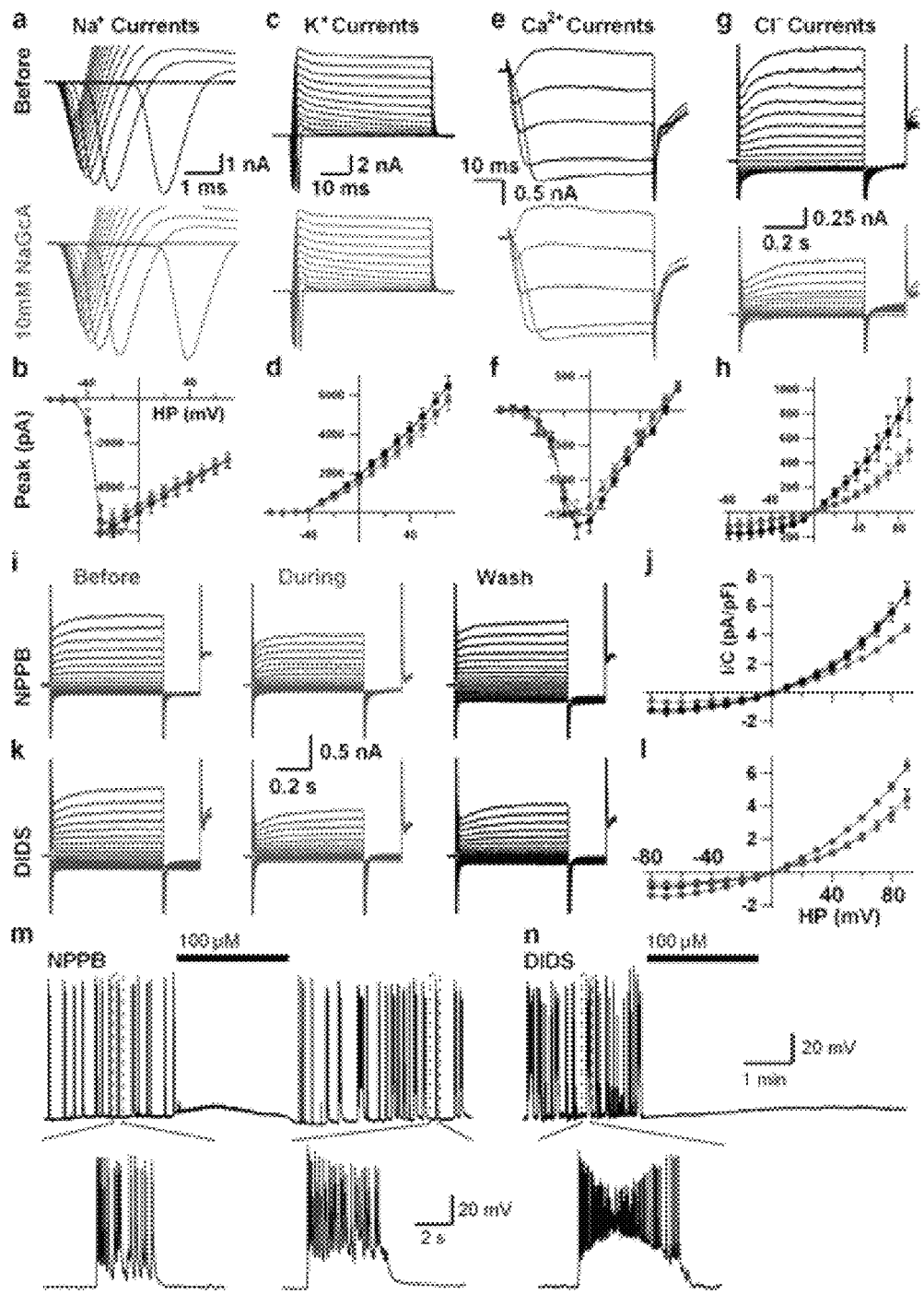
FIG. 2 presents exemplary data that gluconate inhibits chloride currents in cultured cortical neurons. Data are shown as mean±s.e.m.

(a-f) NaGcA (10 mM) had no effect on Na+ currents (a,b), K+ currents (c,d), or Ca2+ currents (e, f).

(g) Typical Cl− currents recorded before (black) and after 10 mM NaGcA application (green).

(h) I-V curves showing a significant NaGcA inhibition on the Cl− currents (n=7 from 3 batches of cultures, paired Student's t-test).

(i,j) NPPB (100 μM), a classical Cl− channel blocker, inhibited the Cl− currents in cultured cortical neurons.

(k,l) The inhibitory effect of another common Cl− channel blocker DIDS (100 μM) on the Cl− currents in cultured cortical neurons. Note the persistent inhibition of DIDS on the Cl− currents after washing off DIDS. (m,n) Both NPPB (m) and DIDS (n) potently inhibited the epileptiform activity induced by CTZ, supporting that Cl− channels are involved in epileptogenesis.

FIG. 3 illustrates exemplary data showing an age-dependent effect of gluconate on epileptic activity in hippocampal slices. Data are shown as mean±s.e.m.

(a) Extracellular field potential recordings in the CA3 pyramidal cell layer in hippocampal slice of the neonatal (P7) mouse. Epileptic events was induced by Mg2+ free aCSF and inhibited in presence of 20 mM NaGcA in Mg2+ free aCSF. Expanded traces of before, during and after application of NaGcA were shown on the bottom.

(b) Power spectra of epileptic activity in 5-minute time windows before, during and after NaGcA application. The amplitude of power (integrative area under the spectrum trace) was dramatically suppressed after NaGcA application.

(c,d) The comparable efficacy of anti epileptiform activity of NaGcA was examined in P12 hippocampal slice.

(e) NaGcA has moderate anti-epileptic discharges effect in P26 hippocampal slice comparing to neonatal slices. Bottom showed the extended traces of before, during and after NaGcA perfuse. (f) Power amplitude was slightly decreased during NaGcA application and almost recovered after wash out NaGcA.

(g) Normalized power of epileptic activity was induced by 0 Mg2+ aCSF in consecutive 5 min windows of before, during and after NaGcA application. NaGcA dramatically reduced the power of epileptic activity in P6-8 and P10-12 groups but less effect on P21-33 group, and the control group data showed that there was no significantly change after extra 20 mM NaCl was added into 0 Mg2+ aCSF during 80 min extracellular field potential recording.

FIG. 4 presents exemplary data showing anti-epileptic activity of NaGcA was tested in different neonatal slice seizure models. Data are shown as mean±s.e.m.

(a) Extracellular field potential recordings in the CA3 pyramidal cell layer, epileptic activity was induced by 50 μM 4-AP. NaGcA attenuated seizure-like discharges in response to 50 μM 4-AP. The respective trace was enlarged in the bottom.

(b) Power spectra of epileptic activity in 5 minutes windows of before, during and after NaGcA application. The amplitude of power spectra was significantly suppressed after NaGcA application.

(c) Averaged power of epileptic activity, which induced by 4-AP, was obviously reduced by perfuse of NaGcA.

(d) NaGcA remarkably suppressed the burst activity in neonatal high K+ model. Bottom showed the expanded views of before, during and after NaGcA perfuse.

(e) Power spectra amplitude was significantly reduced during NaGcA application.

(f) Normalized power of epileptic activity was induced by high K+ aCSF in consecutive 5 min windows before, during and after NaGcA application. NaGcA dramatically decreased the power of high K+ induced epileptic activity.

FIG. 5 presents exemplary data showing CLC-3 channel mediated Cl− current in CA3 pyramidal neuron was inhibited by gluconate. Values are mean±s.e.m.

(a) Representative Cl− currents in CA3 pyramidal neuron. The Cl− currents was remarkably inhibited by 20 mM NaGcA application (green).

(b) I-V curves plotted significant outward rectification with the reversal potential close to 0 mV. Cl− current was dramatically reduced in present of NaGcA (green).

(c) Example Cl− current traces got from CA3 pyramidal neurons which use normal CsCl pipette solution (left red), intracellular dialysis (10 min) with anti-ClC-3 antibody (middle orange) or control rabbit IgG (right black).

(d) I-V plot showed remarkable reduction after anti-ClC-3 antibody dialysis (orange) but no significant change after control IgG dialysis (black).

(e) Immunostaining images of HEK293T cell transfected with either the eGFP (Left row) or ClC-3-eGFP fusion protein plasmid (Right Row). ClC-3 immunoreactivity (red) was detected strongly in ClC-3-eGFP transfected cells (arrows) but not in non-transfected or eGFP transfected cells. Scale bar, 40 μm.

(f) Typical Cl− current in HEK cell transfected with either eGFP (top) or ClC-3-eGFP plasmid (bottom), and the response to the 20 mM NaGcA (middle green).

(g) I-V relationships of before, during and wash out NaGcA for ClC-3-eGFP (right, n=7 from two batches) infected cells, ClC-3 mediated current was significantly inhibited by NaGcA.

FIG. 6 presents exemplary data showing that CLC-3 was up-regulated in neonatal epileptic slices. Data are presented as mean±s.e.m., ***$P<0.001$.

(a) Comparable expression level of ClC-3 on hippocampal CA3, ClC-3 immunoreactivity was increased after slice incubation in 0 Mg2+ aCSF for 1 hr. Asterisk indicated an enlarged typical neuron with CLC-3 immuno-signal (red) overlapped with phase in CA3 area. Scale bar=20 μm (5 μm in enlarged images).

(b) Quantified data of ClC-3 immunoreactivity intensity showed significant increase after the slice incubation in 0 Mg2+ aCSF for 1 hr (n=10 slices from 4 pups for control, n=11 slices from 4 pups for 0 Mg2+, student's t-test).

(c) Western blot of hippocampal ClC-3 protein from control and 0 Mg2+ aCSF (1 hr) treated slice.

(d) Quantified data showed significant increase of CLC-3 protein after hippocampal slices treated with 0 Mg2+ aCSF (n=6 pups for each of group, student's t-test).

(e) Representative Cl− currents traces of control, Mg2+ incubation for 1 hr and Mg2+ incubation for 1 hr then recorded in 20 mM NaGcA.

(f) Averaged I-V plot of Cl− currents showed significant increase in 0 Mg2+ group and it was also remarkably inhibited by NaGcA.

Figure 7E:
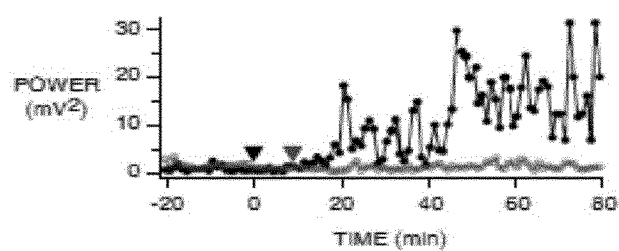
Figure 7F:
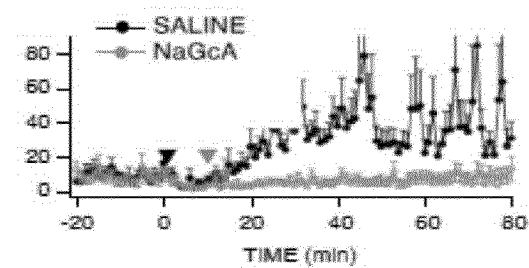
Figure 7G:
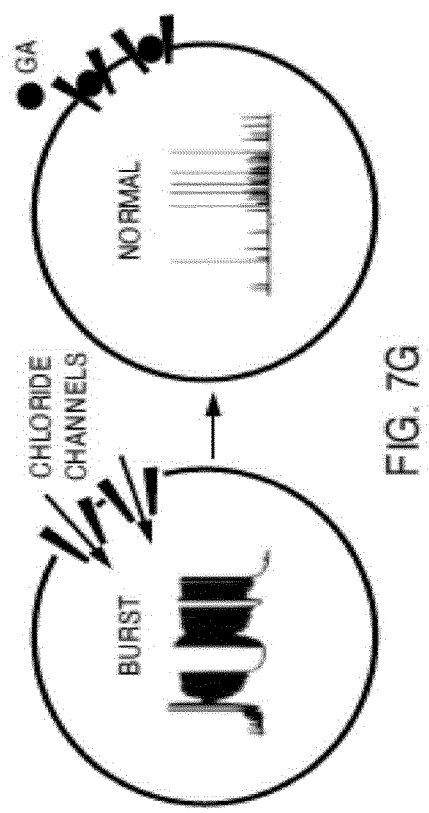

FIG. 7 presents exemplary data showing that gluconate is an effective therapy for KA induced neonatal seizure.

(a) Representative EEG trace from P12 rat, which injected with saline (0.1 ml/10 g, i.p.) 10 min after KA injection (2 mg/kg, i.p.), showed recurrent epileptic burst discharges.

(b) Extended view of a single cluster-like epileptic discharges from the box in a.

(c) Typical traces of interictal, ictal-tonic and ictal-clonic expended form the box in b.

(d) Example EEG of P12 rat, which injected with NaGcA (2 g/kg, ip) 10 min after KA injection (2 mg/kg, i.p.), showing increase in spike activity but no robust burst discharges was developed after NaGcA administration. Scale bar same as a.

(e) Enlarged area of the box in d. Scale bar same as b.

(f) A single spike discharge was observed in the expended trace from e (box area). Scale bar same as c.

(g) Individual EEG power in 1 min time window of panel a (black) and d (green).

(h) Group averaged EEG power in 1 min time window of saline (black, P10-12, n=11) and NaGcA administration (green, P10-12, n=11). The black arrowhead indicates the KA injection point, the red arrowhead indicates either saline or NaGcA injection point. The average power of epileptic activity induced by KA injection was 70% lower in the presence of NaGcA.

(i) Work model of our study. Cl− influx through chloride channels will facilitate synchronized network activity (left). But this process is suppressed by gluconic acid (GA) due to its inhibition on chloride channels (right).

FIG. 8 presents exemplary data showing the effect of gluconate on adult epilepsy.

(a-c) Representative EEG recordings showing epileptiform activity induced by injection of pentylenetetrazol (PTZ) (50 mg/kg, i.p.) followed by saline (a), NaGcA at 1 g/kg (b), or NaGcA at 2 g/kg (c). Open triangles indicate the first spike, and the black small arrows indicate the first burst.

(d,e) Bar graphs showing the dose-dependent effect of NaGcA in prolonging the latency of epileptiform spikes (d) or epileptiform bursts (e) induced by PTZ (50 mg/kg, i.p.).

(f) Bar graphs showing a mild inhibitory effect of NaGcA on the behavioral seizure score induced by PTZ (50 mg/kg, i.p.).

(g) Bar graphs showing that NaGcA dose-dependently prolonged the latency of seizure behavior (Racine score 3 and above).

Figure 9:
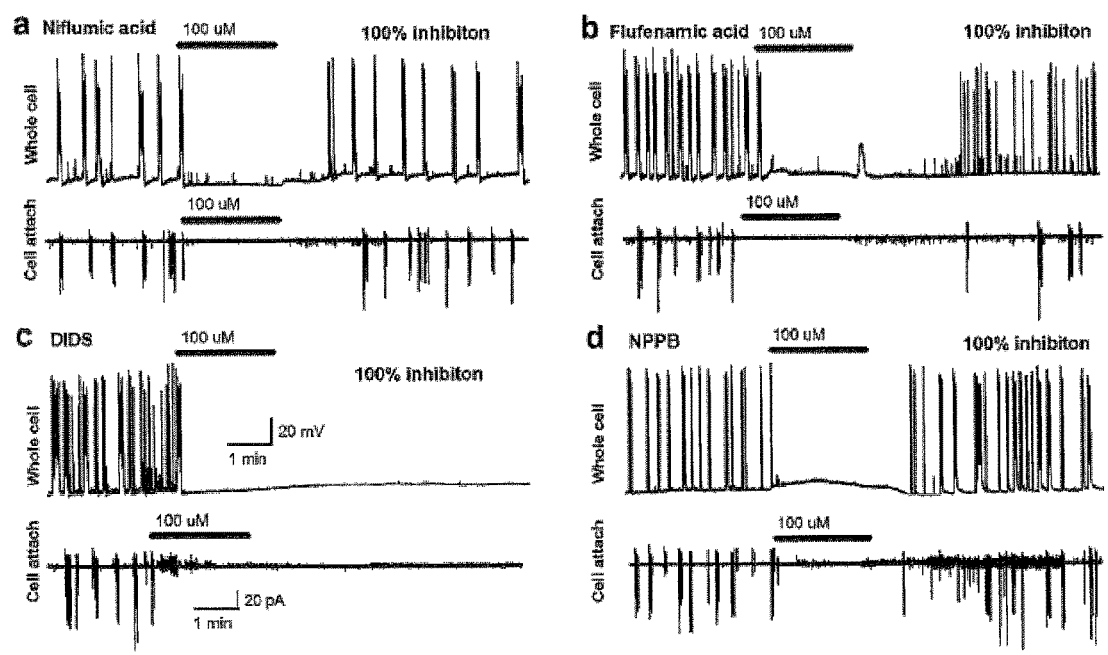

FIG. 9 presents exemplary data showing the effects of a variety of chloride ion channel inhibitors:
(a) Niflumic acid (NFA) (100 μM)
(b) Flufenamic acid (100 μM)
(c) DIDS (100 μM)
(d) NPPB (100 μM)

Figure 10:
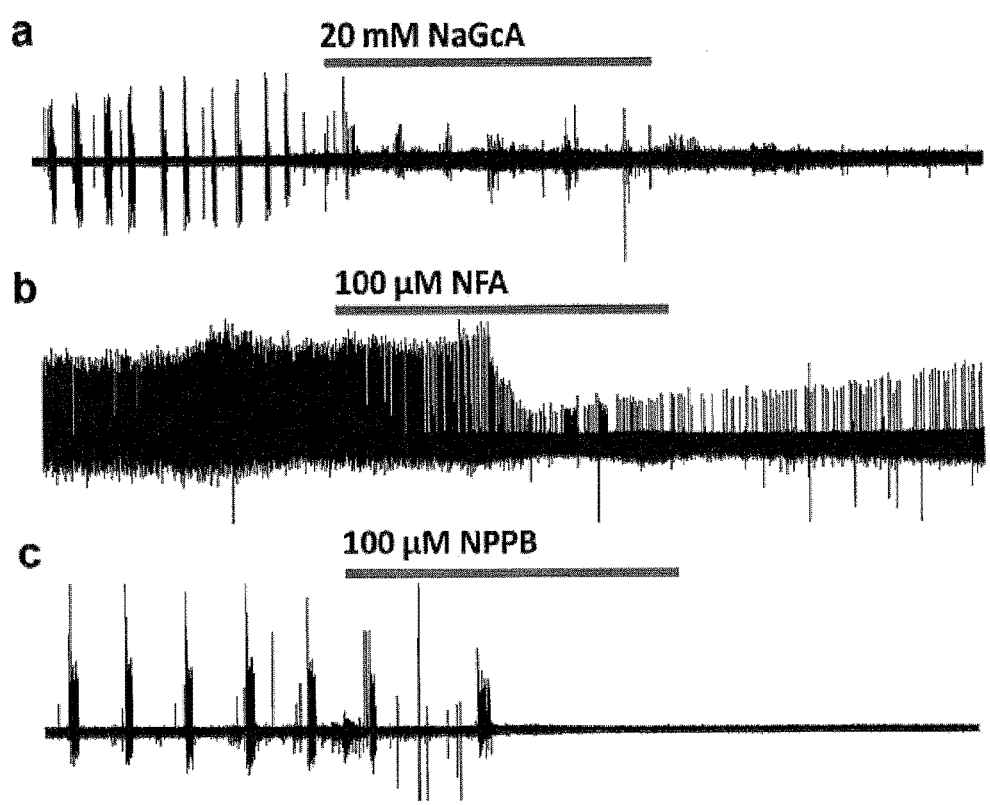

FIG. 10 presents exemplary data showing the effects of a variety of chloride ion channel inhibitors on epileptic activity in neonatal hippocampal slices:
(a) Sodium Gluconic Acid (20 mM) (NaGcA)
(b) NFA (100 μm)
(c) NPPB (100 μm)

FIG. 11 presents exemplary data showing a developmental change of CLC-3 channel-mediated Cl− currents.

FIG. 11A: Representative Cl− currents recorded in CA3 pyramidal neurons from mouse hippocampal slices obtained at different ages of animals (top row, black traces). Green traces in the middle row show Cl− currents after inhibition by 20 mM NaGcA. The bottom row shows the I-V curves of Cl− currents in control and after NaGcA treatment in different ages of mice.

FIG. 11B: Quantified Cl− current density in control (black) or after NaGcA treatment (green) (HP=+90 mV). Note a significant decrease of Cl− current density in adult animals. ***$P<0.001$.

FIG. 11C: Dose response curve of NaGcA inhibition on Cl− currents.

FIG. 11D: Typical Cl− current traces recorded under control (black), anti-CLC-3 antibody (orange), or pre-absorbed control antibody (grey). I-V curves showing a remarkable reduction of the Cl− currents after anti-CLC-3 antibody dialysis (orange).

FIG. 11E: Immunostaining confirming the lack of CLC-3 signal in CLC-3 knockout mice. Scale bar, 10 μm.

FIG. 11F: The voltage-dependent outward rectifying Cl− currents was largely absent in CLC-3 KO mice, supporting that CLC-3 channels mediate the Cl− currents.

FIG. 11G: I-V curve showing little inhibition of NaGcA on the remaining small Cl− currents in CLC-3 KO mice, supporting that NaGcA is an inhibitor of CLC-3 channels.

FIG. 11H: Expression of CLC-3 Cl− channels in HEK293T cells. Scale bar, 40 μm.

FIG. 11I: Large Cl− currents recorded from HEK293T cells expressing CLC-3 channels (bottom row). Application of 20 mM NaGcA significantly inhibited the CLC-3 channel-mediated Cl− currents (green traces).

FIG. 11J: I-V curves showing the NaGcA inhibition of CLC-3 channel-mediated Cl− currents (CLC-3, 925±124 pA, n=7; CLC-3+ NaGcA, 544±59 pA, n=7; P<0.004, paired t-test; HP=+90 mV). Values are mean+s.e.m.

FIG. 12 presents exemplary data showing the relationship between CLC-3 chloride channels and neonatal epileptogenesis.

FIG. 12A: Upregulation of CLC-3 channel expression (red) in hippocampal CA3 neurons after induction of epileptiform activity in 0 $Mg^{2+}$ artificial cerebrospinal fluid (aCSF) (1 hr). Scale bar=5 μm.

FIG. 12B: Quantified CLC-3 immuno-intensity in control and 0 $Mg^{2+}$ aCSF (control, n=10 slices from 4 pups; 0 $Mg^{2+}$, n=11 slices from 4 pups; p<0.05, Student's t-test).

FIGS. 12C and 12D: Western blot analysis also showed a significant increase of CLC-3 protein level in the hippocampus after treatment with 0 $Mg^{2+}$ aCSF (n=6 pups for both groups, p<0.001, Student's t-test).

FIG. 12E: Representative voltage-dependent Cl− current traces in control, 0 $Mg^{2+}$ (1 hr), and 0 $Mg^{2+}$+20 mM NaGcA (1 hr) conditions.

FIG. 12F: I-V curves showing a significant increase of outward rectifying Cl− currents in 0 $Mg^{2+}$ aCSF group (red) and a remarkable inhibition by NaGcA (green).

FIG. 12G: Extracellular field potential recording showing epileptiform activity induced by 0 $Mg^{2+}$ aCSF and its strong inhibition by 20 mM NaGcA in the CA3 pyramidal layer in hippocampal slices of a neonatal mouse (postnatal day 7, P7).

FIG. 12H: Power spectra of epileptiform activity (5-minute time windows) before (red), during (green), and after (black) NaGcA application. The amplitude of power (integrative area under the power spectrum trace) was significantly reduced after NaGcA application.

FIGS. 12I and 12J: NaGcA also showed strong efficacy of anti-epileptiform activity in P12 hippocampal slices.

FIGS. 12K and 12L: In P26 hippocampal slices, however, NaGcA only showed modest effect on the epileptiform activity.

FIG. 12M: Normalized power showing the time course of NaGcA inhibition on the epileptiform activity induced by 0 $Mg^{2+}$ aCSF. NaGcA dramatically reduced the power of epileptiform activity in the P6-8 and P10-12 groups, but had much less inhibition in the P21-33 group. As a control, the grey line represents 20 mM NaCl effect on neonatal (P8-12) epileptiform activity.

FIGS. 12N and 12O: Representative traces of epileptiform activity induced by 0 $Mg^{2+}$ aCSF in hippocampal slices from WT, WT+20 mM NaGcA, and CLC-3 KO mice (all at P8-12). Note that epileptiform activity did not last for long time in CLC-3 KO mice.

FIG. 12P: Summarized data showing the burst latency (left panel) and burst frequency (right panel) induced by 0 $Mg^{2+}$ aCSF in hippocampal slices from WT, WT+20 mM NaGcA, and CLC-3 KO mice. Data are mean±s.e.m., *P<0.05, P<0.01, *P<0.001.

FIG. 13 presents exemplary data showing a broad anti-epileptic effect of NaGcA in various epilepsy models in neonatal hippocampal slices.

FIG. 13A: Extracellular field potential recording showing epileptic activity induced by 50 μM 4-AP in the CA3 pyramidal cell layer of neonatal hippocampal slices, and its inhibition by NaGcA (20 mM).

FIG. 13B: Power spectra of epileptic activity in 5-minute time windows before (red), during (green), and after (black) NaGcA application. Note that NaGcA (green) significantly reduced the power amplitude.

FIG. 13C: Normalized power showing the time course of the inhibition of NaGcA on the epileptic activity induced by 4-AP.

FIG. 13D: NaGcA (20 mM) remarkably suppressed the epileptiform activity in the high K+ epilepsy model in neonatal hippocampal slices.

FIG. 13E: Power spectra showing a significant reduction of epileptic activity during NaGcA application.

FIG. 13F: Normalized power illustrating the time course of NaGcA inhibition on the epileptic activity induced by high K+ aCSF.

The grey lines in FIGS. 13C and 13F represent the 20 mM NaCl control effect on neonatal (P8-12) epileptiform activity. Data are shown as mean±s.e.m.

Figure 14:
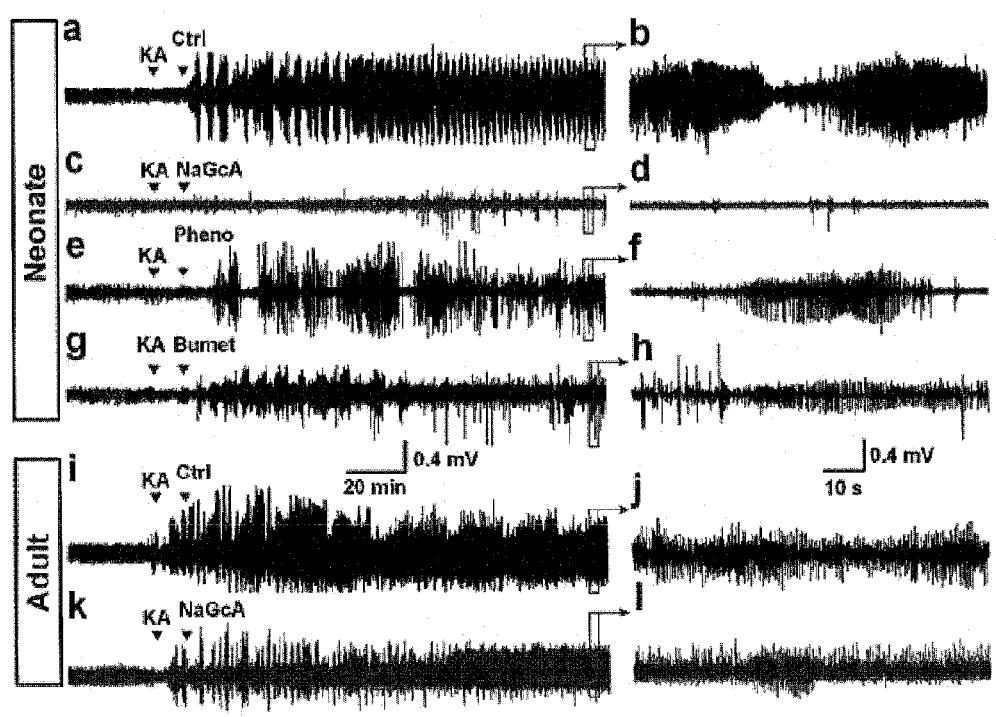

FIG. 14 presents exemplary data showing that the CLC-3 channel blocker gluconate potently inhibits neonatal seizure activity in vivo.

FIG. 14A: Representative EEG trace showing recurrent epileptic burst discharges from a P12 rat after KA injection (2 mg/kg, i.p.), which was followed by saline injection (0.1 ml/10 g, i.p.) with 10 min interval.

FIG. 14B: Expanded view of epileptic burst discharges from the box in FIG. 14A.

FIGS. 14C & 14D: Representative EEG trace (P12 rat) showing that NaGcA injection (2 g/kg, i.p.) at 10 min after KA injection (2 mg/kg, i.p.) significantly inhibited epileptic burst discharges.

FIGS. 14E & 14F: Representative EEG trace showing a modest effect of phenobarbital (25 mg/kg, i.p.) on epileptic burst activities in neonatal rat (P12).

FIGS. 14G & 14H: Representative EEG trace showing the effect of bumetanide (2 mg/kg, i.p.) on epileptic burst activities in neonatal rat (P12).

FIGS. 14I, 14J, 14K & 14L: In adult mice, KA injection (10 mg/kg, i.p.) also induced robust epileptic burst activities as shown in EEG recordings (14I and 14J), but NaGcA (2 g/kg, i.p.) only showed modest effect on KA-induced epileptic burst activities (14K and 14L).

FIG. 14M: Summarized data in neonatal animals showing the averaged EEG power (5-min time window) before and after KA injection, followed by injection of saline (black), NaGcA (green), phenobarbital (magenta), or bumetanide (blue). Note that NaGcA potently inhibited the power of EEG increase induced by KA.

FIG. 14N: In adult animals, NaGcA (green) modestly inhibited the power of EEG induced by KA.

In both FIGS. 14M and 14N, the black arrowhead indicates the KA injection, and the red arrowhead indicates drug injection. Data are mean±s.e.m.

Figure 15:
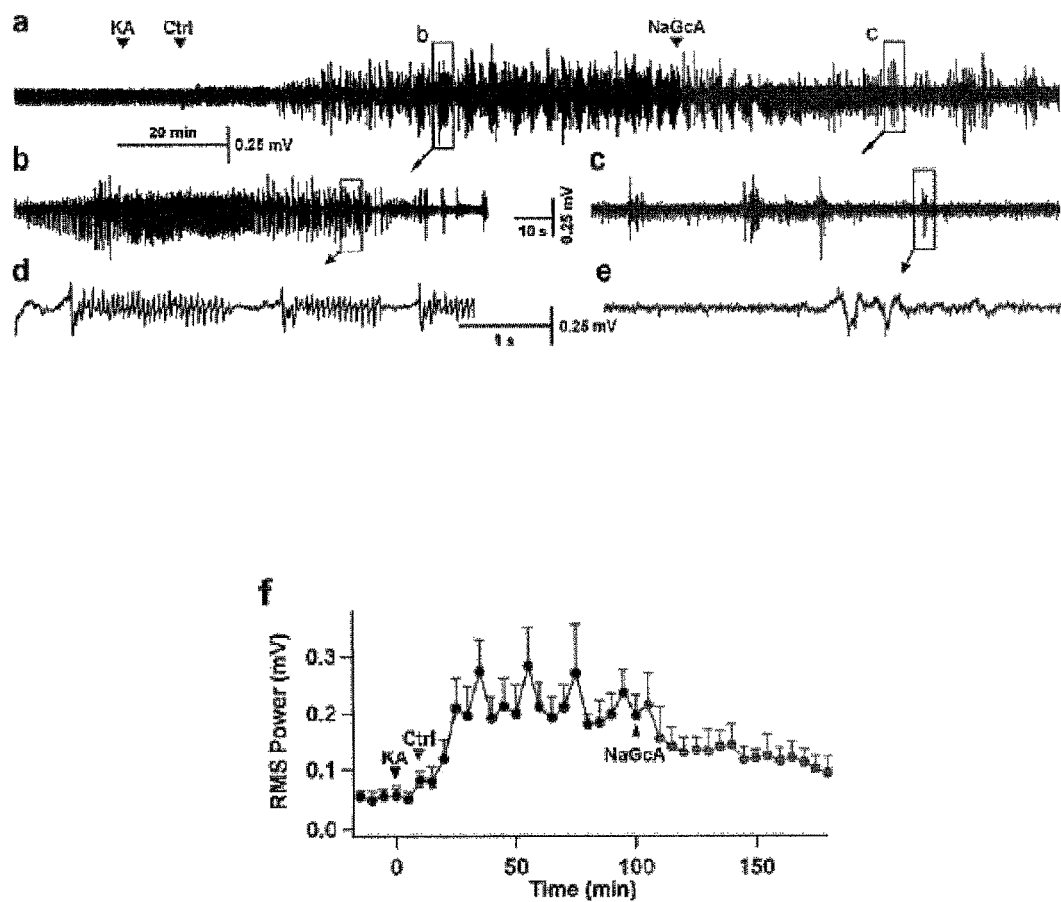

FIG. 15 presents exemplary data showing an acute effect of NaGcA on KA-induced epileptic activity in neonatal rats.

FIG. 15A: Typical epileptic EEG activity induced by KA through i.p. injection. After stable epileptic activity was recorded (~1 hr), NaGcA (2 g/kg, i.p.) was administrated to the rat (green). Note that the epileptic activity was gradually reduced after NaGcA injection.

FIG. 15B: Expanded trace from a segment in FIG. 15A, showing robust epileptic burst activity.

FIG. 15C: Expanded view of EEG recording after NaGcA injection in FIG. 15A.

FIG. 15D: Further expanded view of a segment in FIG. 15B, showing recurrent burst activity.

FIG. 15E: Further expanded view of EEG after NaGcA injection in FIG. 15C, showing significant inhibition of epileptic activity by NaGcA.

FIG. 15F: Summarized data showing the power of epileptic burst activity significantly reduced by NaGcA application (2 g/kg i.p., n=6, P10-12 rat, green). Data are mean±s.e.m.

FIG. 16 presents exemplary data showing that the activation of CLC-3 channels alters intracellular Cl− homeostasis in developing neurons.

FIG. 16A: Epileptiform burst activity induced by 0 $Mg^{2+}$ aCSF in the neonatal CA3 pyramidal neurons showed long-lasting membrane depolarization.

FIG. 16B: A long-lasting membrane depolarization pulse (40 mV, 10 s) mimicking the epileptiform burst activity significantly enhanced GABAA-R current induced by GABAA-R agonist isoguvacine (100 μM) under gramicidin-perforated whole cell recording. Such depolarization-induced enhancement was absent in CLC-3 KO mice and strongly inhibited by CLC-3 channel blocker NaGcA (20 mM).

FIG. 16C: Summarized data of the effect of membrane depolarization on GABAA-R current in WT, CLC-3 KO, and WT+ NaGcA groups.

FIG. 16D: Gramicidin-perforated recordings revealed a positive shift in the GABAA-R reversal potential (EGABA) in CA3 neurons after induction of epileptiform activity in 0 $Mg^{2+}$ aCSF.

FIG. 16E: Bath application of NKCC1 inhibitor bumetanide induced a negative shift in EGABA in normal aCSF, but did not abolish the positive shift of EGABA induced by 0 $Mg^{2+}$ aCSF.

FIG. 16F: KCC2 inhibitor VU0240551 had no effect on the EGABA under normal aCSF, and showed no effect on the positive shift induced by 0 $Mg^{2+}$ aCSF.

FIG. 16G: NaGcA completely abolishes the positive EGABA shift induced by 0 $Mg^{2+}$ aCSF. Gluconate itself did not affect the EGABA at all in normal aCSF.

FIG. 16H: In CLC-3 KO mice, EGABA also did not change when treated with 0 $Mg^{2+}$ aCSF.

FIG. 16I: Quantified data showing the EGABA changes under various conditions in neonatal CA3 pyramidal neurons (e.g., P8-9).

FIG. 16J: Bar graphs showing EGABA changes in adult CA3 pyramidal neurons. Note that NaGcA (20 mM) did not change the EGABA shift in adult animals.

FIG. 16K: Typical traces of cell-attached recording showing the spike activity induced by isoguvacine (10 μM, 30 s) in different groups in neonatal animals (e.g., P8-9).

FIG. 16L: Summarized data showing the percentage of neurons excited by isoguvacine. Note that NaGcA essentially abolished the GABA excitatory activity in 0 $Mg^{2+}$ aCSF. Data are shown as mean±s.e.m., *P<0.05, P<0.01, *P<0.001.

Figure 17:
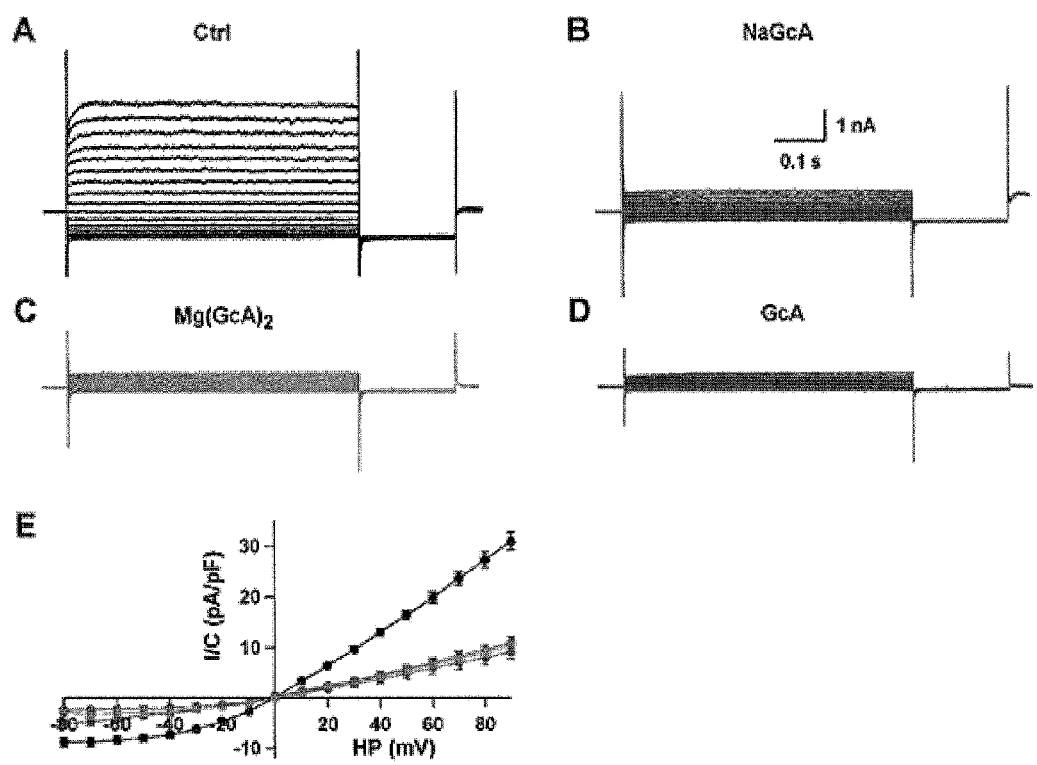

FIG. 17 presents exemplary data showing that gluconic acid complexed with various counter ions inhibit Cl− currents in P8-12 neonatal mice. Data are presented as mean±s.e.m.

FIG. 17A: Representative traces of out-rectifying Cl− currents in neonatal CA3 pyramidal neuron (black, n=12).

FIG. 17B: Typical traces of Cl− currents in presence of 20 mM NaGcA (green, n=7).

FIG. 17C: Typical traces of Cl− currents in presence of 10 mM $Mg(GcA)_2$.

FIG. 17D: Typical traces of Cl− currents in presence of 20 mM Gluconic acid (blue, n=6).

FIG. 17E: I-V plot showed remarkable reduction of Cl− currents density after bath application of gluconic acid and its salts.

DETAILED DESCRIPTION OF THE INVENTION

The present invention is related to the field of neurological disorders. In particular, the prevention and treatment of convulsive disorders including, but not limited to, muscular tonic/clonic convulsions, epilepsy, Jacksonian disorders and/or involuntary tremors. For example, some embodiments are directed to treating and preventing convulsive disorders in neonates and/or infants. Gluconate compositions have been found to be selectively effective in treating and/or preventing convulsive disorders in neonates and/or infants.

Neonatal seizure has been difficult to treat compared to adult epilepsy. In one embodiment, the present invention contemplates the use of an anti-epileptic drug, gluconate, which potently suppresses neonatal epilepsy by targeting at CLC-3 Cl− channels.

Gluconic acid is a large organic anion, often used as a food or drug additive in a salt form such as magnesium gluconate, calcium gluconate, or potassium gluconate, where gluconate was used to deliver ions. However, the functional role of gluconate itself was largely neglected in the past. The data presented herein shows that gluconic acid itself acts as a Cl− channel blocker and directly inhibits epileptiform activity. Furthermore, it is shown that gluconate is particularly effective for suppressing neonatal seizure, and its potency is superior to other currently available anti-epileptic drugs. Because gluconate is safe for human consumption, the compound represents a new platform for the treatment of neonatal epilepsy.

Gluconate has been widely used as an anion in many medically used drugs but is often labeled as inactive ingredient. In the relevant research literature, gluconate itself has never been directly linked to epilepsy, because the specific aims of these studies were focused on cations such as $Ca^{2+}$ and $Mg^{2+}$. For example, one case study reported that an epileptic patient was treated with Ca-gluconate and subsequently the epileptic jerks faded. Boulenguez et al., "Down-regulation of the potassium-chloride cotransporter KCC2 contributes to spasticity after spinal cord injury" *Nature Medicine* 16:302-307 (2010). The analysis attributed the ameliorative effect to $Ca^{2+}$, without any mention of a possible role for gluconate. Other observations that magnesium gluconate might have an anti-epileptic effect, have been suggested to be due to the function of $Mg^{2+}$.

The data presented herein suggest that the active ingredient in these anti-epileptic compositions is more likely gluconate rather than the divalent cation. Gluconate can be generated from the oxidation of glucose, and therefore abundant in natural food product such as fruit and honey. Anastassiadis et al., "Gluconic acid production" *Recent Patents On Biotechnology* 1:167-180 (2007). In one embodiment, the present invention contemplates that gluconate has antiepileptic effect and may support certain traditional diet treatments for epilepsy.

CLC-3 channels are voltage-gated outward rectifying Cl− channels, which belong to the CLC super family. Previous studies have shown that CLC-3 channels are essential for the regulation of endosomal acidification, presynaptic neurotransmitter accumulation, insulin secretion, and glioma cell proliferation. Hara-Chikuma et al., "ClC-3 chloride channels facilitate endosomal acidification and chloride accumulation" *The Journal Of Biological Chemistry* 280: 1241-1247 (2005); Riazanski et al., "Presynaptic CLC-3 determines quantal size of inhibitory transmission in the hippocampus" *Nature Neuroscience* 14:487-494 (2011);

Deriy et al., "The granular chloride channel ClC-3 is permissive for insulin secretion" *Cell Metabolism* 10:316-323 (2009): Li et al., "Suppression of sulfonylurea- and glucose-induced insulin secretion in vitro and in vivo in mice lacking the chloride transport protein ClC-3" *Cell Metabolism* 10:309-315 (2009); Cuddapah et al., "Bradykinin-induced chemotaxis of human gliomas requires the activation of KCa3.1 and ClC-3" *The Journal Of Neuroscience: The official journal of the Society for Neuroscience* 33:1427-1440 (2013); and Habela et al., "ClC3 is a critical regulator of the cell cycle in normal and malignant glial cells" *The Journal Of Neuroscience: the official journal of the Society for Neuroscience* 28:9205-9217 (2008).

Although it is not necessary to understand the mechanism of an invention, it is believed that CLC-3 Cl− channels mediate a large outward rectifying Cl− current that is prominent in early postnatal brains but largely disappeared in adult brains. Consequently, gluconate is a more potent anti-epileptic drug for the treatment of neonatal epilepsy. It is further believed that the activation of CLC-3 Cl− channels during epileptogenesis alters the intracellular Cl− homeostasis and makes GABA function more excitatory. Furthermore, the data presented herein shows that the CLC-3 Cl− channels may play a bigger role in neonatal epilepsy than previously thought Cl− transporters. In fact, Cl− channels and Cl− transporters may play different roles in controlling intracellular Cl− homeostasis due to their differences in voltage dependence. For example, in resting a condition voltage-sensitive CLC-3 Cl− channels are inactive, and therefore Cl− transporters such as NKCC1 is the major player that maintains intracellular Cl− homeostasis in developing neurons. Ben-Ari, Y., "Excitatory actions of gaba during development: the nature of the nurture" *Nature Reviews. Neuroscience* 3:728-739 (2002); Kaila et al., "Cation-chloride cotransporters in neuronal development, plasticity and disease" *Nature Reviews. Neuroscience* 15:637-654 (2014); and Blaesse et al., "Cation-chloride cotransporters and neuronal function" *Neuron* 61:820-838 (2009).

During epileptogenesis, however, CLC-3 Cl− channels are activated and the large Cl− influx significantly increases [Cl−]$_i$, resulting in enhanced excitatory GABAergic transmission and exacerbated epileptic activity. In some embodiments, the present invention contemplates that blocking CLC-3 channels with gluconate disrupts this positive loop and inhibit neonatal epilepsy in the developing brains. Moreover, CLC-3 knockout mice do not have large outward rectifying Cl− current, and consequently the recurrent burst activity is significantly diminished. By comparing gluconate with other potential anti-epileptic drugs (AEDs), the data presented herein shows that gluconate is more potent than phenobarbital or bumetanide in suppressing neonatal epilepsy. Gluconate acts differently from bumetanide, which blocks NKCC1 and affects EGABA under resting condition, whereas gluconate does not affect normal EGABA under physiologic condition, but blocks CLC-3 channel activation during epileptogenesis.

Since gluconate is a natural organic acid and already used as a food and drug additive with minimal side effects. In one embodiment, the present invention contemplates that gluconate compositions, in the absence of a divalent cation, are therapeutic drugs that can be used for the treatment of neonatal epilepsy that is resistant to many current anticonvulsant drugs.

I. Convulsive Disorders

The term convulsion is often used interchangeably with seizure. Convulsions occur when a person's body shakes rapidly and uncontrollably. During convulsions, the person's muscles contract and relax repeatedly. There are many different types of seizures. Some have mild symptoms without shaking. Some seizures only cause a person to have staring spells. These may go unnoticed. Specific symptoms of convulsions may depend on what part of the brain is involved. Symptoms usually occur suddenly and may include, but are not limited to: brief blackout followed by a period of confusion (the person cannot remember for a short time); changes in behavior such as picking at one's clothing; drooling or frothing at the mouth; eye movements; grunting and snorting; loss of bladder or bowel control; mood changes such as sudden anger, unexplainable fear, panic, joy, or laughter; shaking of the entire body; sudden falling, tasting a bitter or metallic flavor; teeth clenching; temporary stop in breathing, and/or uncontrollable muscle spasms with twitching and jerking limbs. Symptoms may stop after a few seconds or minutes, or continue for up to 15 minutes but they rarely continue longer.

Epileptic seizures are often caused by overexcitation of the brain circuits, which can be inhibited by boosting $GABA_A$ receptors ($GABA_A$-Rs), a major inhibitory receptor family in the adult brain. Therefore, anti-epileptic drugs (AEDs) are often developed to increase GABAA-R function, such as benzodiazepine and barbiturate drugs that are generally targeted towards adult patients. Bialer et al., "Key factors in the discovery and development of new antiepileptic drugs. Nature reviews. Drug discovery 9, 68-82 (2010). However, while $GABA_A$-Rs are mostly inhibitory in the adult brain, $GABA_A$-Rs are mostly excitatory in the developing brain of neonates and/or infants. Chen et al., "Excitatory actions of GABA in developing rat hypothalamic neurones" *The Journal Of Physiology* 494(Pt 2):451-464 (1996); and Ben-Ari Y., "Excitatory actions of gaba during development: the nature of the nurture" *Nature Reviews Neuroscience* 3:728-739 (2002). The excitatory GABAergic transmission in the developing brain also explains why GABA agonists are often ineffective in controlling neonatal seizures, and sometimes can even exacerbate neonatal seizure activity. Farwell et al., "Phenobarbital for febrile seizures—effects on intelligence and on seizure recurrence" *The New England Journal Of Medicine* 322:364-369 (1990). Therefore, some AEDs can potentially exacerbate neonatal seizures by enhancing excitatory $GABA_A$-R function in the developing brain.

Classically, the excitatory function of $GABA_A$-Rs in developing neurons has been attributed to the regulation by chloride ion (Cl−) transporters NKCC1 and KCC2. Ben-Ari et al., "GABA: a pioneer transmitter that excites immature neurons and generates primitive oscillations" *Physiol Rev* 87:1215-1284 (2007); Kahle et al., "Roles of the cation-chloride cotransporters in neurological disease" *Nat Clin Pract Neurol* 4:490-503 (2008); and Kaila et al., "Cation-chloride cotransporters in neuronal development, plasticity and disease" *Nature Reviews. Neuroscience* 15:637-654 (2014). A previous study found that NKCC1 might facilitate neonatal seizures in rodent animals. Dzhala et al., "NKCC1 transporter facilitates seizures in the developing brain" *Nature Medicine* 11:1205-1213 (2005). However, a recent clinical trial in infant babies found severe side effects of NKCC1 blocker bumetanide and very limited effect in treating neonatal seizure. Pressler et al., "Bumetanide for the treatment of seizures in newborn babies with hypoxic ischaemic encephalopathy (NEMO): an open-label, dose finding, and feasibility phase ½ trial" *Lancet Neurol* 14:469-477 (2015). Because excitatory GABAergic transmission plays a fundamental role in many neural developmental processes, blocking NKCC1 may significantly alter GABA function under physiological condition and raise a potential risk of disrupting normal brain development. Ben-Ari, Y., "Excitatory actions of gaba during development: the nature of the nurture" *Nature reviews. Neuroscience* 3:728-739 (2002); Kaila et al., "Cation-chloride cotransporters in neuronal development, plasticity and disease" *Nature reviews. Neuroscience* 15:637-654 (2014); Wang et al., "Blocking early GABA depolarization with bumetanide results in permanent alterations in cortical circuits and sensorimotor gating deficits" *Cerebral cortex* 21:574-587 (2011); and Deidda et al., "Early depolarizing GABA controls critical-period plasticity in the rat visual cortex" *Nature neuroscience* 18:87-96 (2015). More recent studies suggest that factors other than Cl⁻ co-transporters may also contribute to Cl⁻ homeostasis, such as impermeant anions, voltage-gated inward rectifying chloride channel CLC-2, and voltage-gated outward rectifying chloride channel CLC-3. Glykys et al., "Local impermeant anions establish the neuronal chloride concentration" *Science* 343:670-675 (2014); Foldy et al., "Regulation of fast-spiking basket cell synapses by the chloride channel ClC-2" *Nature neuroscience* 13:1047-1049 (2010); Rinke et al., "ClC-2 voltage-gated channels constitute part of the background conductance and assist chloride extrusion" *The Journal of neuroscience: the official journal of the Society for Neuroscience* 30:4776-4786 (2010); Kawasaki et al., "Cloning and expression of a protein kinase C-regulated chloride channel abundantly expressed in rat brain neuronal cells" *Neuron* 12:597-604 (1994); and Wang et al., "CLC-3 channels modulate excitatory synaptic transmission in hippocampal neurons" *Neuron* 52:321-333 (2006).

Recent studies suggest that Cl⁻ channels, such as CLC-3 channels, may also contribute to the changes of intracellular Cl⁻ concentration ($[Cl^-]_i$). Zhou et al., "Regulation of intracellular Cl– concentration through volume-regulated ClC-3 chloride channels in A10 vascular smooth muscle cells" *The Journal Of Biological Chemistry* 280:7301-7308 (2005). CLC-3 channels belong to a subfamily of voltage-dependent outward rectifying Cl⁻ channels. Jentsch T. J., "Chloride and the endosomal-lysosomal pathway: emerging roles of CLC chloride transporters" *The Journal of Physiology* 578:633-640 (2007); Graves et al., "The Cl–/H+ antiporter ClC-7 is the primary chloride permeation pathway in lysosomes" *Nature* 453:788-792 (2008); Picollo et al., "Chloride/proton antiporter activity of mammalian CLC proteins ClC-4 and ClC-5" *Nature* 436:420-423 (2005); Scheel et al., "Voltage-dependent electrogenic chloride/proton exchange by endosomal CLC proteins" *Nature* 436:424-427 (2005); and Hara-Chikuma et al., "ClC-3 chloride channels facilitate endosomal acidification and chloride accumulation" *The Journal Of Biological Chemistry* 280:1241-1247 (2005). CLC-3 channels are ubiquitously expressed throughout the brain, with high expression level in the hippocampus and cerebellum. Duran et al., "Chloride channels: often enigmatic, rarely predictable" *Annual Review Of Physiology* 72:95-121 (2010); Verkman et al., "Chloride channels as drug targets" *Nature Reviews. Drug discovery* 8:153-171 (2009); and Kawasaki et al., "Cloning and expression of a protein kinase C-regulated chloride channel abundantly expressed in rat brain neuronal cells" *Neuron* 12:597-604 (1994). For example, CLC-3 knockout mice show selective postnatal neurodegeneration in the hippocampus. Stobrawa et al., "Disruption of ClC-3, a chloride channel expressed on synaptic vesicles, leads to a loss of the hippocampus" *Neuron* 29:185-196 (2001); and Dickerson et al., "Altered GABAergic function accompanies hippocampal degeneration in mice lacking ClC-3 voltage-gated chloride channels" *Brain Research* 958:227-250 (2002). However, the precise role of voltage-dependent Cl⁻ channels during epileptogenesis is largely unknown.

Neonatal seizure has been difficult to treat as compared to adult epilepsy. Neonatal seizure is different from adult seizure, and many antiepileptic drugs (AEDs) that are effective in adults often fail to treat neonatal seizure. For example, the data presented herein shows a large voltage-dependent outward rectifying Cl– current mediated by CLC-3 Cl– channels that is present in early developing brains but not in an adult brain. Although it is not necessary to understand the mechanism of an invention, it is believed that gluconate, a naturally-occurring organic acid, potently inhibits neonatal seizure by blocking CLC-3 chloride channels.

Interestingly, CLC-3 Cl– channels may be upregulated during epileptogenesis and inhibition of CLC-3 Cl– channels by gluconate essentially abolishes neonatal seizure activity, with a significantly improved potency as compared to other AEDs. It is believed that this result may be explained by the observation that CLC-3 knockout mice have no outward rectifying Cl– current in developing brains and show reduced recurrent epileptiform activity. Although it is not necessary to understand the mechanism of an invention, it is believed that activation of CLC-3 Cl– channels during epileptogenesis significantly alters intracellular Cl– homeostasis and enhances GABA excitatory function, an effect also observed with other Cl– modulators. The data presented herein identifies gluconate as a potent anti-epileptic drug to treat neonatal seizure through inhibiting CLC-3 Cl– channels. In some embodiments described herein, an anti-epileptic drug, gluconic acid, is identified that is particularly potent in suppressing neonatal seizure.

II. Divalent Cation-Based Convulsive Therapies

The administration of calcium gluconate, magnesium sulphate or phenobarbitone to 4-7 day old infants having convulsions associated with hypocalcemia has been reported. While all three compositions appeared to reduce the rate of convulsions, intra-treatment comparisons showed that magnesium sulfate was more effective than either calcium gluconate or phenobarbitone. The reference, however, does not provide any disclosure as to the effectiveness of a gluconate composition in an infant that is not in need of a cation-based therapy. Turner, T., "Comparisons of phenobarbitone, magnesium sulphate, and calcium gluconate in treatment of neonatal hypocalcaemic convulsions" *Paediatric Research Society Abstracts*, pg 244.

The administration of calcium gluconate to an infant of less than twenty days has been reported for the management of convulsions. Subsequent to this treatment, the left leg underwent swelling, inflammation, extraosseus calcification and the serum calcium levels were determined to be within normal limits. These symptoms were relieved following cessation of the calcium gluconate treatment with a diagnosis of iatrogenic calcinosis cutis. The reference, however, does not provide any disclosure as to the effectiveness of a gluconate composition in an infant that is not in need of a divalent cation-based therapy, such as calcium. Arora et al., "Iatrogenic calcinosis cutis—a rare differential diagnosis of soft-tissue infection in a neonate: A case report" *Journal of Orthopaedic Surgery* 13(2):195-198 (2005).

The administration of botanical extracts for treating seizure disorders and/or epilepsy has been reported. For example, botanical extracts have been combined with various formulations of gluconate, for example, potassium gluconate, zinc gluconate and/or copper gluconate and screened for anticonvulsant activity using a known mouse electroshock clonus model. Further, a commercially available product, NutriiVeda™, was administered to human patients ranging in age from between four and one-half (4.5) to thirty seven (37) years old to reduce seizures and/or epilepsy. It should be noted, however, a detailed compositional analysis of NutriiVeda™ was not disclosed, therefore, the exact amount of gluconate, and its relationship to divalent cations, in this product is not known. The reference, however, does not provide any disclosure as to the effectiveness of a gluconate composition in an infant that is not in need of a divalent cation-based therapy, such as calcium or zinc. Geng L., "Methods For Treating Neurological Disorders Using Nutrient Compositions" U.S. Pat. No. 8,962,042 (herein incorporated by reference).

The case of a neonate was presented who had early onset seizure associated with hypocalcemia, hyperphosphatemia, and raised parathyroid hormone. The infant did not have any stigmata of pseudohypoparathyroidism. The hypocalcemia was initially resistant to calcium therapy, but responded to vitamin D analog therapy. The diagnosis of 'neonatal pseudohypoparathyroidism' was entertained; the infant remained stable and seizure-free with normal serum biochemistry during 3 and 8 months of follow-up. Narang et al., "Neonatal pseudohypoparathyroidism" *Indian J Pediatr.* 73(1):97-98 (2006); and Manzar et al., "Transient pseudohypoparathyroidism and neonatal seizure" *J Trop Pediatr.* 47(2):113-114 (2001).

The failure of calcium-based convulsion therapy has been reported regarding a patient that developed generalized tonic-clonic seizures when she was 9 years old and these were associated with hypocalcemia. Despite treatment with calcium, seizures persisted and the patient required antiepileptic medications. She was eventually controlled with oxcarbazepine. An MRI of the head was normal. An EEG showed independent spike and wave discharges emanating from the left temporal and right frontal region. The presence of focal findings on EEG, the lack of complete response to calcium therapy, and the need for antiepileptic drug therapy indicate that some of these patients may be inherently predisposed to developing epilepsy. Gonzalez et al., "Seizures and EEG findings in an adult patient with DiGeorge syndrome: a case report and review of the literature" *Seizure* 18(9):648-651 (2009).

Hypocalcemia is a relatively uncommon but reversible cause of left ventricular dysfunction in infants and children. A 30-day-old boy with idiopathic hypocalcemia presented with congestive heart failure and convulsive seizures. He had no evidence of underlying cardiac disease. The cardiac failure responded to calcium therapy. It is suggested that hypocalcemia should be considered as a possible cause of left ventricular dysfunction in infants. Karademir et al., "Left ventricular dysfunction due to hypocalcemia in a neonate" *JPN Heart J.* 34(3):355-359 (1993).

Such reports as above teach one of skill in the art that the purpose of administering a divalent-cation gluconate therapy is to provide the divalent cation (e.g., calcium, magnesium, zinc etc.) as the effective ingredient to manage the convulsive disorder. For example, the condition of "hypocalcemia" is described as a pre-existing condition for the convulsive condition. On the other hand, calcium excess resulted in serious side effects during convulsive treatments experienced subsequent to the treatment of calcium gluconate. As such, these observations teach that the purpose of administering a divalent-cation gluconate complex to the neonate is because it was believed that divalent-cation supplementation was required for convulsion management, and gluconate was merely a suitable counter ion. Consequently, the present invention demonstrates that divalent-cation gluconate compositions are surprisingly more effective in treating convulsive conditions.

III. Gluconate-Based Convulsive Therapies

In one embodiment, the present invention contemplates that voltage-dependent CLC-3 Cl– channels may play a role in controlling intracellular Cl– concentration ($[Cl-]_i$), particularly during neonatal epilepsy. For example, CLC-3 channels may mediate a large voltage-dependent outward rectifying Cl– currents in neonatal but not adult brains that can be inhibited by gluconic acid. For example, the data show that gluconate potently suppressed neonatal epileptic activity, with a less effect in adult animals. Moreover, CLC-3 knockout mice showed an absence of voltage-dependent outward rectifying Cl– currents in neonatal brains and reduced recurrent epileptic activity. EEG recordings also confirmed that gluconate was more effective in inhibiting seizure burst activity in neonatal animals, but less effective in adult animals. Finally, CLC-3 channel activation observed during neonatal epilepsy significantly increased $[Cl-]_i$, while blocking CLC-3 channels using gluconate inhibited $[Cl-]_i$ accumulation. In one embodiment, the present invention contemplates that gluconate (a natural organic chemical) is an effective CLC-3 Cl– channel blocker and may be effective as an anticonvulsant drug to treat neonatal epilepsy.

Gluconic acid is a large organic anion, often used as a food or drug additive in a salt form such as magnesium gluconate, calcium gluconate, or potassium gluconate, where gluconate was used to help delivering calcium or magnesium or potassium. However, the functional role of gluconate itself was largely neglected in the past. The data presented herein demonstrate that gluconic acid itself acts as a Cl⁻ channel blocker and directly inhibits epileptiform activity. In some embodiments, the present invention provides that gluconate is particularly effective for suppressing neonatal seizure thereby provide a selective therapy for the treatment of neonatal epilepsy.

Gluconate is an alkanoyl organic compound having the following structure:

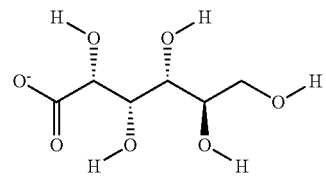 [SMILES: O=C([O-])[C@H](O)[C@@H](O)[C@H](O)[C@H](O)CO]

It is noted that the various hydroxyl groups and carboxylic acid group provide reactive species capable of functionalization and/or derivitization. Such reactive groups may be substituted with moieties including, but not limited to, a substituted or unsubstituted aryl or heteroaryls, an unsubstituted or substituted C1-C6-alkyl group, a substituted or unsubstituted 5-6-membered saturated or unsaturated fused ring, a substituted or unsubstituted 5-6-membered saturated or non-saturated ring, natural amino acid residues or synthetic amino acid residues, trihalomethyl, substituted or unsubstituted C1-C6-alkoxy, $NH_2$, SH, thioalkyl, aminoacyl, aminocarbonyl, substituted or unsubstituted C1-C6-alkoxycarbonyl, aryl, heteroaryl, substituted or unsubstituted 4-8-membered cyclic alkyl, optionally containing 1-3 heteroatoms, carboxyl, cyano, halogen, hydroxy, nitro, acetoxy, aminoacyl, sulfoxy, sulfonyl, C1-C6-thioalkoxy, C1-C6-aliphatic alkyl, substituted or unsubstituted saturated cyclic C4-C8-alkyl optionally containing 1-3 heteroatoms and optionally fused with an aryl or an heteroaryl; a substituted or unsubstituted aryl, substituted or unsubstituted heteroaryl, whereby said aryl or heteroaryl groups are optionally substituted with substituted or unsubstituted C1-C6-alkyl, like trihalomethyl, substituted or unsubstituted C1-C6-alkoxy, substituted or unsubstituted C2-C6-alkenyl, substituted or unsubstituted C2-C6-alkynyl, amino, aminoacyl, aminocarbonyl, substituted or unsubstituted C1-C6-alkoxycarbonyl, aryl, carboxyl, cyano, halogen, hydroxy, nitro, acetoxy, aminoacyl, sulfoxy, sulfonyl, C1-C6-thioalkoxy; or R5 and R6 taken together could form a substituted or unsubstituted 4-8-membered saturated cyclic alkyl or heteroalkyl group. It is expected that at least one or more of these contemplated gluconate derivatives have anticonvulsant effect that is superior to that of traditionally used divalent cation therapies.

Gluconate has been widely used as an anion in many medically used drugs and is usually labeled as an inactive ingredient. Those skilled in the art reporting anticonvulsive compounds having gluconate as a counter ion, have never suggested that gluconate is linked to any anti-epileptic effect. Instead, as discussed above, previous studies primarily focus on divalent cations such as $Ca^{2+}$ and $Mg^{2+}$, as mediating the anticonvulsive effect. For example, one case study reported that an epileptic patient was treated with Ca-gluconate and epileptic jerks faded. Boulenguez et al., "Down-regulation of the potassium-chloride cotransporter KCC2 contributes to spasticity after spinal cord injury" *Nature Medicine* 16:302-307 (2010). The authors attributed this effect to $Ca^{2+}$, totally ignoring the question as to whether gluconate may have played any role. Similarly, it is generally accepted in the art that magnesium-related anti-convulsive products, such as magnesium gluconate, might have an anti-epileptic effect, but again, it is believed that the anti-convulsive effect is due to the function of $Mg^{2+}$. In contrast to these generally held beliefs, the data presented herein demonstrate that gluconate may be just as, or more, effective than a divalent cation alone.

Gluconate can be generated from the oxidation of glucose, and is therefore abundantly found in natural food product, such as fruit and honey. Anastassiadis et al., "Gluconic acid production" *Recent Patents On Biotechnology* 1:167-180 (2007). Consequently, a dietary source of gluconate may also contribute to an anti-epileptic therapy. Since gluconate is a natural organic acid and already used as food and drug additive with minimal side-effects, gluconate derivatives could result in a new generation of therapeutic drugs for the treatment of neonatal epilepsy.

In one embodiment, the present invention contemplates that gluconic acid (e.g., gluconate) potently inhibited epileptiform burst activity in neuronal cultures as well as in hippocampal slices. Further, field potential recordings in hippocampal slices revealed that sodium gluconate potently suppressed neonatal epileptic activity, with less effect in older animals. Electroencephalographic (EEG) recordings confirmed that sodium gluconate was more effective in inhibiting epileptic seizures in neonatal animals, but less effective in adult animals. Whole-cell patch clamp recordings demonstrated that sodium gluconate significantly inhibited the voltage-dependent $Cl^-$ currents in hippocampal pyramidal neurons, which are mainly mediated by CLC-3 channels. The data presented herein identify a natural organic chemical, gluconic acid and derivatives thereof, as previously unknown, and effective, anticonvulsant drugs for neonatal epilepsy.

A. Inhibition Of Epileptiform Activity

The functional role of $Cl^-$ was investigated during epileptogenesis by replacing extracellular $Cl^-$ (i.e., for example, 137 mM $Cl^-$) in the bath solution with large anions such as gluconic acid. Surprisingly, a concentration of between approximately 5-20 mM sodium gluconic acid (NaGcA) in the bath solution, inhibited spontaneous epileptiform activity in cultured cortical neurons. See, FIG. 1A. Such potent inhibition of epileptiform activity by low concentration of NaGcA could not be explained purely by concentration change, because there was still >117 mM in the bath solution. To determine whether NaGcA might directly inhibit epileptiform activity, cyclothiazide (CTZ) was used to elicit robust epileptiform burst activity in neuronal cultures. Qi et al., "Cyclothiazide induces robust epileptiform activity in rat hippocampal neurons both in vitro and in vivo" *The Journal Of Physiology* 571:605-618 (2006). The data demonstrated that CTZ-induced epileptiform activity was completely blocked by 10 mM NaGcA, and the inhibition was dose-dependent See, FIG. 1B and FIG. 1C, respectively. The effect of NaGcA was reversible, because the burst activity was restored to the control level after washing out NaGcA. See, FIG. 1A and FIG. 1C. These data indicate that NaGcA exerts a potent inhibitory effect on epileptiform burst activity in cultured neurons.

To ensure that such inhibitory effect of NaGcA was not limited to the CTZ epilepsy model, NaGcA was further tested in two additional epileptic models. Firstly, cortical neurons were treated with 1 μM kainic acid (KA), a potent neurotoxin, for 2 hrs to induce epileptic burst activity. Whole-cell patch-clamp recordings showed that 10 mM NaGcA greatly suppressed the epileptiform burst activity induced by KA. See, FIG. 1D and FIG. 1E. Secondly, cortical neurons were incubated in 50 μM 4-aminopyridine (4-AP) for 2 hrs, which also induced long-lasting epileptiform burst activity. Similarly, application of 10 mM NaGcA completely blocked the 4-AP-induced epileptiform activity. See, FIG. 1F and FIG. 1G. Together, these results demonstrate that NaGcA is a potent and general inhibitor for epileptiform activity in cultured neurons.

Whether NaGcA can inhibit the induction of epileptic activity was then determined. For this purpose, a combination of NaGcA and CTZ was added during the induction period. Neurons treated by CTZ alone showed robust epileptiform activity; however, neurons treated with 10 μM CTZ together with 10 mM NaGcA showed a great reduction of epileptiform activity. See, FIG. 1H, cf., top portion to bottom portion. Almost 90% of control neurons showed epileptiform activity after CTZ-treatment (e.g., approximately 19 out of 22 neurons), whereas only 18% (e.g., approximately 3 out of 17 neurons, p<0.001, $\chi^2$ test) of neurons co-treated with 10 mM NaGcA showed epileptiform activity. See, FIG. 1I(a). The average frequency and duration of epileptiform bursts were also significantly reduced in neurons co-treated with NaGcA. See, FIG. 1I(b) and FIG. 1I(c). Together, these data demonstrate that both acute and chronic NaGcA application can suppress epileptiform activity in cultured neurons.

B. Kainic Acid-Induced Cell Death Protection

Neuronal death is the serious side-effect of epilepsy. Sagar et al., "Hippocampal neuron loss in temporal lobe epilepsy: correlation with early childhood convulsions" *Annals of Neurology* 22:334-340 (1987); and Sass et al., "Verbal memory impairment resulting from hippocampal neuron loss among epileptic patients with structural lesions" *Neurology* 45:2154-2158 (1995). The data presented herein demonstrate that gluconate not only has anti-epileptic effect, but also exerts neural protective effect against KA-induced neuronal death.

Epileptic activity may induce cell death both in epileptic patients and animal models. Chen et al., "Differential roles of NR2A- and NR2B-containing NMDA receptors in activity-dependent brain-derived neurotrophic factor gene regulation and limbic epileptogenesis" *The Journal Of Neuroscience: the official journal of the Society for Neuroscience* 27:542-552 (2007); and Naseer et al., "Maternal epileptic seizure induced by pentylenetetrazol: apoptotic neurodegeneration and decreased GABAB1 receptor expression in prenatal rat brain" *Molecular Brain* 2:20 (2009). To evaluate whether the anti-epileptic effect of NaGcA might be neuroprotective, a kainic acid (KA)-induced cell death model was used in conjunction with the LIVE/DEAD® Viability/Cytotoxicity Assay Kit (L3224, Life Technologies, Inc.) to analyze the neuronal survival rate. Wu et al., "Protective effect of resveratrol against kainate-induced temporal lobe epilepsy in rats" *Neurochemical Research* 34:1393-1400 (2009). In a control group, most neurons appeared to be healthy in morphology and were stained by calcein (green, live) but not ethidium homodimer-1 (EthD-1, red, death). See, FIG. 1J, left. After exposure to 10 µM KA for 24 hrs, most neurons were dead as shown by EthD-1 staining. See, FIG. 1J, middle left). Interestingly, KA-induced neuronal death was abolished by co-application of 20 mM NaGcA. See, FIG. 1J, middle right. Neurons exposed to 20 mM NaGcA alone had no side effect on their survival rate. See, FIG. 1J, right. Quantitative data showed that the neuroprotective effect of NaGcA was also dose-dependent. See, FIG. 1K. These experiments suggest that gluconate not only inhibits epileptiform activity but also exerts neuroprotective effect.

C. Chloride Ion Current Inhibition

The studies presented herein demonstrate that gluconic acid blocks $Cl^-$ channels. Although it is not necessary to understand the mechanism of an invention, it is believed that gluconic acid blocks these channels because it is a large organic compound with negative charge. For example, as a large anion, it is believed that gluconic acid may not pass through the $Cl^-$ channel as easily as $Cl^-$ ion itself. $Cl^-$ channels have been linked to human epilepsy patients. Mutations in CLC-1 channels were identified in many idiopathic epileptic patients. Chen et al., "Novel brain expression of ClC-1 chloride channels and enrichment of CLCN1 variants in epilepsy" *Neurology* 80:1078-1085 (2013). CLC-2 channel mutations have also been found in human patients but some studies suggest that the mutations may not contribute to epilepsy. Haug et al., "Mutations in CLCN2 encoding a voltage-gated chloride channel are associated with idiopathic generalized epilepsies" *Nat Genet* 33:527-532 (2003); Kleefuss-Lie et al., "CLCN2 variants in idiopathic generalized epilepsy" *Nat Genet* 41:954-955 (2009); and Niemeyer et al., "No evidence for a role of CLCN2 variants in idiopathic generalized epilepsy" *Nat Genet* 42:3 (2010). CLC-3 channels are widely expressed in different brain regions, and hippocampus is one of the highest expression regions. Duran et al., "Chloride channels: often enigmatic, rarely predictable" *Annual Review Of Physiology* 72:95-121 (2010); Verkman et al., "Chloride channels as drug targets" *Nature Reviews. Drug Discovery* 8:153-171 (2009); and Kawasaki et al., "Cloning and expression of a protein kinase C-regulated chloride channel abundantly expressed in rat brain neuronal cells" *Neuron* 12:597-604 (1994).

Experiments were designed to answer the question as to what is/are the molecular target(s) of gluconate. Ion channel regulation was first investigated where a comparison of NaGcA on sodium, potassium or calcium channels was made. The data show that there were no significant changes in $Na^+$, $K^+$ and $Ca^{2+}$ currents after NaGcA treatment. See, FIGS. 2A-2F. Although it is not necessary to understand the mechanism of an invention, it is believed that since gluconic acid is an organic anion, it might affect neuronal anion channels.

The data presented herein show that the $Cl^-$ currents in cultured cortical neurons were outwardly rectifying, and were significantly decreased in the presence of 10 mM NaGcA. See, FIGS. 2G,H; control, 913±171 pA; NaGcA, 499±89 pA; n=7; P<0.007, paired t-test; recorded at +90 mV). Thus, one target of NaGcA may be a $Cl^-$ channel. To solidify a close link between $Cl^-$ channels and epileptogenesis, the effect of two classic Cl– channel blockers was examined; 5-Nitro-2-(3-phenylpropylamino) benzoic acid (NPPB) and 4,4'-Diisothiocyanato-2,2'-stilbenedisulfonic acid disodium salt (DIDS). Application of NPPB (100 µM) or DIDS (100 µM) significantly suppressed the Cl– currents in cultured neurons. See, FIG. 2I,L. It was also demonstrated that both NPPB (100 µM) and DIDS (100 µM) significantly inhibited the epileptiform activity induced by CTZ (10 µM, 24 hrs). See, FIG. 2M,N; n=9. Taken together, these results suggest that NaGcA can inhibit $Cl^-$ channels, which are involved in epileptogenesis.

D. Neonatal Hippocampal Slice Epileptiform Activity Inhibition

The possibility that the above described effects of gluconate on in cultured neurons were artifacts, the anti-epileptic activity of NaGcA was examined in hippocampal slices with relatively intact neuronal circuits. Field potentials were recorded in the CA3 pyramidal layer and induced epileptic burst activity in $Mg^{2+}$-free artificial cerebral spinal fluid (aCSF). After induction of stable epileptic burst activity (~30 min), 20 mM NaGcA was applied into $Mg^{2+}$-free aCSF to test its effect on the epileptic activity. The data show that NaGcA exerted an anti-epileptic effect in the brain slices from P6-P12 neonatal animals (FIGS. 2A and 2c), but a modest effect in older animals around one month. See, FIGS. 3A and 3C cf., FIG. 3E. The power spectrum of field potentials was then analyzed before, during and after NaGcA applications. The amplitude of power was significantly reduced after application of NaGcA in neonatal animals but only slightly reduced in older animals (e.g., P26). See, FIGS. 3B and 3D cf., FIG. 3F. Quantitatively, NaGcA inhibited 60% of the average power of epileptic activity in neonatal animals (P6-8, 59.6±4.3%, n=10 slices from 5 pups; P10-12, 62.1±3.8%, n=10 slices from 5 pups; P<0.001, paired t-test), but only reduced 20% in older animals (P21-33, 23.8±4.1%, n=7 slices form 4 pups; p<0.005, paired t-test). See, FIG. 3G. These results suggest that NaGcA may have potent anti-epileptic activity in neonatal brains.

Whether the NaGcA effect on epileptic activity is generally applicable to other epilepsy models besides a 0 Mg2+ model in P6-P12 neonatal animals was further determined. For example, a 4-AP model was use where bath application of $K^+$ channel blocker 4-AP (50 µM) induced a robust epileptic burst activity in the CA3 pyramidal layer. Further addition of 20 mM NaGcA to a 4-AP-containing bath solution significantly reduced the epileptic activity, which was reversible after washout of NaGcA. See FIG. 4A. The amplitude of power also showed significant reduction in the presence of NaGcA, and the summarized data showed an average of 70.2±5.3% reduction of the power amplitude by NaGcA (n=9 slices from 4 pups; P<0.001, paired t-test). See, FIG. 4B and FIG. 4C, respectively. A high K$^+$ model was also used where elevated extracellular K$^+$ (+8.5 mM) evoked epileptic burst activity in the CA3 pyramidal layer. See, FIG. 4D. Similarly, addition of 20 mM NaGcA in high K$^+$ aCSF also blocked the epileptic burst activity and reduced the power amplitude. See, FIGS. 4D,E. Statistical analysis revealed that NaGcA significantly reduced the amplitude of power by 70.8±4.9% (n=5 slices from 2 pups; P<0.001, paired t-test) in a high K$^+$ model. See, FIG. 4F. In summary, these results demonstrate that NaGcA can potently suppress neonatal epilepsy in a variety of epilepsy models.

E. CLC-3 Chloride Ion Channel Inhibition

As discussed above, NaGcA inhibited Cl− currents in cultured neurons. See, FIG. 2. Previous studies reported that hippocampal cultured neurons had voltage-dependent CLC-3 Cl− channels. Wang et al., "CLC-3 channels modulate excitatory synaptic transmission in hippocampal neurons" *Neuron* 52:321-333 (2006). As shown herein, gluconate has strong inhibitory effect on the outward rectifying currents mediated by CLC-3 channels. The postsynaptic Cl$^-$ influx through the CLC-3 channels can potentiate the NMDA receptor-mediated excitatory currents, and over activation of NMDA receptors is involved in seizure-induced neuronal cell death. Therefore, the neuroprotective effect of gluconate may be through an indirect suppression of NMDA receptor function.

While hippocampal formation is known to be one of the most frequent epileptogenic structures in the rodent brain, so far there is little study directly investigating the relationship between CLC-3 channels and epilepsy, except a report that CLC-3 knock-out mice showed a marked resistance to PTZ-induced epilepsy. Dickerson et al., "Altered GABAergic function accompanies hippocampal degeneration in mice lacking ClC-3 voltage-gated chloride channels" *Brain Research* 958:227-250 (2002). Electrophysiological studies presented herein found that CLC-3 channels mediate the CL currents in hippocampal CA3 pyramidal neurons, and sodium gluconate strongly inhibits CLC-3 channels. Further, the data also show that, after induction of epileptic activity, CLC-3 channels are upregulated in neonatal hippocampal slices, and sodium gluconate can abolish the increased chloride currents.

Therefore, CLC-3 channels are apparently involved in neonatal epileptogenesis. Supporting these observations, CLC-3 channels have been found highly expressed in human glioma cells and can be blocked by gluconate. Olsen et al., "Expression of voltage-gated chloride channels in human glioma cells" *The Journal Of Neuroscience: the official journal of the Society for Neuroscience* 23:5572-5582 (2003). Further, it has been reported that a high incidence is apparent between glioma and epilepsy, and misregulation of Cl$^-$ homeostasis is involved in glioma-associated epilepsy. Buckingham et al., "Glutamate release by primary brain tumors induces epileptic activity" *Nature Medicine* 17:1269-1274 (2011); and Pallud et al., "Cortical GABAergic excitation contributes to epileptic activities around human glioma' *Sci Transl Med* 6:244ra289 (2014). Together, these findings suggest a potential link between Cl$^-$ channels and neonatal epileptogenesis. As a potent inhibitor of CLC-3 channels, gluconate may be a previously unknown antiepileptic drug for the treatment of neonatal epilepsy.

Consistently, the data presented herein shows a voltage-dependent outward rectification Cl$^-$ current in CA3 pyramidal neurons in hippocampal slices. See, FIG. 5A, left. For example, Cl$^-$ currents were dramatically reduced after application of NaGcA (20 mM). See, FIG. 5A, right. Quantitative data analysis of the I-V curves of the Cl− currents before and after NaGcA. See, FIG. 5B. To directly test whether the voltage-sensitive Cl$^-$ current was mediated by CLC-3 Cl$^-$ channels, CLC-3 specific antibodies were introduced into the pipette solution to block CLC-3 channels. Wang et al., "Functional effects of novel anti-ClC-3 antibodies on native volume-sensitive osmolyte and anion channels in cardiac and smooth muscle cells" *American Journal Of Physiology. Heart and circulatory physiology* 285: H1453-1463 (2003); and Duan et al., "Functional inhibition of native volume-sensitive outwardly rectifying anion channels in muscle cells and *Xenopus* oocytes by anti-ClC-3 antibody" *The Journal Of Physiology* 531:437-444 (2001).

Indeed, an outward rectified Cl$^-$ current was greatly reduced after 10 min dialysis of the CLC-3 antibody (1:100), but no obvious changes were observed in the control IgG-dialyzed neurons. See, FIG. 5C. Quantitatively, Cl$^-$ current density in control condition was 36.2±1.4 pA/pF at 90 mV (n=10 cells from 4 pups) and 33.5±2.3 pA/pF in the IgG group (n=10 cells from 3 pups), but decreased to 13.7±2.3 pA/pF in the CLC-3 antibody group (n=11 cells from 4 pups; P<0.001, one-way ANOVA with Tukey post hoc tests). See, FIG. 5D. Thus, the currents in CA3 pyramidal neurons are mainly mediated by CLC-3 channels, consistent with previous findings in CLC-3−/− hippocampal neurons.

NaGcA was also tested to determine whether the compound can specifically inhibit CLC-3 channels. HEK293T cells were transfected with CLC-3-EGFP plasmid and the expression of CLC-3 channels was confirmed with the CLC-3 specific antibodies. See, FIG. 5E, and Matsuda et al., "Overexpression of CLC-3 in HEK293T cells yields novel currents that are pH dependent" *American Journal Of Physiology. Cell physiology* 294:C251-262 (2008). Whole-cell recordings also revealed large outward rectification currents in CLC-3-transfected HEK293T cells (control, 1012±123 pA at +90 mV, n=7 cells from 2 batches of cultures), but no currents were observed in EGFP-transfected control cells. See, FIG. 5F. Further, the application of 20 mM NaGcA significantly reduced CLC-3-mediated Cl$^-$ currents (NaGcA, 544±59 pA at +90 mV, n=7 cells from 2 batches; P<0.004 compared to control, paired t-test), which was also reversible after washout of NaGcA (925±124 pA at +90 mV, n=7 cells from 2 batches; P>0.4 compared to control, paired t-test). See, FIGS. 5F,G. Together, these data demonstrate that NaGcA is a potent inhibitor of CLC-3 Cl$^-$ channels, which mediate the major outward rectification currents in the CA3 pyramidal neurons.

F. Epileptogeneic Upregulation Of CLC-3 Channels

To determine whether CLC-3 channels are involved in epileptogenesis, CLC-3 expression level was determined before and after the induction of epileptic activity in P8-P12 neonatal brain slices. Hippocampal slices were incubated in Mg$^{2+}$-free aCSF for 1 hr to induce epileptic activity and then performed CLC-3 immunostaining to examine the CLC-3 expression level. Control slices were incubated in normal aCSF for 1 hr correspondingly. Interestingly, the CLC-3 immunoreactivity in hippocampal CA3 pyramidal layer showed a significant increase in 0 Mg$^{2+}$-treated slices compared to the control. See, FIG. 6A,B; control, 11.2±1.5 a.u., n=10 slices from 4 pups; 0 Mg$^{2+}$, 20.4±2.8 a.u., n=11 slices from 4 pups; P<0.02, Student's t-test. Such an elevated expression level of CLC-3 was further confirmed by Western blot. See, FIGS. 6C,D. Thus, the CLC-3 channels are upregulated in neonatal epileptic slices.

Furthermore, a patch-clamp recording directly measured the Cl$^-$ currents of CA3 pyramidal neurons in control and 0

Mg$^{2+}$-treated slices. Consistent with immunostaining and Western blot results, whole-cell recordings also revealed a significant increase of Cl$^-$ currents in 0 Mg$^{2+}$-treated neurons. See, FIG. 6E,F; control, 31.2±1.8 pA/pF at +90 mV, n=15 cells from 3 pups; 0 Mg$^{2+}$, 42.2±2.4 pA/pF, n=15 cells from 3 pups; P<0.001, one-way ANOVA with Tukey post hoc tests. Further, the majority of Cl$^-$ currents after 0 Mg$^{2+}$ treatment were significantly inhibited by NaGcA. See, FIG. 6E,F; NaGcA, 7.3±0.6 pA/pF, n=11 cells from 2 pups; P<0.001, one-way ANOVA with Tukey post hoc tests. These results suggest that CLC-3 channels may play an role during neonatal epileptogenesis.

G. Neonatal Seizure Inhibition

To induce neonatal seizure, a commonly used KA model was used. Injection of KA (2 mg/kg, i.p.) into P10-P12 neonatal mice elicited robust epileptic seizure bursts as revealed by in vivo EEG recordings. See, FIG. 7A,B. When NaGcA (2 g/kg, i.p.) was injected 10 min after KA injection, the epileptic seizure activity was essentially abolished. See, FIG. 7C,D. Power analysis confirmed that the amplitude of power was significantly inhibited by NaGcA injection. See, FIG. 7E,F. These data show that NaGcA is a potent in vivo anti-neonatal seizure drug.

H. Adult Seizure Inhibition

NaGcA was determined as to whether the compound can also be used to treat adult epilepsy. Preliminary data showed that the KA convulsion model has high mortality rate. However, a similar PTZ model resulted in reliable epileptic seizures in adult mice. See, FIG. 8A. The data show that NaGcA prolonged the latency of epileptic seizure burst induced by PTZ, but did not suppress the epileptic burst activity as effective as seen in the neonatal animals. See, FIG. 8. Therefore, NaGcA may be a unique anti-epileptic drug that is more potent in treating neonatal seizure than that for adult epilepsy.

I. Chloride Ion Channel Blocker Whole Cell Inhibition

A related question is that other Cl$^-$ channel blockers, such as NPPB and NFA, which also inhibit neonatal seizures also block ion channel-related activity. See, FIG. 9 and FIG. 10. In one embodiment, the present invention contemplates that compounds including, but not limited to, gluconate, NPPB, Niflumic acid, DIDS, flufenamic acid, can act similarly in inhibiting neonatal seizure. Although it is not necessary to understand the mechanism of an invention it is believed that neonatal seizure inhibition may occur by chloride ion channel inhibition.

IV. CLC-3 Cl$^-$ Channels Mediate a Large Outward-Rectifying Current in Developing Neurons Alteration of GABA function has been closely associated with epilepsy. GABA function may be determined by intracellular Cl$^-$ concentration ([Cl$^-$]$_i$) because GABAA receptors (GABAA-Rs) are believed to be ligand-gated Cl$^-$ channels. For example, previous studies have extensively investigated the role of Cl$^-$ transporters, such as KCC2 and NKCC1, in regulating [Cl$^-$]$_i$ and hence GABA functions. However, how other Cl$^-$ channels might affect [Cl$^-$]$_i$ and GABA function has not been well understood.

The data presented herein investigates whether voltage-dependent Cl$^-$ channels contribute to [Cl$^-$]$_i$ homeostasis and/or regulate GABA functions. Previously, voltage-dependent Cl$^-$ currents were recorded that revealed a large outward rectifying Cl$^-$ current (3.3±0.3 nA) in CA3 pyramidal neurons of hippocampal slices from neonatal mice (e.g., P8-12). FIG. 11A, top left panel. Surprisingly, such voltage-dependent outward rectifying Cl$^-$ current decreased significantly in adult brains (e.g., P60-62). FIGS. 11A and 11B.

These data suggested a developmental change of Cl$^-$ channels during brain development. The Cl$^-$ currents we recorded from CA3 pyramidal neurons resembled the voltage-dependent CLC-3 Cl$^-$ currents reported previously in cultured hippocampal neurons. Wang et al., "CLC-3 channels modulate excitatory synaptic transmission in hippocampal neurons" Neuron 52:321-333 (2006); and Huang et al., "Calcium-activated chloride channels (CaCCs) regulate action potential and synaptic response in hippocampal neurons" Neuron 74:179-192 (2012).

To test whether CLC-3 Cl$^-$ channels mediated the Cl$^-$ currents in neonatal CA3 neurons, CLC-3-specific antibodies were tested for blockade of CLC-3 channels. Wang et al., "Functional effects of novel anti-ClC-3 antibodies on native volume-sensitive osmolyte and anion channels in cardiac and smooth muscle cells" American Journal Of Physiology. Heart And Circulatory Physiology 285:H1453-1463 (2003); and Duan et al., "Functional inhibition of native volume-sensitive outwardly rectifying anion channels in muscle cells and Xenopus oocytes by anti-ClC-3 antibody" The Journal Of Physiology 531:437-444 (2001). Indeed, the outward rectifying Cl$^-$ current was greatly reduced after 10 min dialysis with the CLC-3 antibody (1:100), but no obvious change when dialyzed with pre-absorbed control antibody. FIG. 11D.

Moreover, Cl$^-$ currents were directly examined in CLC-3 knockout mice. Huang et al., "ClC-3 deficiency protects preadipocytes against apoptosis induced by palmitate in vitro and in type 2 diabetes mice" Apoptosis: An International Journal On Programmed Cell Death 19:1559-1570 (2014); Liu et al., "ClC-3 deficiency prevents apoptosis induced by angiotensin II in endothelial progenitor cells via inhibition of NADPH oxidase" Apoptosis: An International Journal On Programmed Cell Death 18:1262-1273 (2013); and Zheng et al., "Deficiency of volume-regulated ClC-3 chloride channel attenuates cerebrovascular remodeling in DOCA-salt hypertension" Cardiovascular Research 100:134-142 (2013). Immunostaining confirmed the absence of CLC-3 signal in the CA3 region of CLC-3 KO mice. FIG. 11E. Accordingly, an outward rectifying Cl$^-$ current was also largely absent in the CA3 neurons of CLC-3 KO mice (WT, 33.1±1.3 pA/pF, n=10; CLC-3 KO, 9.0±1.6 pA/pF, n=6). FIGS. 11F and 11G. Together, these results indicate that CLC-3 Cl$^-$ channels mediate a large outward rectifying Cl$^-$ current in the neonatal brain, but such Cl$^-$ current significantly diminished in the adult brain.

Further testing found sodium gluconic acid (NaGcA) as a potent inhibitor to block the Cl$^-$ currents in neonatal brains. FIG. 11A-C; green tracings. In the adult brains or in CLC-3 KO mice, NaGcA had no effect on the Cl$^-$ currents. FIGS. 11A, 11B and 11G. These data suggest that NaGcA may be an inhibitor for CLC-3 channels. Olsen et al., "Expression of voltage-gated chloride channels in human glioma cells" The Journal Of Neuroscience: The Official Journal Of The Society For Neuroscience 23:5572-5582 (2003). To directly test this idea, CLC-3 channels were overexpressed in HEK293T cells and expression was confirmed with CLC-3 specific antibody binding. FIG. 11H and Matsuda et al., "Overexpression of CLC-3 in HEK293T cells yields novel currents that are pH dependent" American Journal Of Physiology. Cell Physiology 294:C251-262 (2008). Whole-cell recordings revealed large outward rectifying Cl$^-$ currents in CLC-3-transfected HEK293T cells (1012±123 pA, n=7), but not in EGFP-transfected control cells. FIG. 11I. Furthermore, application of 20 mM NaGcA significantly reduced the CLC-3 channel-mediated Cl$^-$ currents. FIGS. 11I and 11J. Thus, the present data identifies NaGcA as a potent inhibitor of CLC-3 Cl- channels.

It was also found that gluconate can inhibit Cl- currents in the presence or absence of a divalent cation (e.g., calcium or magnesium). The data presented herein compares the efficacy of Cl- current inhibition between sodium gluconate, magnesium gluconate and gluconic acid. The data demonstrate that equivalent Cl- current inhibition is observed with all three counterions. FIGS. 17A-E. Therefore, these data show that it is gluconic acid, not the cation it carries, is the effective component. Previous studies using gluconate salt often attribute the clinical effect to the cations it carries, and gluconic acid was thought as only food/drug additive, not the major effector. The data show that the art was incorrect in this interpretation, and more specifically, that a divalent cation is not a required component for gluconate to have anti-epileptic efficacy.

V. CLC-3 Channels And Neonatal Epilepsy

To understand the functional role of CLC-3 channels in neonatal epilepsy, CLC-3 channel expression levels were determined after induction of epileptiform activity by treating neonatal brain slices with 0 $Mg^{2+}$ artificial cerebral spinal fluid (aCSF).

Mg2+-free aCSF induced epileptic activity significantly upregulated CLC-3 channel expression in neonatal brain slices (e.g., P8-P12). FIGS. 12A and 12B; control: 11.2±1.5 artificial units (n=10); 0 $Mg^{2+}$: 20.4±2.8 artificial units (n=11); P<0.02, Student's t-test. This upregulation of CLC-3 channel expression subsequent to epileptiform activity was further confirmed by Western blot. FIGS. 12C and 12D. Moreover, patch-clamp recordings also revealed a significant increase of outward rectifying Cl- currents after the induction of epileptiform activity, and application of NaGcA significantly blocked the Cl- currents. FIGS. 12E and 12F; control: 31.2±1.8 pA/pF (n=15); 0 $Mg^{2+}$: 42.2±2.4 pA/pF (n=15); NaGcA: 7.3±0.6 pA/pF (n=11); P<0.001, one-way ANOVA with Tukey post hoc tests. These results suggest that CLC-3 channels may play a role during neonatal epilepsy.

To directly test this hypothesis, CLC-3 channels were inhibited with NaGcA and examined for effects upon epileptic activities. Remarkably, the data showed that NaGcA exerted a potent anti-epileptic effect in brain slices from young postnatal animals (P6-12). FIGS. 12G, 12H, 12I and 12J. However, the anti-epileptic effect of NaGcA became much smaller in older animals, for example those around one month of age (e.g. P26).

FIGS. 12K and 12L. Quantitatively, NaGcA inhibited 60% of the average power of epileptiform activity in early postnatal animals (P6-8: 59.6±4.3% (n=10); P10-12: 62.1±3.8% (n=10); P<0.001, paired t-test). However, in older animals power was reduced by only 20% after weaning (P21-33: 23.8±4.1% (n=7); p<0.005, paired t-test). FIG. 12M. Such a dramatic difference in NaGcA inhibition of epileptic activity between neonates and adult animals is consistent with the relative inhibition of NaGcA on CLC-3 Cl- currents in different ages of animals, suggesting that CLC-3 channels may play a role in neonatal epilepsy.

To further investigate the functional role of CLC-3 channels in epileptiform activity, epileptiform burst activity could be induced by $Mg^{2+}$-free aCSF in CLC-3 KO mice hippocampal slices, but for a much shorter timeperiod when in comparison to the WT mice. Interestingly, when hippocampal slices from WT mice were pre-treated with NaGcA to block CLC-3 channels, the epileptiform activity also did not last very long, mimicking what was observed in CLC-3 KO mice. FIGS. 12N and 12O. Quantified data showed that when CLC-3 channels were either inhibited or knocked out, the burst latency was significantly prolonged, and the total burst activity significantly reduced. FIG. 12P. Together, these data suggest that CLC-3 Cl- channels may play a role during epileptogenesis in early developing brains.

Whether the NaGcA effect on neonatal epileptic activity can be generally applicable to other epilepsy models beyond the 0 Mg2+ model was also examined. For example, the K+ channel blocker 4-AP (50 µM) was added into the bath solution to induce robust epileptic burst activity in immersed hippocampal slices. FIG. 13A. Addition of 20 mM NaGcA to the 4-AP solution significantly reduced the epileptic activity, which was reversible after washout of NaGcA. FIGS. 13A, 13B and 13C. 70.2±5.3% reduction of the power amplitude by NaGcA (n=9). (P<0.001, paired t-test). Elevated extracellular K+ (8.5 mM) was also used to evoke epileptic burst activity. FIG. 13D. Similarly, addition of 20 mM NaGcA in high K+ aCSF also dramatically reduced the epileptic burst activity. FIGS. 13D, 13E and 13F. NaGcA reduced the power amplitude by 70.8±4.9% (n=5). (P<0.001, paired t-test). In summary, these results demonstrate that NaGcA can potently suppress neonatal epilepsy in a variety of epilepsy models.

VI. Gluconate Inhibits Neonatal Epilepsy

In one embodiment, the present invention contemplates a method comprising treating neonatal epilepsy with a gluconate compound. In one embodiment, the gluconate compound is administered systemically.

For example, neonatal rats were administered gluconate to determine the effect on in vivo epileptic seizures in neonatal and adult animals. To induce seizures, the neurotoxin kainic acid (KA) (2 mg/kg, i.p.) was injected into neonatal rats (P10-12) to elicit robust seizure activities as revealed by in vivo EEG recordings. FIGS. 14A and 14B; Dzhala et al., "NKCC1 transporter facilitates seizures in the developing brain" *Nature Medicine* 11:1205-1213 (2005). Furthermore, when NaGcA (2 g/kg, i.p.) was injected 10 min after KA injection, the epileptic seizure activity was essentially abolished in neonatal animals. FIGS. 14C and 14D.

The anti-epileptic effect of gluconate was also compared with previously reported anti-convulsant drugs such as phenobarbital and bumetanide in neonatal animals. Phenobarbital is currently the drug of first choice to treat neonatal seizures, despite only ~50% efficacy and potential negative neurodevelopmental consequences. Slaughter et al., "Pharmacological treatment of neonatal seizures: a systematic review" *Journal Of Child Neurology* 28:351-364 (2013). Bumetanide is a potent loop diuretic, currently under evaluation as a prospective antiepileptic drug. Loscher et al., "Cation-chloride cotransporters NKCC1 and KCC2 as potential targets for novel antiepileptic and antiepileptogenic treatments" *Neuropharmacology* 69:62-74 (2013). While both phenobarbital and bumetanide inhibited epileptic activity to certain degree in neonatal animals, their inhibition was not as potent as gluconate. Cf FIGS. 14E-14H with FIGS. 14C and 14D. Quantitatively, when the EEG power was calculated in the last 30 min during a 2-hr recording period after KA injection, the relative power was reduced by 72.3% in NaGcA group, 35.5% in phenobarbital group, and 54.3% in bumetanide group, respectively. FIG. 14M. Therefore, gluconate appears to be a potent anti-epileptic drug for the treatment of neonatal seizure.

The anti-epileptic effect of gluconate was also compared in adult animals. Unlike the strong inhibition of neonatal seizure, gluconate showed less inhibition on adult seizure activity. FIGS. 14I-14L and 14N. These data are consistent with brain slice recording results. FIGS. 14G-14M. In addition, neonatal animals were tested regarding the effect of NaGcA on stable epileptic activity induced by KA, and found that NaGcA still suppressed seizure activity one hour after KA injection. FIG. 15. Therefore, these data allows the conclusion that NaGcA is an effective drug to treat neonatal seizure.

VII. CLC-3 Channels Regulate Cl− Homeostasis During Epileptogenesis

Although it is not necessary to understand the mechanism of an invention, it is believed that changes in $[Cl-]_i$ may represent at least one molecular mechanism of CLC-3 channels in neonatal epilepsy because the CLC-3 channel is a voltage-dependent outward rectifying Cl− channel. For example, the epileptic burst activity has often lasted more than 10 s. FIG. 16A.

To investigate the effect of such long-lasting epileptiform bursts on GABA function, gramicidin-perforated whole-cell recordings were performed to keep the intracellular Cl⁻ intact in neonatal animals. GABAA receptor (GABAA-R) currents induced by the receptor agonist isoguvacine (100 μM, 50 ms) before and after a membrane-depolarizing shift (40 mV for 10 s) that mimics the epileptiform burst activity. Interestingly, the GABAA-R current was significantly increased after membrane depolarization shift in WT, but not CLC-3 KO neurons, nor in the presence of CLC-3 channel blocker NaGcA. FIGS. 16B and 16C. These data suggest that CLC-3 channels may regulate GABA function during epileptogenesis in neonatal animals.

To further test this idea, the GABAA-R reversal potential (EGABA), which governs GABA excitatory versus inhibitory function, was directly measured using gramicidin-perforated whole-cell recordings in neonatal mouse brain slices (e.g., P8-P9). As expected, epileptiform activity induced a large depolarizing shift in EGABA after treating hippocampal slices with 0 $Mg^{2+}$ aCSF for 1 h (aCSF: −59.2±2.0 mV, n=13; 0 $Mg^{2+}$: −48.2±1.1 mV, n=10). FIG. 16D. Treatment with bumetanide (Bum, 10 μM), a specific blocker for NKCC1 at low concentrations, induced a hyperpolarizing shift in EGABA (blue line) as compared to a control EGABA (dashed line). FIG. 6E. These results are consistent with reports that NKCC1 imports Cl− into neuronal cells. Kaila et al., "Cation-chloride cotransporters in neuronal development, plasticity and disease" *Nature Reviews. Neuroscience* 15:637-654 (2014); Dzhala et al., "NKCC1 transporter facilitates seizures in the developing brain" *Nature Medicine* 11:1205-1213 (2005); and Loscher et al., "Cation-chloride cotransporters NKCC1 and KCC2 as potential targets for novel antiepileptic and antiepileptogenic treatments" *Neuropharmacology* 69:62-74 (2013). However, in the presence of bumetanide, epileptiform activity still caused a depolarizing shift of EGABA, suggesting that a factor other than NKCC1 is regulating EGABA during epileptogenesis. FIG. 16E, yellow line; Bum, −68.0±1.7 mV (n=9); 0 $Mg^{2+}$+Bum, −50.2±1.4 mV (n=9); (p<0.002).

Treatment with KCC2 blocker VU0240551 (10 μM) did not affect the EGABA in neonatal animals. FIG. 16F, purple line; −60.8±1.9 mV (n=6). These data may possibly be explained as due to a low expression level of KCC2 at this early time. Epileptic activity also elicited a positive shift in EGABA. FIG. 16F, orange line; −48.9±1.3 mV (n=8). Therefore, the epileptiform activity-induced EGABA shift is not controlled by NKCC1 or KCC2 in neonatal animals.

On the other hand, when CLC-3 Cl− channels were inhibited with NaGcA (20 mM), the EGABA was not further altered when exposed to 0 $Mg^{2+}$ aCSF. FIG. 16G; 0 $Mg^{2+}$+NaGcA: −59.3±1.7 mV (n=6). Furthermore, in CLC-3 KO mice, the EGABA was also not changed in 0 $Mg^{2+}$ aCSF. FIG. 16H; CLC-3 KO+0 $Mg^{2+}$: −55.6±2.1 mV (n=10). Additionally, application of NaGcA in CLC-3 KO mice had no more effect on EGABA in 0 $Mg^{2+}$ aCSF (−56.6±2.4 mV, n=5). Inhibition of CLC-3 channels with NaGcA or knock out CLC-3, didn't change the normal EGABA in the normal conditions. FIG. 16G; NaGcA: −60.3±0.9 mV (n=5); CLC-3 KO: −55.4±2.9 mV (n=9).

Therefore, these results suggest that CLC-3 Cl− channels play a role in controlling EGABA during epileptogenesis in neonatal animals. In older animals (e.g., P30-90), however, 0 $Mg^{2+}$ aCSF still induced a large depolarizing shift in EGABA in the presence of NaGcA. FIG. 16J. These data are consistent with observations that the CLC-3 channel-mediated outward rectifying Cl− currents are substantially decreased in the adult animals. FIG. 16A.

Besides EGABA, the effects of different drugs on GABA-induced neuronal activity during epileptogenesis were investigated in neonatal animals (e.g., P8-9). To accurately measure GABA-induced neuronal activity, cell-attached recordings monitored spike firing elicited by local application of the GABAA-R agonist isoguvacine (10 μM, 30 s). Tyzio et al., "Maternal oxytocin triggers a transient inhibitory switch in GABA signaling in the fetal brain during delivery" *Science* 314:1788-1792 (2006). The majority of resting CA3 pyramidal neurons did not respond to isoguvacine. FIG. 16K, control, (n=32). However, after 0 $Mg^{2+}$ treatment, 68% of neurons showed spike activity upon isoguvacine application. FIG. 16K, 0 $Mg^{2+}$ (n=19). Blocking NKCC1 with bumetanide or blocking KCC2 with VU0240551 did not change the spike activity elicited by isoguvacine. FIG. 16K; 0 $Mg^{2+}$+Bum (n=19); and 0 $Mg^{2+}$+VU (n=21). In contrast, application of NaGcA to inhibit CLC-3 Cl− channels essentially abolished the spike activity induced by isoguvacine after 0 $Mg^{2+}$ treatment. FIG. 16K; 0 $Mg^{2+}$+NaGcA (n=18). Quantified data for these observations are shown in FIG. 4L.

These data indicate that activation of CLC-3 Cl− channels in neonatal animals enhances GABA excitatory activity during epileptogenesis, and blocking CLC-3 channels is an effective way to inhibit neonatal seizure through reducing excitatory GABA activity.

VIII. Pharmaceutical Formulations and/or Compositions

The present invention further provides pharmaceutical compositions (e.g., comprising the compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. In particular, an intramuscular injection and/or intravenous injection of sodium gluconate may be delivered in a sterile saline solution at an approximate concentration range of 1-100 mM gluconate. Although it is not necessary to understand the mechanism of an invention it is believed that these concentration ranges are achievable because sodium gluconate is highly water soluble.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 µg to 100 g per kg of body weight, once or more daily, to once every 20 years.

V. Drug Delivery Systems

The present invention contemplates several drug delivery systems that provide for roughly uniform distribution, have controllable rates of release. A variety of different media are described below that are useful in creating drug delivery systems. It is not intended that any one medium or carrier is limiting to the present invention. Note that any medium or carrier may be combined with another medium or carrier; for example, in one embodiment a polymer microparticle carrier attached to a compound may be combined with a gel medium.

Carriers or mediums contemplated by this invention comprise a material selected from the group comprising gelatin, collagen, cellulose esters, dextran sulfate, pentosan polysulfate, chitin, saccharides, albumin, fibrin sealants, synthetic polyvinyl pyrrolidone, polyethylene oxide, polypropylene oxide, block polymers of polyethylene oxide and polypropylene oxide, polyethylene glycol, acrylates, acrylamides, methacrylates including, but not limited to, 2-hydroxyethyl methacrylate, poly(ortho esters), cyanoacrylates, gelatin-resorcin-aldehyde type bioadhesives, polyacrylic acid and copolymers and block copolymers thereof.

One embodiment of the present invention contemplates a drug delivery system comprising therapeutic agents as described herein.

Microparticles

One embodiment of the present invention contemplates a medium comprising a microparticle. Preferably, microparticles comprise liposomes, nanoparticles, microspheres, nanospheres, microcapsules, and nanocapsules. Preferably, some microparticles contemplated by the present invention comprise poly(lactide-co-glycolide), aliphatic polyesters including, but not limited to, poly-glycolic acid and poly-lactic acid, hyaluronic acid, modified polysaccharides, chitosan, cellulose, dextran, polyurethanes, polyacrylic acids, psuedo-poly(amino acids), polyhydroxybutrate-related copolymers, polyanhydrides, polymethylmethacrylate, poly (ethylene oxide), lecithin and phospholipids.

Liposomes

One embodiment of the present invention contemplates liposomes capable of attaching and releasing therapeutic agents described herein. Liposomes are microscopic spherical lipid bilayers surrounding an aqueous core that are made from amphiphilic molecules such as phospholipids. For example, a liposome may trap a therapeutic agent between the hydrophobic tails of the phospholipid micelle. Water soluble agents can be entrapped in the core and lipid-soluble agents can be dissolved in the shell-like bilayer. Liposomes have a special characteristic in that they enable water soluble and water insoluble chemicals to be used together in a medium without the use of surfactants or other emulsifiers. Liposomes can form spontaneously by forcefully mixing phosopholipids in aqueous media. Water soluble compounds are dissolved in an aqueous solution capable of hydrating phospholipids. Upon formation of the liposomes, therefore, these compounds are trapped within the aqueous liposomal center. The liposome wall, being a phospholipid membrane, holds fat soluble materials such as oils. Liposomes provide controlled release of incorporated compounds. In addition, liposomes can be coated with water soluble polymers, such as polyethylene glycol to increase the pharmacokinetic half-life. One embodiment of the present invention contemplates an ultra high-shear technology to refine liposome production, resulting in stable, unilamellar (single layer) liposomes having specifically designed structural characteristics. These unique properties of liposomes, allow the simultaneous storage of normally immiscible compounds and the capability of their controlled release.

In some embodiments, the present invention contemplates cationic and anionic liposomes, as well as liposomes having neutral lipids. Preferably, cationic liposomes comprise negatively-charged materials by mixing the materials and fatty acid liposomal components and allowing them to charge-associate. Clearly, the choice of a cationic or anionic liposome depends upon the desired pH of the final liposome mixture. Examples of cationic liposomes include lipofectin, lipofectamine, and lipofectace.

One embodiment of the present invention contemplates a medium comprising liposomes that provide controlled release of at least one therapeutic agent. Preferably, liposomes that are capable of controlled release: i) are biodegradable and non-toxic; ii) carry both water and oil soluble compounds; iii) solubilize recalcitrant compounds; iv) prevent compound oxidation; v) promote protein stabilization; vi) control hydration; vii) control compound release by variations in bilayer composition such as, but not limited to, fatty acid chain length, fatty acid lipid composition, relative amounts of saturated and unsaturated fatty acids, and physical configuration; viii) have solvent dependency; iv) have pH-dependency and v) have temperature dependency.

The compositions of liposomes are broadly categorized into two classifications. Conventional liposomes are generally mixtures of stabilized natural lecithin (PC) that may comprise synthetic identical-chain phospholipids that may or may not contain glycolipids. Special liposomes may comprise: i) bipolar fatty acids; ii) the ability to attach antibodies for tissue-targeted therapies; iii) coated with materials such as, but not limited to lipoprotein and carbohydrate; iv) multiple encapsulation and v) emulsion compatibility.

Liposomes may be easily made in the laboratory by methods such as, but not limited to, sonication and vibration. Alternatively, compound-delivery liposomes are commercially available. For example, Collaborative Laboratories, Inc. are known to manufacture custom designed liposomes for specific delivery requirements.

Microspheres, Microparticles and Microcapsules

Microspheres and microcapsules are useful due to their ability to maintain a generally uniform distribution, provide stable controlled compound release and are economical to produce and dispense. Preferably, an associated delivery gel or the compound-impregnated gel is clear or, alternatively, said gel is colored for easy visualization by medical personnel.

Microspheres are obtainable commercially (Prolease®, Alkerme's: Cambridge, Mass.). For example, a freeze dried medium comprising at least one therapeutic agent is homogenized in a suitable solvent and sprayed to manufacture microspheres in the range of 20 to 90 µm. Techniques are then followed that maintain sustained release integrity during phases of purification, encapsulation and storage. Scott et al., Improving Protein Therapeutics With Sustained Release Formulations, Nature Biotechnology, Volume 16:153-157 (1998).

Modification of the microsphere composition by the use of biodegradable polymers can provide an ability to control the rate of therapeutic agent release. Miller et al., Degradation Rates of Oral Resorbable Implants {Polylactates and Polyglycolates: Rate Modification and to Changes in PLA/PGA Copolymer Ratios, J. Biomed. Mater. Res., Vol. II:711-719 (1977).

Alternatively, a sustained or controlled release microsphere preparation is prepared using an in-water drying method, where an organic solvent solution of a biodegradable polymer metal salt is first prepared. Subsequently, a dissolved or dispersed medium of a therapeutic agent is added to the biodegradable polymer metal salt solution. The weight ratio of a therapeutic agent to the biodegradable polymer metal salt may for example be about 1:100000 to about 1:1, preferably about 1:20000 to about 1:500 and more preferably about 1:10000 to about 1:500. Next, the organic solvent solution containing the biodegradable polymer metal salt and therapeutic agent is poured into an aqueous phase to prepare an oil/water emulsion. The solvent in the oil phase is then evaporated off to provide microspheres. Finally, these microspheres are then recovered, washed and lyophilized. Thereafter, the microspheres may be heated under reduced pressure to remove the residual water and organic solvent.

Other methods useful in producing microspheres that are compatible with a biodegradable polymer metal salt and therapeutic agent mixture are: i) phase separation during a gradual addition of a coacervating agent; ii) an in-water drying method or phase separation method, where an anti-flocculant is added to prevent particle agglomeration and iii) by a spray-drying method.

In one embodiment, the present invention contemplates a medium comprising a microsphere or microcapsule capable of delivering a controlled release of a therapeutic agent for a duration of approximately between 1 day and 6 months. In one embodiment, the microsphere or microparticle may be colored to allow the medical practitioner the ability to see the medium clearly as it is dispensed. In another embodiment, the microsphere or microcapsule may be clear. In another embodiment, the microsphere or microparticle is impregnated with a radio-opaque fluoroscopic dye.

Controlled release microcapsules may be produced by using known encapsulation techniques such as centrifugal extrusion, pan coating and air suspension. Such microspheres and/or microcapsules can be engineered to achieve desired release rates. For example, Oliosphere® (Macromed) is a controlled release microsphere system. These particular microsphere's are available in uniform sizes ranging between 5-500 μm and composed of biocompatible and biodegradable polymers. Specific polymer compositions of a microsphere can control the therapeutic agent release rate such that custom-designed microspheres are possible, including effective management of the burst effect. ProMaxx® (Epic Therapeutics, Inc.) is a protein-matrix delivery system. The system is aqueous in nature and is adaptable to standard pharmaceutical delivery models. In particular, ProMaxx® are bioerodible protein microspheres that deliver both small and macromolecular drugs, and may be customized regarding both microsphere size and desired release characteristics.

In one embodiment, a microsphere or microparticle comprises a pH sensitive encapsulation material that is stable at a pH less than the pH of the internal mesentery. The typical range in the internal mesentery is pH 7.6 to pH 7.2. Consequently, the microcapsules should be maintained at a pH of less than 7. However, if pH variability is expected, the pH sensitive material can be selected based on the different pH criteria needed for the dissolution of the microcapsules. The encapsulated compound, therefore, will be selected for the pH environment in which dissolution is desired and stored in a pH preselected to maintain stability. Examples of pH sensitive material useful as encapsulants are Eudragit® L-100 or S-100 (Rohm GMBH), hydroxypropyl methylcellulose phthalate, hydroxypropyl methylcellulose acetate succinate, polyvinyl acetate phthalate, cellulose acetate phthalate, and cellulose acetate trimellitate. In one embodiment, lipids comprise the inner coating of the microcapsules. In these compositions, these lipids may be, but are not limited to, partial esters of fatty acids and hexitiol anhydrides, and edible fats such as triglycerides. Lew C. W., Controlled-Release pH Sensitive Capsule And Adhesive System And Method. U.S. Pat. No. 5,364,634 (herein incorporated by reference).

In one embodiment, the present invention contemplates a microparticle comprising a gelatin, or other polymeric cation having a similar charge density to gelatin (i.e., poly-L-lysine) and is used as a complex to form a primary microparticle. A primary microparticle is produced as a mixture of the following composition: i) Gelatin (60 bloom, type A from porcine skin), ii) chondroitin 4-sulfate (0.005%-0.1%), iii) glutaraldehyde (25%, grade 1), and iv) 1-ethyl-3-(3-dimethylaminopropyl)-carbodiimide hydrochloride (EDC hydrochloride), and ultra-pure sucrose (Sigma Chemical Co., St. Louis, Mo.). The source of gelatin is not thought to be critical; it can be from bovine, porcine, human, or other animal source. Typically, the polymeric cation is between 19,000-30,000 daltons. Chondroitin sulfate is then added to the complex with sodium sulfate, or ethanol as a coacervation agent.

Following the formation of a microparticle, a therapeutic agent is directly bound to the surface of the microparticle or is indirectly attached using a "bridge" or "spacer". The amino groups of the gelatin lysine groups are easily derivatized to provide sites for direct coupling of a compound. Alternatively, spacers (i.e., linking molecules and derivatizing moieties on targeting ligands) such as avidin-biotin are also useful to indirectly couple targeting ligands to the microparticles. Stability of the microparticle is controlled by the amount of glutaraldehyde-spacer crosslinking induced by the EDC hydrochloride. A controlled release medium is also empirically determined by the final density of glutaraldehyde-spacer crosslinks.

In one embodiment, the present invention contemplates microparticles formed by spray-drying a composition comprising fibrinogen or thrombin with a therapeutic agent. Preferably, these microparticles are soluble and the selected protein (i.e., fibrinogen or thrombin) creates the walls of the microparticles. Consequently, the therapeutic agents are incorporated within, and between, the protein walls of the microparticle. Heath et al., Microparticles And Their Use In Wound Therapy. U.S. Pat. No. 6,113,948 (herein incorporated by reference). Following the application of the microparticles to living tissue, the subsequent reaction between the fibrinogen and thrombin creates a tissue sealant thereby releasing the incorporated compound into the immediate surrounding area.

One having skill in the art will understand that the shape of the microspheres need not be exactly spherical; only as very small particles capable of being sprayed or spread into or onto a surgical site (i.e., either open or closed). In one embodiment, microparticles are comprised of a biocompatible and/or biodegradable material selected from the group consisting of polylactide, polyglycolide and copolymers of lactide/glycolide (PLGA), hyaluronic acid, modified polysaccharides and any other well known material.

EXPERIMENTAL

Animal protocols for cell cultures and brain slices were approved by Pennsylvania State University IACUC in accordance with the National Institutes of Health Guide for the Care and use of Laboratory Animals. For in vivo experiments on adult mice or neonatal rats, all procedures were approved by the Committee of Animal Use for Research and Education of Fudan University or South China Normal University, respectively, in accordance with the ethical guidelines for animal research. Animal rooms were automatically controlled at 12 hr light/dark cycle, and water and food were available ad libitum.

Example I

Cell Culture and Transfection

Mouse cortical neurons were prepared from newborn C57BL/6 mice as previously described. Qi et al., "Cyclothiazide induces robust epileptiform activity in rat hippocampal neurons both in vitro and in vivo" *The Journal Of Physiology* 571:605-618 (2006). Briefly, the newborn mouse cerebral cortices were dissected out in ice-cold HEPES-buffered saline solution, washed and digested with 0.05% trypsin-EDTA at 37° C. for 20 min. After deactivation of trypsin with serum-containing medium, cells were centrifuged, resuspended, and seeded on a monolayer of cortical astrocytes at a density of 10,000 cells/cm$^2$ in 24-well plates. The neuronal culture medium contained MEM (500 ml, Invitrogen), 5% fetal bovine serum (Atlanta Biologicals), 10 ml B-27 supplement (Invitrogen), 100 mg NaHCO3, 2 mM Glutamax (Invitrogen), and 25 units/ml penicillin & streptomycin. AraC (4 μM, Sigma) was added to inhibit the excessive proliferation of astrocytes. Cell cultures were maintained in a 5% CO$_2$-humidified incubator at 37° C. for 14-21 days.

Human embryonic kidney (HEK) 293T cells were maintained in DMEM supplemented with 10% FBS and 25 units/ml penicillin/streptomycin. PEI kit (molecular weight 25,000, Polysciences, Inc.) was applied for HEK cell transfection. In brief, 1 μg DNA was diluted into 50 μl of OptiMEM (Invitrogen), then mixed with 4 μl of PEI (1 μg/μl), incubated for 5 min, and added drop-by-drop to the culture well containing 500 μl of medium. After 5 hr incubation, the transfection reagents were washed off by fresh culture medium. Two days after transfection, HEK293T cells were used for electrophysiological study. Rat CLC-3 short transcript fused to eGFP plasmid (pCLC3sGFP) was purchased from Addgene (plasmid #52423). Li et al., "The ClC-3 chloride channel promotes acidification of lysosomes in CHO-K1 and Huh-7 cells" American Journal Of Physiology" *Cell Physiology* 282: C1483-1491 (2002).

Example II

Cell Viability Assay

A LIVE/DEAD® Viability/Cytotoxicity Assay Kit (L3224, Life Technologies) containing ethidium homodimer-1 and calcein-AM was used to examine cell viability. Ethidium homodimer-1 binds to cellular DNA and typically labels dead cells in red fluorescence, while Calcein-AM can be cleaved by esterases in live cells to give strong green fluorescence. After drug treatment, neurons were incubated in bath solution containing 1 µM calcein-AM and 4 µM ethidium homodimer-1 at room temperature for 40 min. Cell survival and death rate were measured by quantifying the percentage of green and red fluorescent cells, respectively. For each group, at least 5 fields of each coverslip were imaged for data analysis.

Example III

Mouse Brain Slice Preparation

Brain slices were prepared from C57BL/6 mice (male and female). Animals were anesthetized with Avertin (tribromoethanol, 250 mg/kg) and decapitated. Hippocampal horizontal sections (400 µm) were prepared by Leica VT1200S vibratome in ice-cold artificial cerebral spinal fluid (aCSF) (in mM): 125 NaCl, 26 NaHCO$_3$, 10 glucose, 2.5 KCl, 2.5 CaCl$_2$, 1.25 NaH$_2$PO$_4$, and 1.3 MgSO$_4$, osmolarity 290-300 mOsm, aerated with 95% O$_2$/5% CO$_2$. Slices were then transferred to incubation chamber containing normal aCSF saturated with carbogen (95% O$_2$/5% CO$_2$) at 33° C. for 30 mM, followed by recovery at room temperature for 1 hour before use. Individual slice was transferred to a submerged recording chamber where they were continuously perfused (2-3 ml/min) with aCSF saturated by 95% O$_2$/5% CO$_2$ at 31-33° C. (TC-324B, Warner instruments Inc). Slices were visualized with infrared optics using an Olympus microscope equipped with DIC optic.

Example IV

Electrophysiology

Cell Culture

The cultured neurons were placed in the recording chamber with continuous perfusion of the bath solution consisting of (mM): 128 NaCl, 10 Glucose, 25 HEPES, 5 KCl, 2 CaCl$_2$, 1 MgSO$_4$, pH 7.3 adjusted with NaOH, and osmolarity ~300 mOsm. For recording spontaneous firing under current clamp mode, pipettes were filled with an internal solution containing (in mM): 125 K-gluconate, 5 Na-phosphocreatine, 5 EGTA, 10 KCl, 10 HEPES, 4 Mg-ATP, 0.3 Na-GTP, 280-290 mOsm, pH 7.3 adjusted with KOH. Epileptiform activity in cultured neurons was induced either by 10 µM CTZ for 24 h, or 1 µM KA for 2 h, or 50 µM 4-AP for 2 h.

The burst activity was defined as previously described. Qi et al., "Cyclothiazide induces robust epileptiform activity in rat hippocampal neurons both in vitro and in vivo" *The Journal Of Physiology* 571:605-618 (2006). In brief, at least five consecutive action potentials overlaying on top of the large depolarization shift (>10 mV depolarization and >300 ms in duration).

For Cl$^-$ current recording, a 0 Ca2+ pipette solution contained (mM): 125 CsCl, 5 Na-phosphocreatine, 10 HEPES, 5 EGTA, 5 TEACl, 4 MgATP (pH 7.3 adjusted with CsOH, 280-290 mOsm).

To isolate Cl$^-$ current: (1) Extracellular Na$^+$ was replaced by NMDG$^+$ and voltage-dependent Na$^+$ channels were blocked by tetrodotoxin (TTX); (2) K$^+$ and Ca$^{2+}$ were removed from bath solution; (3) K$^+$ channels were blocked with Cs$^+$ and tetraethylamonium (TEA) in the pipette solution, and 4-AP in the bath solution; (4) CdCl$_2$ was added into bath solution to block Ca$^{2+}$ channels; (5) Picrotoxin (50 µM) was also included to block GABAA receptors. Thus, the external solution contained the following (in mM): 135 NMDG-Cl, 20 HEPES, 20 Glucose, 5 4-AP and 2 MgSO$_4$, supplemented with 1 µM TTX, 200 µM CdCl$_2$, and 50 µM picrotoxin, osmolarity ~300 mOsm, pH7.3-7.4 after aerated with 95% O2/5% CO$_2$. Voltage steps from −80 to +90 mV (10 mV increments) were applied from holding potential of 0 mV (ECl$^-$~0 mV). Data were collected with a MultiClamp 700A amplifier and pCLAMP9 software (Molecular Devices).

Brain Slice Recording

Field potential recordings were performed with glass electrodes (2-4 MΩ tip resistance) filled with external solution. The glass electrode was placed into the CA3 pyramidal layer. For current clamp (I=0) recordings, the amplifier was set at the 100× with a band pass filter of 0.1-5 KHz. All recordings were performed at 31-33° C. The epileptic activity was evoked by Mg$^{2+}$-free aCSF, or addition of 50 µM 4-AP or 8.5 mM K$^+$ in the aCSF.

A Hamming window function was applied before power spectrum analysis. Power was calculated by integrating the root mean square value of the signal in frequency bands from 0.1 to 1000 Hz in sequential 5-min time windows before, during, and after drug applications. To avoid slice-to-slice and electrode contact variability, power values were normalized to control condition before drug application for each slice, and then averaged across different slices for statistical analysis.

Example V

Immunostaining and Western-Blot

Brain slices were prepared following the electrophysiology protocol described above, with 200 µm thickness for immunostaining and 400 µm thickness for Western-blot. In general, slices were recovered for 1 hr at room temperature and then randomly divided into two groups. One group of slices was incubated in normal aCSF for 1 hr at 33° C. Another group of slices were incubated in 0 Mg$^{2+}$ aCSF for 1 hr at 33° C. Slices were then fixed by 4% PFA overnight at 4° C.

Immunostaining

For CLC-3 staining, slices were pretreated with blocking solution (0.3% Triton-X and 5% normal donkey and goat serum in 0.1 M PBS) for 2 hr, and then incubated for 72 hr with CLC-3 primary antibody (Rabbit, 1:200, Alomone, ACL-001). Some slices were incubated with rabbit IgG as control. After washing three times in PBS with 0.01% triton-X, the brain sections were incubated with goat anti rabbit secondary antibodies conjugated to Cy3 (1:500, Jackson ImmunoResearch) for 2 hr at room temperature. The brain sections were mounted on a glass slide with an anti-fading mounting solution (Invitrogen). Fluorescent images were acquired on an Olympus confocal microscope system (FV1000). For each slice, at least 2-3 fields of CA3 were imaged. To quantify CLC3 fluorescent intensity in CA3 pyramidal layer, confocal images were analyzed using NIH Image J software.

Western Blot

400 µm thickness hippocampal slices were randomly divided into two groups after recovery for 1 hr at room temperature, which were the same as described above for immunostaining. The hippocampus was dissected out in ice-cold aCSF. Proteins were extracted with RIPA lysis buffer (containing 1:100 Phenylmethylsulfonyl fluoride and 1:200 Protease inhibitor). Then, add 1× loading dye buffer (NuPAGE LDS sample buffer (4×)) and 1% beta-ME into the protein sample, and mix thoroughly. Protein extracts (2 µg/µl, 15 µl per lane) were boiled at 55° C. for 20 min, loaded on 10% gel, separated using sodium dodecyl sulfate polyacrylamide gel electrophoresis (SDS-PAGE) (70V for 50 min then switch to 90V for 2 hrs) at room temperature. Then the gel was blotted onto a PVDF membrane. Blots were blocked using a solution of 5% milk in 1% Tween-20 in Tris-buffered solution (1×TBS) for 1 hr at room temperature. The primary antibodies to CLC3 (Rabbit, 1:300, Alomone, ACL-001) and GAPDH (Rabbit, 1:20000, Sigma, G9545) were applied overnight on a rotator at 4° C. in blocking solution containing 5% milk and 1% Tween-20 in 1×TBS. Blots were then incubated with anti-rabbit secondary antibodies at 1:20000 dilution for 1.5 hrs at room temperature, washing three times using 1×TBS, and then imaging the signal with the Odyssey scanner system (Li-Cor Biosciences).

Example VI

Electroencephalogram (EEG) Recording

To test the in vivo anti-epilepsy effects of gluconate in neonatal and adult rodents, P8-12 Sprague-Dawley rats or 2-month old male C57BL/6 mice were deeply anesthetized with pentobarbital sodium (50 mg/kg for neonatal rat and 100 mg/kg for adult mice, intraperitoneal injection). Two stainless steel screws (1 mm in diameter) were inserted in the skull above the cortex as EEG recording electrodes, one ground electrode as well as one reference electrode were located +1.8 mm anterior to bregma, ±0.5 mm lateral to the midline, and 1 mm below the cortical surface. All electrodes were attached to a micro-connector and fixed onto the skull with dental cement. After surgery, neonatal rats were returned to their mothers and allowed to recover for 2 days prior to subsequent EEG recording. The adult mice were single housed in order to prevent damage of the implanted electrodes and allowed to recover at least 5 days before EEG recording.

The baseline of EEG was recorded for 0.5-1 hr to allow the animal to adapt to the environment. Kainic acid (2 mg/kg) was administered intraperitoneally (i.p.) for neonatal epilepsy induction. D-gluconic acid sodium salt (2 g/kg) or 0.9% saline was injected i.p. 10 min after KA administration. Pentylenetetrazol (PTZ) was administered intraperitoneally for inducing a stable epileptic burst activity in adult mice, and D-gluconic acid sodium salt (1 g/kg and 2 g/kg) or 0.9% saline was injected i.p. 10 min before PTZ administration. Epileptiform activity was monitored for 1 hr after PTZ injection. Qian et al., "Epileptiform response of CA1 neurones to convulsant stimulation by cyclothiazide, kainic acid and pentylenetetrazol in anaesthetized rats" *Seizure* 20:312-319 (2011). After the experiment, animals were injected with diazepam to protect the animals from recurrent epilepsy.

The electrophysiological signals were amplified (1000×) and filtered (0-500 Hz) by using a NeuroLog System (Digitimer Ltd, Hearts, UK) and visualized and stored in a PC through a D-A converter, CED 1401 micro (Cambridge Electronic Design, Cambridge, UK).

Analysis of EEG

The power level of different frequency components in the neonatal EEG signal was revealed by power spectrum analysis. Power was calculated in 1-min time windows by integrating the power of dominant frequency bands from 1 to 100 Hz (EEG band).

Adult EEG signal were analyzed by spike 2 software (an analysis program for CED 1401, Cambridge, UK). The EEG spike was defined as exceeding twice of the baseline amplitude, and the EEG burst was defined as having high frequency (>1 Hz) and high amplitude multiple spikes lasting more than 10 s. The latency of spike or burst was defined as the time from PTZ injection to either the first spike or the first burst.

Example VII

Seizure Behavior Test

Male mice were divided into three groups: vehicle control group (saline, n=9), D-gluconic acid sodium at 1 g/kg group (n=10), and D-gluconic acid sodium at 2 g/kg group (n=11). PTZ (50 mg/kg) was intraperitoneally administered 1 hr after drug treatment. After PTZ injection, the behavior was monitored and observed for 1 hr. The seizure behavior was classified according to Racine Score: stage 0, no response; stage 1, facial twitching; stage 2, nod; stage 3, forelimb clonic, tail upright; stage 4, stand with forelimbs clonic; stage 5, stand and fall, jump, general clonic seizure, general clonic and tonic seizure or death. Racine et al., "Modification of seizure activity by electrical stimulation. 3. Mechanisms" *Electroencephalogr Clin Neurophysiol* 32:295-299 (1972).

Example VIII

Data Analysis

Data were shown as mean±s.e.m. Student's t-test (paired or unpaired) was performed for two-group comparison, and the $\chi 2$ test was used to compare the difference of percentage between two groups. For comparison among multiple groups, one-way ANOVA with post hoc tests were used. Statistical significance was set at $P<0.05$.

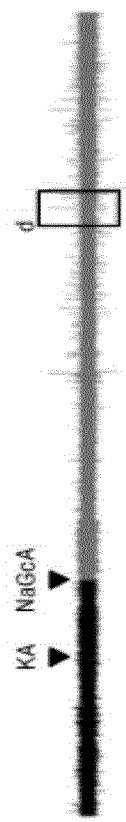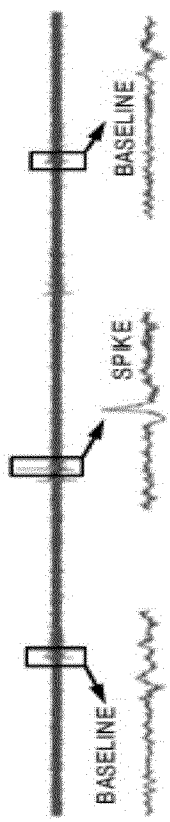

We claim:

1. A method, comprising:
 a) providing:
  i) a neonatal patient exhibiting convulsions;
  ii) a composition comprising a gluconate complex, wherein said gluconate complex lacks a divalent cation; and
 b) administering said composition to said patient under conditions such that said convulsions are reduced.

2. The method of claim 1, wherein said gluconate complex is sodium gluconate.

3. The method of claim 1, wherein said divalent cation is a calcium-based divalent cation therapy.

4. The method of claim 1, wherein said divalent cation is a magnesium-based divalent cation.

5. The method of claim 1, wherein said divalent cation is a zinc-based divalent cation.

6. The method of claim 1, wherein said gluconate complex comprises a gluconic acid derivative.

7. A method, comprising:
   a) providing:
      i) a neonatal patient exhibiting convulsions;
      ii) a composition consisting of a sodium gluconate complex, wherein said complex lacks a divalent cation; and
   b) administering said composition to said patient under conditions such that said convulsions are reduced.

8. The method of claim 7, wherein said divalent cation gluconate complex comprises a gluconic acid derivative.

9. A method, comprising:
   a) providing;
      i) a neonatal patient exhibiting convulsions, wherein said patient comprises at least one chloride ion channel;
      ii) a composition comprising a chloride ion channel blocker, wherein said chloride ion channel blocker comprises a gluconate complex that lacks a divalent cation; and
   b) administering said composition to said patient under conditions such that said convulsions are reduced.

10. The method of claim 9, wherein said chloride ion channel blocker further comprises a compound that is selected from the group consisting of niflumic acid (NFA), flufenamic acid, 4,4'-Diisothiocyanato-2,2'-stilbenedisulfonic acid disodium salt (DIDS), and 5-Nitro-2-(3-phenylpropylamino) benzoic acid (NPPB).

11. The method of claim 9, wherein said gluconate complex is sodium gluconate.

12. The method of claim 9, wherein said divalent cation is selected from the group consisting of a calcium-based divalent cation, a magnesium-based divalent cation, and a zinc-based divalent cation.

13. The method of claim 9, wherein said gluconate complex comprises a gluconic acid derivative.

14. The method of claim 1, wherein said composition further comprises phenobarbital.

15. The method of claim 9, wherein said composition further comprises phenobarbital.

* * * * *

UNITED STATES PATENT AND TRADEMARK OFFICE
CERTIFICATE OF CORRECTION

PATENT NO. : 9,861,597 B2
APPLICATION NO. : 15/155355
DATED : January 9, 2018
INVENTOR(S) : G. Chen and Z. Wu It is certified that error appears in the above-identified patent and that said Letters Patent is hereby corrected as shown below:

In the Drawings

Replace FIGS. 7A, 7B, 7C, 7D, 7E, 7F and 7G with FIGS. 7A, 7B, 7C, 7D, 7E, 7F and 7G as shown on the attached pages.

In the Specification

On Column Nine, Line 39 - 67 and Column 10, Line 1 - 2, should read as follows:
Figure 7 A – G presents exemplary data showing that gluconate is an effective therapy for KA induced neonatal seizure.
Figure 7 (a) Representative EEG trace from P12 rat, which injected with saline (0.1 ml/10 g, i.p.) 10 min after KA injection (2 mg/kg, i.p.), showed recurrent epileptic burst discharges.
Figure 7 (b) Expanded view of a single cluster-like epileptic discharges from the box b in Figure 7a showing.
Figure 7 (c) T typical traces of interictal, ictal-tonic and ictal-clonic traces expended form the box in b.
Figure 7 (c) Example EEG of P12 rat, which injected with NaGcA (2 g/kg, ip) 10 min after KA injection (2 mg/kg, i.p.), showing increase in spike activity but no robust burst discharges was developed after NaGcA administration. Scale bar same as in Figure 7a.
Figure 7 (d) Enlarged area of the box in d in Figure 7c. Scale bar same as in Figure 7b. Figure 7 (f) A single spike discharge was observed in the expanded trace as compared to two flanking baseline traces from e (box area). Scale bar same as in Figure 7c.
Figure 7 (e) Individual EEG power in 1 min time window of panel a and d.
Figure 7 (f) Group averaged EEG power in 1 min time window of saline (P10-12, n = 11) and NaGcA administration (P10-12, n = 11). The first arrowhead indicates the KA injection point, the second arrowhead indicates either saline or NaGcA injection point. The average power of epileptic activity induced by KA injection was 70% lower in the presence of NaGcA.
Figure 7 (g) Work model of our study. Cl- influx through chloride channels will facilitate synchronized network activity (left). But this process is suppressed by gluconic acid (GA) due to its inhibition on chloride channels (right).

Signed and Sealed this
Second Day of June, 2020

Andrei Iancu
*Director of the United States Patent and Trademark Office*

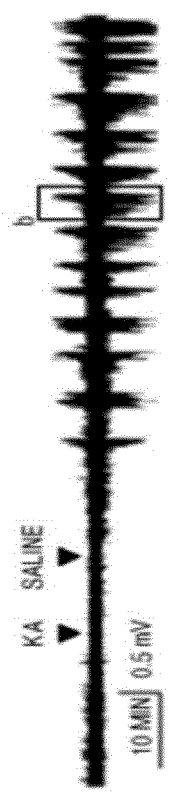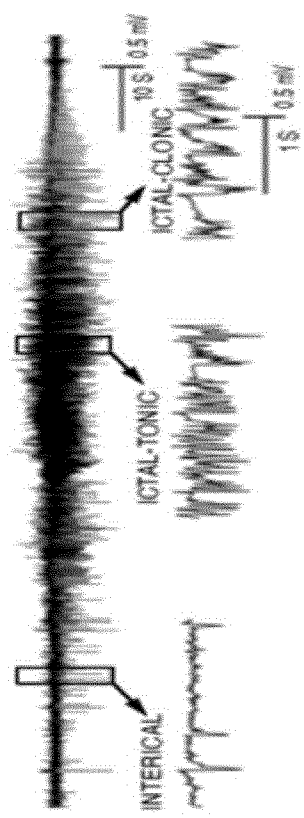
FIG. 7A
FIG. 7B